United States Patent [19]

Takaya et al.

[11] 4,331,664
[45] May 25, 1982

[54] SYN ISOMER OF 7-[2-CYCLO(LOWER) ALKOXYIMINO-2-(2-AMINO-OR SUBSTITUTED AMINOTHIAZOL-4-YL)ACETAMIDO]-3-LOWER ALKANOYLOXYMETHYL OR HETEROCYCLICTHIOMETHYL-3-CEPHEM-4-CARBOXYLIC ACID COMPOUNDS

[75] Inventors: Takao Takaya, Kawanishi; Takashi Masugi, Toyonaka; Hisashi Takasugi, Osaka; Hiromu Kochi, Sakai, all of Japan

[73] Assignee: Fujisawa Pharmaceutical Co., Ltd., Osaka, Japan

[21] Appl. No.: 123,164

[22] Filed: Feb. 20, 1980

Related U.S. Application Data

[63] Continuation-in-part of Ser. No. 877,848, Feb. 15, 1978, which is a continuation-in-part of Ser. No. 767,700, Feb. 11, 1977, Pat. No. 4,166,115.

[30] Foreign Application Priority Data

Oct. 19, 1976 [JP]  Japan .................................. 51/125826
Apr. 12, 1976 [GB]  United Kingdom ............... 14916/76
Jun. 7, 1976 [GB]  United Kingdom ............... 23490/76

[51] Int. Cl.$^3$ .................. A61K 31/545; C07D 501/56
[52] U.S. Cl. ......................................... 424/246; 544/27; 544/28; 548/194
[58] Field of Search ........................... 424/246; 544/27

[56]  References Cited

U.S. PATENT DOCUMENTS

| | | | |
|---|---|---|---|
| 4,092,477 | 5/1978 | Cook et al. | 544/26 |
| 4,098,888 | 7/1978 | Ochiai et al. | 424/246 |
| 4,152,432 | 5/1979 | Heymes et al. | 424/246 |
| 4,166,115 | 8/1979 | Takaya et al. | 424/246 |

Primary Examiner—Paul M. Coughlan, Jr.
Attorney, Agent, or Firm—Dayton R. Stemple

[57]  ABSTRACT

Syn isomers of 3-substituted 7-[2-substituted imino-2-substituted acetamido]-3-cephem-4-carboxylic acid and salt bacteriostatic-compounds and pharmaceutical compositions thereof and processes for preparing same.

4 Claims, No Drawings

SYN ISOMER OF 7-[2-CYCLO(LOWER) ALKOXYIMINO-2-(2-AMINO-OR SUBSTITUTED AMINOTHIAZOL-4-yl)ACETAMIDO]-3-LOWER ALKANOYLOXYMETHYL OR HETEROCYCLICTHIOMETHYL-3-CEPHEM-4-CARBOXYLIC ACID COMPOUNDS

This application is a continuation-in-part of copending application Ser. No. 877,848, Feb. 15, 1978, which in turn was a continuation-in-part of copending application Ser. No. 767,700, Feb. 11, 1977, now U.S. Pat. No. 4,166,115.

The present invention relates to new syn-isomer of 3,7-disubstituted-3-cephem-4-carboxylic acid compounds and pharmaceutically acceptable salts thereof. More particularly, it relates to new syn-isomer of 3,7-disubstituted-3-cephem-4-carboxylic acid compounds and pharmaceutically acceptable salts thereof which have antibacterial activities and to processes for the preparation thereof, to pharmaceutical composition comprising the same, and to a method of using the same therapeutically in the treatment of infectious diseases in human being and animals.

Accordingly, it is one object of the present invention to provide syn-isomer of 3,7-disubstituted-3-cephem-4-carboxylic acid compounds and pharmaceutically acceptable salts thereof, which are highly active against a number of pathogenic bacteria.

Another object of the present invention is to provide processes for the preparation of syn-isomer of 3,7-disubstituted-3-cephem-4-carboxylic acid compounds and pharmaceutically acceptable salts thereof.

A further object of the present invention is to provide pharmaceutical composition comprising, as active ingredients, said syn-isomer of 3,7-disubstituted-3-cephem-4-carboxylic acid compounds and pharmaceutically acceptable salts thereof.

Still further object of the present invention is to provide a method for the treatment of infectious diseases caused by pathogenic bacteria in human being and animals.

The object syn-isomer of 3,7-disubstituted-3-cephem-4-carboxylic acid compounds are novel and can be represented by the following formula (I):

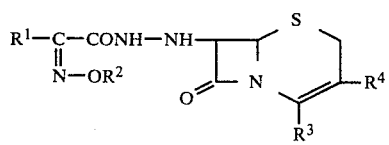
(I)

in which
$R^1$ is a group of the formula:

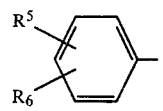

wherein $R^5$ is hydrogen, halogen, nitro, hydroxy, lower alkoxy or acyloxy and $R^6$ is hydroxy, lower alkoxy, acyloxy, acylamino or di(lower)alkylamino;
a group of the formula:

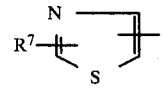

wherein $R^7$ is amino, protected amino, hydroxy or lower alkyl; or
a group of the formula:

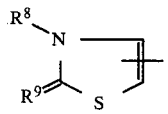

wherein $R^8$ is lower alkyl and $R^9$ is imino, protected imino or oxo;
$R^2$ is an aliphatic hydrocarbon group which may have suitable substituent(s);
$R^3$ is carboxy or protected carboxy; and
$R^4$ is acyloxymethyl, hydroxymethyl, formyl or a heterocyclicthiomethyl group which may have suitable substituent(s); or $R^3$ and $Rhu 4$ are linked together to form —COOCH$_2$—.

With regard to the present invention, it is to be noted that this invention is characterized by providing syn-isomer of 3,7-disubstituted-3-cephem-4-carboxylic acid compounds, which is represented by the formula (I), and the said syn-isomer can be represented by the partial structure of the formula:

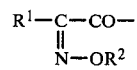

in their molecules, while the corresponding anti-isomer is represented by the partial structure of the formula:

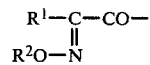

Accordingly, in the following detailed explanations of this invention in this specification and claims, it is to be understood that the syn-isomers of the object compounds as well as the starting compounds of this invention are represented by the partial structure of the formula:

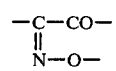

in their molecules, provided that, in case that it is convenient for the explanation of this invention to express both of the syn-isomer and anti-isomer by one general formula, they are represented by the partial structure of the formula:

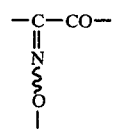

The object compounds of the present invention (I) are novel compounds and can be prepared by the Processes 1 to 8 as mentioned below.

Process 1

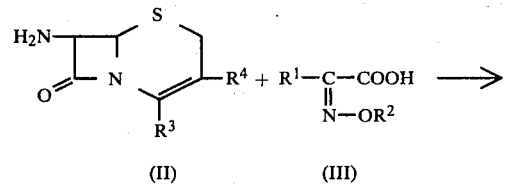

(II)  (III)

or its reactive derivative at the amino group or a salt thereof or its reactive derivative at the carboxy group or a salt thereof

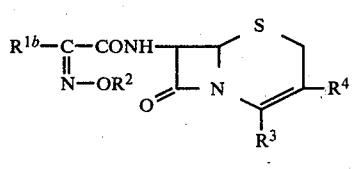

(I)

or a salt thereof

Process 2

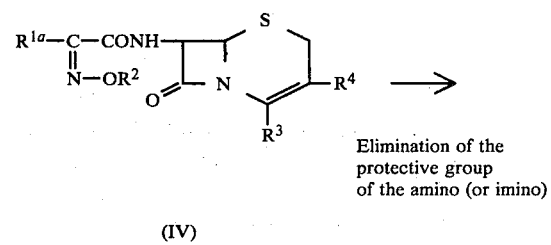

(IV)

or a salt thereof

Elimination of the protective group of the amino (or imino)

(Iₐ)

or a salt thereof

Process 3

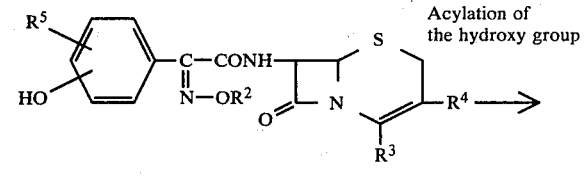

(V)

or a salt thereof

Acylation of the hydroxy group

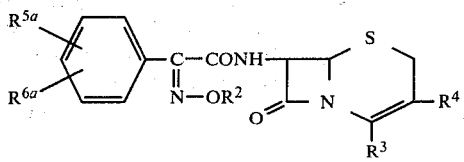

(I_b)

or a salt thereof

Process 4

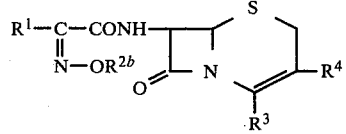

(Vₐ)

or a salt thereof

Elimination of the protective group of the carboxy (I_c)

or a salt thereof

Process 5

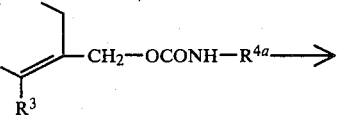

(V_b)

or a salt thereof

Elimination of the protective group of the amino (I_d)

or a salt thereof

Process 6

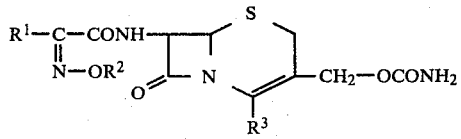

(V_c)    (V_d)

or a salt thereof

or its reactive derivative at the mercapto group

-continued

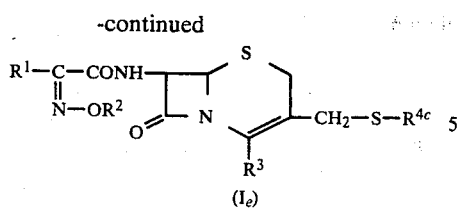
(I$_e$)

or a salt thereof

Process 7

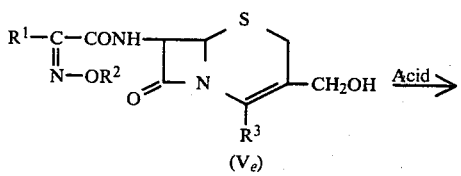 Acid⟶

(V$_e$)

or a salt thereof

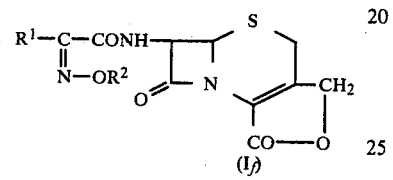
(I$_f$)

or a salt thereof

Process 8

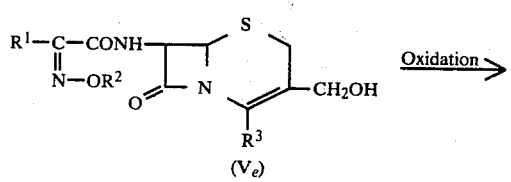 Oxidation⟶

(V$_e$)

or a salt thereof

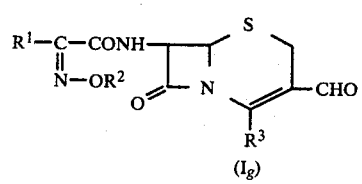
(I$_g$)

or a salt thereof wherein
R$^1$, R$^2$, R$^3$, R$^4$ and R$^5$ are each as defined above;
R$^{1a}$ is a group of the formula:

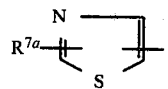

in which R$^{7a}$ is protected amino; or
a group of the formula

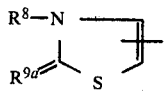

in which R$^8$ is as defined above and R$^{9a}$ is protected imino;
R$^{1b}$ is a group of the formula:

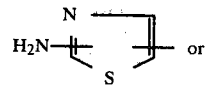 or a group of the formula:

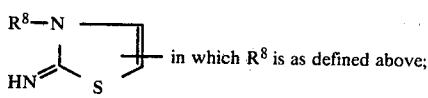 in which R$^8$ is as defined above;

in which R$^8$ is as defined above;
R$^{5a}$ is hydrogen, halogen, nitro, lower alkoxy or acyloxy;
R$^{6a}$ is acyloxy;
R$^{2a}$ is protected carboxy(lower)alkyl;
R$^{2b}$ is carboxy(lower)alkyl;
R$^{4a}$ is a protective group of amino;
R$^{4b}$ is a group which can be substituted by a group R$^{4c}$—S— wherein R$^{4c}$ is a heterocyclic group which may have suitable substituent(s); and
R$^{4c}$ is as defined above.

Among the starting compounds, the starting compound (III), including the corresponding anti-isomer are novel and can be prepared by the processes which are illustrated by the following scheme.

(1) (i)

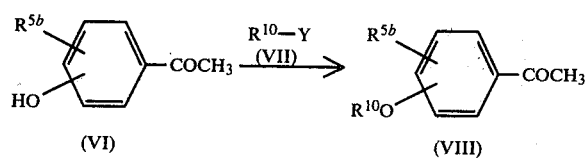
(VI) (VIII)

(ii)

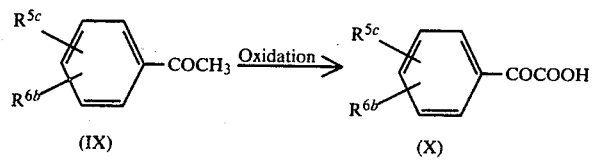
(IX) (X)

-continued
(iii)
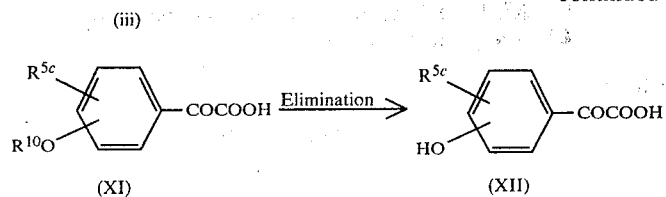
(iv)
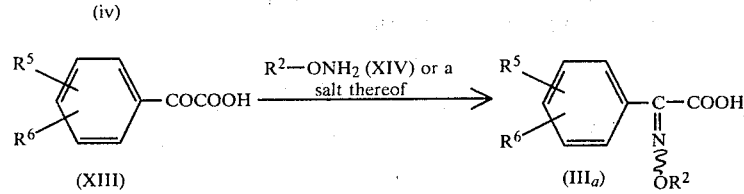
(2) (i)
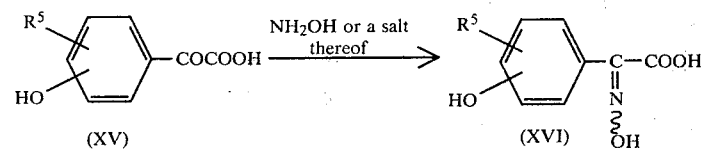
(ii)
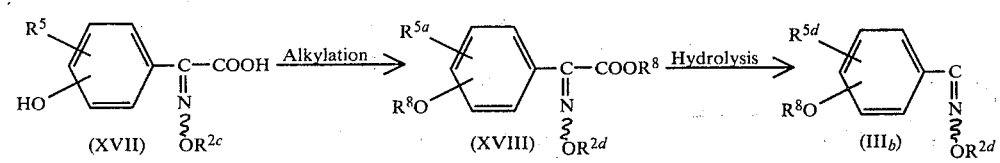
(3)
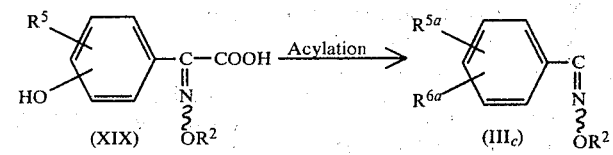
(4) (i)
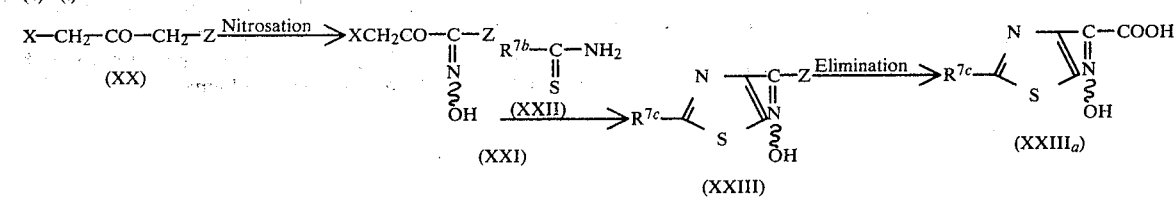
(ii)
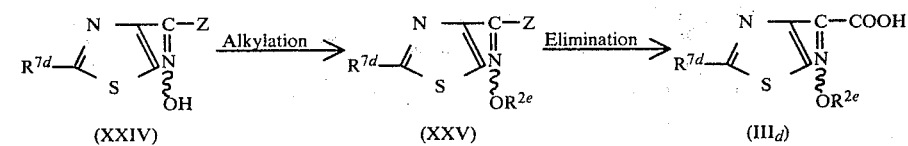
(5)
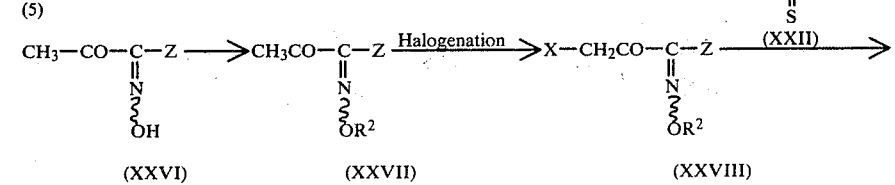

-continued
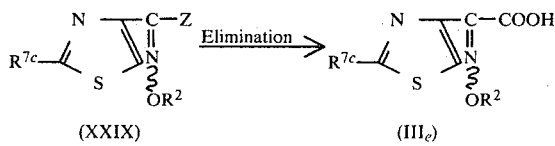
(6) (i)
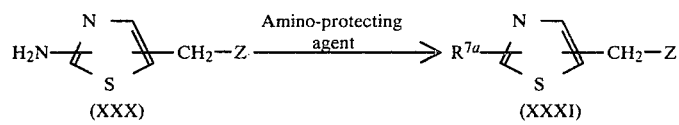
(ii)
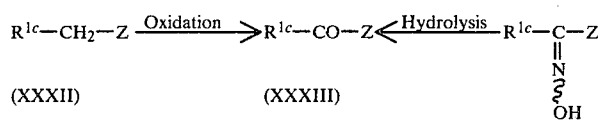
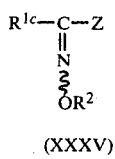
(iii)
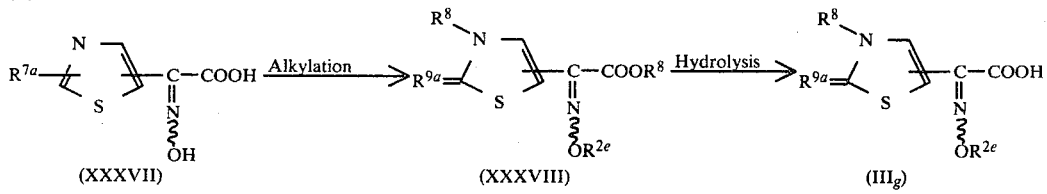
(7)
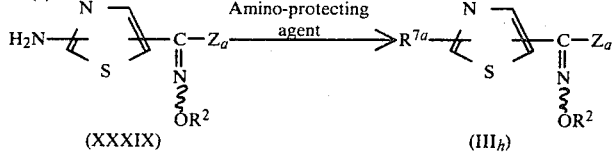
in which
$R^2$, $R^5$, $R^6$, $R^{5a}$, $R^{6a}$, $R^{7a}$, $R^8$ and $R^{9a}$ are each as defined above;
$R^{5b}$ is halogen;
Y is an acid residue;
$R^{10}$ is ar(lower)alkyl;

$R^{5c}$ is hydrogen, halogen or nitro;
$R^{6b}$ is lower alkoxy, ar(lower)alkoxy or acylamino;
$R^{2c}$ is hydrogen, lower alkyl or lower alkenyl;
$R^{5d}$ is hydrogen, halogen, nitro, hydroxy or lower alkoxy;
X is halogen;
Z is protected carboxy;
$R^{7b}$ is lower alkyl, amino or lower alkoxy;
$R^{7c}$ is lower alkyl, amino or hydroxy;
$R^{7d}$ is lower alkyl;
$R^{2e}$ is lower alkyl;
$R^{1c}$ is a group of the formula:

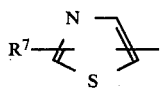

in which $R^7$ is as defined above, or a group of the formula:

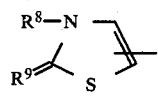

in which $R^8$ and $R^9$ are each as defined above;
$R^{2d}$ is lower alkyl or lower alkenyl; and
$Z_a$ is carboxy or protected carboxy.

The other starting compounds (IV), (V), $(V_a)$–$(V_c)$ and $(V_e)$ are all novel compounds and can be prepared by the aforesaid Processes 1 to 8.

Regarding the object compounds of the formulae (I), $(I_a)$ and $(I_c)$–$(I_g)$, and the starting compounds of the formulae (III), $(III_e)$, $(III_f)$, $(III_h)$, (IV), $(V_a)$–$(V_c)$, $(V_e)$, (XXIII)–$(XXIII_b)$, (XXIX)–(XXXVII) and (XXXIX), it is to be understood that said object and starting compounds include tautomeric isomers relating to their thiazole groups. That is, in case that the group represented by the formula:

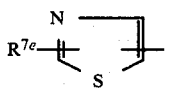

(wherein $R^{7e}$ is amino, protected amino or hydroxy) in the formula of said object and starting compounds take the formula:

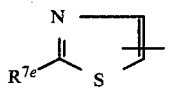 (A)

($R^{7e}$ is as defined above), said group of the formula:

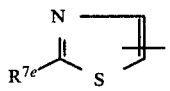

can be also alternatively represented by its tautomeric formula:

 (B)

(wherein $R^{7f}$ is imino, protected imino or oxo). That is, both of the said groups (A) and (B) are in the state of equilibrium as so-called tautomeric forms which can be represented by the following equilibrium:

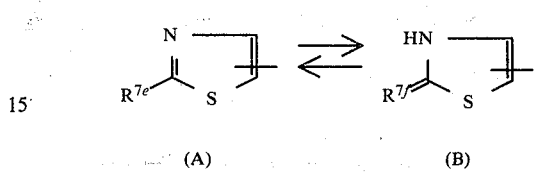

(A)        (B)

(wherein $R^{7e}$ and $R^{7f}$ are each as defined above).

These types of tautomerism between 2-amino- and 2-hydroxythiazole compounds and 2-imino- or 2-oxothiazoline compounds as stated above have been well known in the literature, and it is obvious to a person skilled in arts that both of the tautomeric isomers are equilibrated and easily convertible reciprocally, and accordingly it is to be understood that such isomers are included within the same category of the compound per se. Accordingly, the both of the tautomeric forms of the object compounds (I), $(I_a)$ and $(I_c)$–$(I_g)$, and the starting compounds (III), $(III_e)$, $(III_f)$, $(III_h)$, (IV), $(V_a)$–$(V_c)$, $(V_e)$, (XXIII)–$(XXIII_b)$, (XXIX)–(XXXVII) and (XXXIX) are clearly included within the scope of the present invention. In the present specification, claims and examples, the object and starting compounds including the group of such tautomeric isomers are represented by using one of the expressions therefor, that is the formula:

" 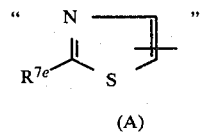 "

(A)

only for the convenient sake.

Furthermore, regarding the object compounds (I), $(I_a)$–$(I_c)$ and $(I_g)$, and the starting compounds (II), (IV), (V) and $(V_a)$, the compounds wherein $R^3$ is carboxy and $R^4$ is formyl can be also regarded as substantially same compounds as the compounds wherein $R^3$ and $R^4$ are linked together to form a group of the formula: —COOCH(OH)—, i.e. so-called intramolecular hemiacylal type compounds, and accordingly both of them are understood to be included within the same category of the compound per se and therefore within the scope of the present invention.

Suitable pharmaceutically acceptable salt of the object syn-isomer of 3,7-disubstituted-3-cephem-4-carboxylic acid compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc., an organic salt, for example, an organic amine salt (e.g., trimethylamine salt, triethylamine salt, ethanolamine salt, diethanolamine salt, pyridine salt, picoline salt, dicyclohexylamine salt, N,N'-dibenzylethylenediamine salt, etc.) etc., an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention intend to include within the scope thereof are explained in details as follows.

The term "lower" is intended to mean 1 to 6 carbon atom(s), unless otherwise provided.

Aliphatic hydrocarbon group is intended to mean straight branched or cyclic aliphatic hydrocarbon having 1 to 6 carbon atom(s) and may include lower alkyl, cyclo(lower)alkyl, lower alkenyl, lower alkynyl and the like. And said aliphatic hydrocarbon group may have 1 to 2 suitable substituent(s) such as carboxy, protected carboxy, arylthio, lower alkylthio, aryl, acyloxy, lower alkoxy, aryloxy, a heterocyclic or the like.

Suitable cyclo(lower)alkyl is one having 3 to 6 carbon atoms and may include cyclopropyl, cyclobutyl, cyclopentyl, cyclohexyl and the like, and preferably one having 5 to 6 carbon atoms.

Suitable lower alkynyl is one having 2 to 6 carbon atoms and may include ethynyl, 2-propynyl, 2-butynyl, 3-pentynyl, 3-hexynyl and the like, and preferably one having 2 to 4 carbon atoms, and more preferably one having 2 to 3 carbon atoms.

Suitable halogen may include chlorine, bromine, fluorine and iodine.

Suitable lower alkoxy and lower alkoxy moiety in the term "ar(lower)alkoxy" may include one which may be branched, for example, methoxy, ethoxy, propoxy, isopropoxy, butoxy, isobutoxy, tert-butoxy, pentyloxy, hexyloxy and the like, and preferably one having 1 to 4 carbon atom(s), and more preferably one having 1 to 2 carbon atom(s).

Suitable protected amino may include an acylamino and amino group substituted by a conventional protective group other than the acyl group such as benzyl or the like.

Suitable lower alkyl and lower alkyl moiety in the terms "lower alkylthio", "carboxy(lower)alkyl", "protected carboxy(lower)alkyl", "ar(lower)alkyl" and "di(lower)alkylamino" may include one which may be branched, for example, methyl, ethyl, propyl, isopropyl, butyl, isobutyl, tert-butyl, pentyl, hexyl and the like, wherein lower alkyl moiety may preferably be one having 1 to 4 carbon atom(s), and more preferably one having 1 to 2 carbon atom(s).

Suitable protected imino may include an acylimino and imino group substituted by a conventional protective group other than the acyl group such as benzyl and the like.

Suitable protected carboxy and protected carboxy moiety in the term "protected carboxy(lower)alkyl" may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.), wherein lower alkyl moiety may be preferably one having 1 to 4 carbon atom(s); lower alkenyl ester (e.g., vinyl ester, allyl ester etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester etc.);

ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);

aryl ester which may have one or more suitable substituent(s) (e.g., phenyl ester, tolyl ester, tertiarybutylphenyl ester, xylyl ester, mesityl ester, cumenyl ester, etc.), and the like. Preferable example of protected carboxy may be lower alkoxycarbonyl (e.g., methoxycarbonyl, ethoxycarbonyl, propoxycarbonyl, butoxycarbonyl, t-butoxycarbonyl, t-pentyloxycarbonyl, hexyloxycarbonyl, etc.) having 2 to 7 carbon atoms, preferably one having 2 to 5 carbon atoms.

Suitable aryl and aryl moiety in the terms "ar(lower)alkyl", "ar(lower)alkoxy", "arylthio" and "aryloxy" may include phenyl, tolyl, xylyl, mesityl, cumenyl, naphthyl and the like, wherein said aryl group may have 1 to 3 suitable substituent(s) such as halogen (e.g., chlorine, bromine, iodine or fluorine), hydroxy, and the like.

Suitable heterocyclic group and heterocyclic moiety in the term "a heterocyclicthiomethyl group which may have suitable substituent(s)" means saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (preferably 5 to 6 membered) heteromonocyclic group containing 1 to 4 nitrogen atom(s), for example, pyrrolyl, pyrrolinyl, imidazolyl, pyrazolyl, pyridyl and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc; saturated 3 to 8-membered (preferably 5 to 6 membered) heteromonocyclic group containing 1 to 4 nitrogen atom(s), for example, pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3- to 8-membered (preferably 5 to 6 membered) heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.;

saturated 3 to 8-membered (preferably 5 to 6 membered) heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (preferably 5 to 6 membered) heteromonocyclic group containing 1 to 2 sulfur atom(s) and 1 to 3 nitrogen atom(s), for example, thiazolyl, thiadiazolyl (e.g., 1,2,4-thiadiazolyl, 1,3,4-thiadiazolyl, 1,2,5-thiadiazolyl, etc.), etc;

saturated 3 to 8-membered (preferably 5 to 6 membered) heteromonocyclic group containing 1 to 2 sulfur atom(s) and 1 to 3 nitrogen atom(s), for example, thiazolidinyl, etc.;

unsaturated 3 to 8 membered (preferably 5 to 6 membered) heteromonocyclic group containing a sulfur atom, for example, thienyl, etc.;

unsaturated condensed heterocyclic group containing 1 to 2 sulfur atom(s) and 1 to 3 nitrogen atom(s), for example, benzothiazolyl, benzothiadiazolyl, etc. and the like;

wherein said heterocyclic group may have 1 to 2 suitable substituent(s) such as lower alkyl (e.g., methyl, ethyl, propyl, isopropyl, butyl, isobutyl, pentyl, cyclopentyl, hexyl, cyclohexyl, etc.), preferably one having 1 to 4 carbon atom(s); lower alkenyl (e.g., vinyl, allyl, butenyl, etc.);

aryl (e.g., phenyl, tolyl, etc.); halogen (e.g., chlorine, bromine, iodine or fluorine); amino; di(lower)alkylamino(lower)alkyl (e.g. dimethylaminomethyl, dimethylaminoethyl, diethylaminopropyl, diethylaminobutyl, etc.), preferably one having 3 to 6 carbon atoms; or the like.

Suitable lower alkenyl is one having 2 to 6 carbon atoms and may include, for example, vinyl, allyl, isopropenyl, 1-propenyl, 2-butenyl, 3-pentenyl and the like, and preferably one having 2 to 4 carbon atoms.

Suitable acyl moiety in the terms "acylamino", "acylimino", "acyloxy" and "acyloxymethyl" as mentioned above may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s);

lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms;

lower alkanesulfonyl (e.g., mesyl, ethanesulfonyl, propanesulfonyl, isopropanesulfonyl, butanesulfonyl, etc.), preferably one having 1 to 4 carbon atom(s), more preferably one having 1 to 2 carbon atom(s);

arenesulfonyl (e.g., benzenesulfonyl, tosyl, etc.); aroyl (e.g., benzoyl, toluoyl, naphthoyl, phthaloyl, indancarbonyl, etc.);

ar(lower)alkanoyl (e.g., phenylacetyl, phenylpropionyl, etc.); ar(lower)alkoxycarbonyl (e.g, benzyloxycarbonyl, phenethyloxycarbonyl, etc.); and the like.

The acyl moiety as stated above may have 1 to 3 suitable substituent(s) such as halogen (e.g. chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl etc.), acyl such as halo(lower)alkanoyl (e.g., chloroacetyl, dichloroacetyl, trichloroacetyl, trifluoroacetyl, etc.), aryl (e.g., phenyl, tolyl, etc.), or the like. Suitable examples of the acyl having said substituent(s) may be mono(or di or tri)halo(lower)alkanoyl (e.g., trifluoroacetyl, trichloroacetyl, etc.), preferably one having 2 to 4 carbon atoms;

mono(or di or tri)halo(lower)alkanoylcarbamoyl (e.g., trichloroacetylcarbamoyl, etc.), preferably one having 3 to 4 carbon atoms; or the like.

Suitable protective group of amino for $R^{4a}$ may include acyl such as halo(lower)alkanoyl (e.g., chloroacetyl, dichloroacetyl, trichloroacetyl, trifluoroacetyl, etc.), preferably one having 2 to 3 carbon atoms, or the like.

Suitable acid residue may include a residue of an acid such as an inorganic acid (e.g., hydrochloric acid, hydrobromic acid, hydriodic acid, sulfuric acid, etc.) or an organic acid (e.g., methanesulfonic acid, benzenesulfonic acid, p-toluenesulfonic acid, etc.).

Suitable example of a group which can be substituted by a group $R^{4c}$—S— may include an acid residue such as halogen, azido or acyloxy wherein said halogen and acyl moiety of said acyloxy are the same ones as aforementioned.

Among the suitable examples of each of the groups of the object compounds as explained and illustrated above, the prefered examples thereof are illustrated as follows.

Preferable example of $R^5$ may be hydrogen halogen (preferably chlorine) or nitro;

preferable example of $R^6$ may be hydroxy, lower alkoxy (preferably $C_1$-$C_4$, more preferably $C_1$-$C_2$), acyloxy[preferably lower alkanoyloxy (preferably $C_1$-$C_4$, more preferably $C_1$-$C_2$) or carbamoyloxy], acylamino [preferably lower alkanesulfonylamino (preferably $C_1$-$C_4$, more preferably ($C_1$-$C_2$)] or di(lower)alkylamino (wherein the alkyl moiety is preferably $C_1$-$C_4$, more preferably $C_1$-$C_2$);

preferable example of $R^7$ may be amino, protected amino such as acylamino [preferably lower alkanesulfonylamino (preferably $C_1$-$C_4$, more preferably $C_1$-$C_2$), trihalo(lower)alkanoylamino (preferably $C_1$-$C_4$, more preferably $C_1$-$C_2$) lower alkoxycarbonylamino (preferably $C_2$-$C_7$, more preferably $C_3$-$C_6$) or lower alkanoylamino (preferably $C_1$-$C_4$, more preferably $C_1$-$C_2$)], hydroxy or lower alkyl (preferably $C_1$-$C_4$, more preferably $C_1$-$C_2$);

preferable example of $R^8$ is $C_1$-$C_4$ lower alkyl, more preferably $C_1$-$C_2$ lower alkyl;

preferable example of $R^9$ may be protected imino such as acylimino [preferably lower alkanesulfonylimino (preferably $C_1$-$C_4$, more preferably $C_1$-$C_2$)];

preferable example of $R^2$ may be lower alkyl (preferably $C_2$-$C_6$), cyclo(lower)alkyl, lower alkenyl, lower alkynyl, ar(lower)alkenyl [more preferably phenyl(lower)alkenyl], carboxy(lower)alkyl, protected carboxy(lower)alkyl [more preferably lower alkoxycarbonyl (preferably $C_3$-$C_6$) (lower)alkyl], arylthio(lower)alkyl [more preferably phenylthio(lower)alkyl], ar(lower)alkyl [more preferably phenyl(lower)alkyl] which may have halogen (preferably bromine) and hydroxy, thienyl(lower)alkyl or aryloxy(lower)alkyl [more preferably phenoxy(lower)alkyl] which may have hydroxy, in which alkenyl and alkenyl moiety is $C_2$-$C_6$, preferably $C_2$-$C_4$, and alkyl moiety is preferably $C_1$-$C_4$, more preferably $C_1$-$C_2$;

preferable example of $R^3$ may be carboxy;

preferable example of $R^4$ may be acyloxymethyl [preferably lower alkanoyloxymethyl (in which alkanoyl moiety is preferably $C_1$-$C_4$, more preferably $C_1$-$C_2$, most preferably $C_2$, i.e. acetyl) or carbamoyloxymethyl which may have trihalo(lower)alkanoyl (in which trihalo moiety is preferably trichloro and alkanoyl moiety is preferably $C_2$-$C_3$)], hydroxymethyl, formyl, tetrazolylthiomethyl which may have lower alkyl (preferably $C_1$-$C_4$, more preferably $C_1$-$C_2$) or di(lower)alkylamino(lower)alkyl (in which alkyl moiety is preferably $C_1$-$C_4$, more preferably $C_1$-$C_2$), triazolylthiomethyl which may have lower alkyl (preferably $C_1$-$C_4$, more preferably $C_1$-$C_2$) or thiadiazolylthiomethyl which may have lower alkyl (preferably $C_1$-$C_4$, more preferably $C_1$-$C_2$); or $R^3$ and $R^4$ are linked together to form —COOCH$_2$—.

The various processes for preparing the object compounds of the present invention are explained in details in the following.

Process 1:

The object compound (I) or a salt thereof can be prepared by reacting the compound (II) or its reactive derivative at the amino group or a salt thereof with the compound (III) or its reactive derivative at the carboxy group or a salt thereof, which is a fundamental method for preparing the object compound (I).

Suitable reactive derivative at the amino group of the compound (II) may include conventional reactive derivative used in amidation, for example, a silyl derivative formed by the reaction of the compound (II) with a silyl compound such as bis(trimethylsilyl)acetamide, trimethylsilylacetamide or the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a salt with an inorganic base such as an alkali metal salt (e.g., sodium salt, potassium salt, etc.), an alkaline earth metal salt (e.g., calcium salt, magnesium salt, etc.) or ammonium salt; a salt with an organic base (e.g., triethylamine salt, pyridine salt, etc.); and the like.

Suitable reactive derivative at the carboxy group of the compound (III) may include conventional one used in amidation.

The salts of the compound (III) may be salts with an inorganic base such as an alkali metal salts (e.g., sodium or potassium salt), or an alkaline earth metal salt (e.g., calcium or magnesium salt), a salt with an organic base such as trimethylamine, triethylamine, pyridine, a salt with an acid (e.g., hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

The present reaction is preferably carried out in the presence of a condensing agent such as so-called Vilsmeier reagent, for example, (chloromethylene)-dimethylammonium chloride produced by the reaction of dimethylformamide with thionyl chloride or phosgene, a compound produced by the reaction of dimethylformamide with phosphorus oxychloride, etc., or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorphorine, N,N-di(-lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, it is to be noted that, in case that the starting compound (III) is reacted with the compound (II) or its reactive derivative at the amino group or a salt thereof in the presence of, for example, phosphorus pentachloride, thionyl chloride, etc., only the corresponding anti-isomer to the object compound (I) or a mixture of the corresponding anti-isomer and syn-isomer is always given as an object compound even if the compound (III), i.e., syn-isomer is used as a starting compound. It is of course to be noted that the reaction of the corresponding anti-isomer to the starting compound (III) with the compound (II) can never produce the object compound (I) of the present invention, i.e. syn-isomer. It may be understood that such tendency and singularity of the reaction as mentioned above is due to the fact that the less stable syn-isomer tends to isomerize partially or wholly to the corresponding more stable anti-isomer in the course of the reaction, for example, in so-called activation step of the compound (III) so that the isomerized compound, i.e. the anti-isomer corresponding to the object compound (I) can be produced as an object compound.

Accordingly, in order to obtain the object compound (I), i.e., syn-isomer selectively and in high yield, it is necessary to use the starting compound (III), i.e., syn-isomer and to select a suitable reaction condition. That is, the object compound (I), i.e., syn-isomer can be obtained selectively and in high yield by conducting the reaction, for example, in the presence of a Vilsmeier reagent as mentioned above etc. and under around neutral condition.

Especially, in case that the starting compound (III) wherein $R^1$ is a group of the formula:

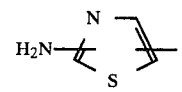

is used, the object compound (I), i.e., syn-isomer can be obtained selectively and in high yield by conducting the present reaction of the corresponding starting compound (III), i.e., syn-isomer with the compound (II), for example, in the presence of a Vilsmeier reagent produced by the reaction of dimethylformamide with phosphorus oxychloride and under around neutral condition. And, in this case, it is to be noted that particularly good results can be achieved by conducting the reaction in the presence of more than two molar equivalents of phosphorus oxychloride to each amount of the said starting compound (III), i.e., syn-isomer and dimethylformamide as shown in the working examples. Further, in this case, it is to be also noted that good results can be achieved by conducting an activation step of the starting compound (III), i.e., syn-isomer in the presence of a silyl compound [e.g. bis(trimethylsilyl)acetamide, trimethylsilylacetamide, etc.] and the like.

With regard to the reaction of the compound (II) with the compound (III), it is to be noted that;

when the compound (II) wherein $R^4$ is carbamoyloxymethyl group having acyl group is used as a starting compound, there may be obtained occasionally either the object compound (I) wherein $R^4$ is carbamoyloxymethyl group having acyl group or free carbamoyloxymethyl group according to reaction conditions;

when the compound (II) wherein $R^4$ is hydroxymethyl group is used as a starting compound, there may be obtained occasionally the object compound (I) wherein $R^3$ and $R^4$ are linked together to form —COOCH$_2$—;

and further the protected carboxy group or salts in the compound (II) may be converted into free carboxy group; in the course of the reaction or in post-treatment. These cases are also included within the scope of the present invention.

As clear from the explanation as stated above, it is to be understood that the Process 1 is a fundamental and the most advantageous method for preparing the object compound (I), i.e. syn-isomer.

Process 2:

The object compound ($I_a$) or a salt thereof can be prepared by subjecting the compound (IV) or a salt thereof to elimination reaction of the protective group of the amino or imino.

Suitable salt of the compound (IV) may include a metal salt, ammonium salt, an organic amine salt and the like as aforementioned.

The present elimination reaction is carried out in accordance with a conventional method such as hydrolysis; reduction; a method by reacting the compound (IV) wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective groups such as substituted or unsubstituted alkoxycarbonyl (e.g., t-pentyloxycarbonyl, etc.), alkanoyl (e.g., formyl, etc.), cycloalkoxycarbonyl, substituted or unsubstituted aralkoxycarbonyl (e.g., benzyloxycarbonyl, substituted benzyloxycarbonyl, etc.), substituted phenylthio, substituted aralkylidene, substituted alkylidene, substituted cycloalkylidene, or the like. Suitable acid may include an organic or an inorganic acid, for example, formic acid, trifluoroacetic acid, benzenesulfonic acid, p-toluenesulfonic acid, hydrochloric acid and the like, and preferable acid is an acid which can be easily removed from the reaction mixture by a conventional manner such as distillation under reduced pressure, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include an organic solvent, water or a mixed solvent thereof. When trifluoroacetic acid is used, the elimination rection may be preferably carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g., trifluoroacetyl, etc.) etc. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Among the protective groups, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g., trichloroethoxycarbonyl etc.), substituted or unsubstituted aralkoxycarbonyl (e.g., benzyloxycarbonyl, substituted benzyloxycarbonyl etc.), 2-pyridylmethoxycarbonyl, etc. Suitable reduction may include, for example, reduction with an alkali metal borohydride (e.g., sodium borohydride, etc.) and the like.

Suitable iminohalogenating agent used in a method as mentioned above may include phosphorus trichloride, phosphorus pentachloride, phosphorus tribromide, phosphorus pentabromide, phosphorus oxychloride, thionyl chloride, phosgene and the like. The reaction temperature is not critical, and the reaction is usually carried out at ambient temperature or under cooling. Suitable iminoetherifying agent reacted with thus obtained reaction product may include an alcohol, metal alkoxide and the like. Suitable alcohol may include alkanol (e.g., methanol, ethanol, propanol, isopropanol, butanol, t-butanol, etc.) which may be substituted with alkoxy (e.g., methoxy, ethoxy, propoxy, isopropoxy, butoxy, etc.). Suitable metal alkoxide may include alkali metal alkoxide (e.g., sodium alkoxide, potassium alkoxide, etc.), alkaline earth metal alkoxide (e.g., calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can be readily carried out by pouring the reaction mixture obtained above into water, but there may be previously added a hydrophilic solvent (e.g., methanol, ethanol, etc.), a base (e.g., alkali metal bicarbonate, trialkylamine, etc.) or an acid (e.g., diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the cases that the protected carboxy is transformed into the free carboxy group; that when the compound (IV) wherein $R^4$ is carbamoyloxymethyl group having acyl group is used as the starting compound, there may be obtained occasionally either the object compound ($I_a$) wherein $R^4$ is carbamoyloxymethyl group having acyl group or free carbamoyloxymethyl group according to reaction conditions; and that when the compound (IV) wherein $R^4$ is acyloxymethyl group is used as the starting compound, there may be obtained occasionally the object compound ($I_a$) wherein $R^3$ and $R^4$ are linked together to form $-COOCH_2-$ according to reaction conditions; in the course of the reaction or in post-treatment.

Process 3:

The object compound ($I_b$) or a salt thereof can be prepared by acylating the hydroxy group of the compound (V) or a salt thereof.

Suitable salt of the compound (V) can also be referred to the ones exemplified for the compound (IV).

The acylating agent to be used for the present reaction may include an aliphatic, aromatic and heterocyclic carboxylic acid, and the corresponding sulfonic acid and thio acid which have aforesaid acyl group as their acyl moieties, and reactive derivatives of the above-mentioned acids. Suitable reactive derivative of the above-mentioned acids may include an acid halide, an acid anhydride, an activated amide, an activated ester, and the like. Suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester [e.g., cyanomethyl ester, methoxymethyl ester, dimethyliminomethyl (($CH_3)_2N^+=CH-$) ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester], or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the acylating agent to be used.

The acylating agent may further include aliphatic, aromatic or heterocyclic isocyanate or isothiocyanate (e.g., methyl isocyanate, phenyl isocyanate, trichloroacetyl isocyanate, methyl isothiocyanate, etc.) and haloformate (e.g., ethyl chloroformate, benzyl chloroformate, etc.). In this case, for example, when trichloroacetyl isocyanate is used as an acylating agent, trichloroacetylcarbamoyl group is introduced as acyl group and said group may be converted to carbamoyl group by treating with base, and when ethyl chloroformate is used as an acylating agent, ethoxycarbonyl group is introduced as acyl group.

The present reaction is carried out according to similar reaction conditions to those of aforesaid reaction of the compound (II) with the compound (III), and is preferably carried out in the presence of a base. In the reaction of the compound (V) with an acylating agent, the protected carboxy group or salts in the compound (V) may be converted into free carboxy group in the course of the reaction or in post-treatment; and when the compound (V) wherein $R^4$ is carbamoyloxymethyl group having acyl group is used as the starting compound, there may be obtained occasionally either the object compound ($I_b$) wherein $R^4$ is carbamoyloxymethyl group having acyl group or free carbamoyloxymethyl group according to reaction conditions in the course of the reaction or in post-treatment. These cases are also included in the scope of the present invention.

Process 4:

The object compound ($I_c$) or a salt thereof can be prepared by subjecting the compound ($V_a$) or a salt thereof to elimination reaction of the protective group of the carboxy.

Suitable salt of the compound ($V_a$) can be referred to the ones exemplified for the compound (IV).

The present elimination reaction is carried out in accordance with a conventional method such as hydrolysis or the like. The hydrolysis may include a method using an acid or base and the like. These methods may be selected depending on kind of the protective groups to be eliminated.

The hydrolysis using an acid is one of the most common and preferable methods for eliminating the protective groups such as phenyl(lower)alkyl, substituted phenyl(lower)alkyl, lower alkyl, substituted lower alkyl, or the like. Suitable acid may include inorganic or organic acid, for example, formic acid, trifluoroacetic acid, benzenesulfonic acid, p-toluenesulfonic acid, hydrochloric acid, and the like. The present reaction may be carried out in the presence of anisole. The acid suitable for the reaction can be selected according to the protective group to be eliminated and other factors. The hydrolysis using an acid may be carried out in the presence of a solvent, such as an organic solvent, water or a mixed solvent thereof.

The reaction temperature is not critical and may be suitably selected in accordance with the kind of the protective group and the elimination method, and the present reaction is preferably carried out under a mild condition such as under cooling, at ambient temperature or slightly warming.

The present invention includes, within its scope, the cases that the protected carboxy group for $R^3$ is transformed into the free carboxy group; that the protected amino group is transformed into the free amino group; that the protected imino group is transformed into the free imino group; that the acyloxy group is transformed into the hydroxy group; and/or that the carbamoyloxymethyl group having acyl group is transformed into the free carbamoyloxymethyl group; during the reaction or posttreating in the present reaction.

Process 5:

The object compound ($I_d$) or a salt thereof can be prepared by subjecting the compound ($V_b$) or a salt thereof to elimination reaction of the protective group of the amino.

Suitable salt of the compound ($V_b$) can be referred to the ones exemplified for the compound (IV).

The present elimination reaction may include an elimination method using a base, for example, an inorganic base such as an alkali metal hydroxide (e.g., sodium hydroxide, potassium hydroxide, etc.), an alkali metal bicarbonate (e.g., sodium bicarbonate, potassium bicarbonate, etc.) or alkali metal carbonate (e.g., sodium carbonate, potassium carbonate, etc.), an organic base such as an alkali metal alkoxide (e.g., sodium methoxide, sodium ethoxide, etc.), a trialkylamine (e.g., trimethylamine, triethylamine, etc.), triethanolamine, N,N-dimethylaniline, N,N-dimethylbenzylamine, N-methylmorpholine or pyridine; and an elimination reaction using basic alumina, basic ion exchange resin, acid (e.g., trifluoroacetic acid, trifluoroacetic acid.anisole, etc.). The present elimination reaction is usually carried out in water, hydrophilic solvent or a mixture thereof. The reaction temperature is not critical and the reaction is preferably carried out at ambient temperature or under cooling.

The present invention includes, within its scope, the cases that the protected carboxy group or salts in the compound ($V_b$) may be converted into free carboxy group, and that the protected amino and/or imino group may be converted into the free amino and/or imino group, respectively in the course of the reaction or in post-treatment.

Process 6:

The object compound ($I_e$) or a salt thereof can be prepared by reacting the compound ($V_c$) or a salt thereof with the compound ($V_d$) or its reactive derivative at the mercapto group.

Suitable salt of the compound ($V_c$) can be referred to the ones exemplified for the compound (IV).

The suitable reactive derivative at the mercapto group of the compound ($V_d$) may include a metal salt such as alkali metal salts (e.g., sodium salt, potassium salt, etc.) or the like.

The present reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, or any other solvent which does not adversely affect the reaction, preferably in ones having strong polarities. Among the solvents, hydrophilic solvents may be used in a mixture with water. The reaction is preferably carried out in weekly basic or around neutral condition. When the compound ($V_c$) and or the thiol compound ($V_d$) is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming. The reaction product can be isolated from the reaction mixture by conventional methods.

The reaction of the compound ($V_c$) with the compound ($V_d$) includes, within its scope, the cases that the protected carboxy group or salts in the compound ($V_c$) may be converted into free carboxy group; that the protected amino and/or imino group may be converted into free amino and/or imino group; and that the acyloxy group may be converted into hydroxy group; respectively in the course of the reaction or in post-treatment.

Process 7:

The object compound ($I_f$) or a salt thereof can be prepared by treating the compound ($V_e$) or a salt thereof with an acid.

Suitable salt of the compound ($V_e$) can be referred to the ones exemplified for the compound (IV).

Suitable acid to be used in the present reaction may include an inorganic acid (e.g., hydrochloric acid, hydrobromic acid, sulfuric acid, etc.) or an organic acid (e.g., formic acid, acetic acid, etc.).

The present reaction is usually carried out in a solvent such as water, acetone, acetic acid or any other solvent which does not adversely influence the reaction. Among these solvents hydrophilic solvents can be used as a mixture with water.

The reaction temperature is not critical and the reaction is preferably carried out under cooling to warming.

Process 8:

The object compound ($I_g$) or a salt thereof can be prepared by oxidizing the compound ($V_e$) or a salt thereof.

Suitable oxidizing agent used in the present reaction may include Jones reagent being used by a combination of sulfuric acid and chromium trioxide, manganese dioxide, a reagent being used by a combination of dimethylsulfoxide and N,N'-dicyclohexylcarbodiimide etc., and the like.

The present reaction is usually carried out in a solvent such as water, acetone, dimethylformamide or any other solvent which does not adversely affect the reaction. These solvents may be used as a mixture thereof.

The reaction temperature is not critical and the reaction is preferably carried out under cooling or around ambient temperature.

Processes for preparing the starting compound (III) i.e., syn-isomer and anti-isomer thereof used for References are explained in details as follows.

(A) Process of (VI)+(VII)→(VIII) [Scheme (1)(i)]

The compound (VIII) can be prepared by reacting the compound (VI) with the compound (VII).

The present reaction is usually carried out in a solvent such as water, ethanol, acetone, ether, dimethylformamide or any other solvent which does not adversely influence the present reaction. The reaction is preferably carried out in the presence of a base such as an inorganic base or an organic base as aforementioned. The reaction temperature is not critical and the reaction is usually carried out under cooling to under heating of boiling point of the solvent.

(B) Processes of (IX)→(X) [Scheme (1)(ii)] and (XXXII)→(XXXIII) [Scheme (6)(ii)]

The compounds (X) and (XXXIII) can be prepared by oxidizing the compounds (IX) and (XXXII), respectively.

The present oxidation reaction is conducted by a conventional method which is applied for the transformation of so-called activated methylene group into carbonyl group. That is, the present oxidation is conducted by a conventional method such as oxidation by using a conventional oxidizing agent such as selenium dioxide, potassium permanganate or the like. The present oxidation is usually carried out in a solvent which does not adversely influence the reaction, for example, water, dioxane, pyridine, tetrahydrofuran, and the like.

The reaction temperature is not critical and the reaction is preferably carried out under warming to heating.

(C) Process of (XI)→(XII) [Scheme (1) (iii)]

The compound (XII) can be prepared by subjecting the compound (XI) to elimination reaction of the ar(-lower)alkyl group.

The present elimination method may include all conventional methods used in the elimination reaction of the ar(lower)alkyl group, for example, hydrolysis, reduction, etc.

The hydrolysis using acid is one of the most preferable method and the acid to be used may include an inorganic acid (e.g., hydrochloric acid, hydrobromic acid, etc.), an organic acid (e.g., formic acid, acetic acid, trifluoroacetic acid, etc.) and a mixture thereof. The present reaction can be carried out in a solvent such as water, an organic solvent or a mixture thereof or without solvent. The reaction temperature is not critical and the reaction is preferably carried out under warming to heating.

(D) Processes of (XIII)+(XIV)→(IIIa) [Scheme (1) (iv)], (XXXIII)+(XIV)→(XXXV) [Scheme (6) (ii)] and (XXXIV)+(XIV)→(III$f$) [Scheme (6) (ii)]

The compounds (III$_a$), (XXXV) and (III$f$) can be prepared by reacting the compounds (XIII), (XXXIII) and (XXXIV) with the compound (XIV) or a salt thereof, respectively.

Suitable salt of the compound (XIV) may include an inorganic acid salt (e.g., hydrochloride, hydrobromide, sulfate, etc.), an organic acid salt (e.g., acetate, p-toluenesulfonate, etc.) and the like.

The present reaction is usually carried out in a solvent such as water, an alcohol (e.g., methanol, ethanol, etc.), a mixture thereof or any other solvent which does not adversely influence the present reaction.

The present reaction, in case that the compound (XIV) is used in its salt form, is preferably carried out in the presence of a base, for example, an inorganic base such as alkali metal (e.g., sodium, potassium, etc.), alkaline earth metal (e.g., magnesium, calcium, etc.), the hydroxide or carbonate or bicarbonate thereof or the like, and an organic base such as alkali metal alkoxide (e.g., sodium methoxide, sodium ethoxide, etc.), trialkylamine (e.g., trimethylamine, triethylamine, etc.), N,N-dialkylamine (e.g., N,N-dimethylaniline, etc.), N,N-dialkylbenzylamine (e.g., N,N-dimethylbenzylamine, etc.), pyridine or the like.

The reaction temperature is not critical and the reaction is usually carried out under cooling to heating.

In the present reaction, the mixture of syn- and anti-isomers of the compound (III$_a$), (XXXV) or (III$f$) may be obtained according to reaction conditions etc., and in such case, both isomers may be resolved by conventional manners from the mixture. For example, the mixture is firstly esterified and the resulting esters are resolved, for example, by chromatography into each isomer. The resolved each isomer of esters is hydrolyzed by a conventional method to give the corresponding syn- or anti-carboxylic acid.

In order to obtain syn-isomer of the compound (III$_a$), (XXXV) or (III$f$) selectively and in high yield the present reaction is preferably carried out around neutral condition.

(E) Processes of (XV)→(XVI) [Scheme (2) (i)] and (XXXIV)→(XXXVI) [Scheme (6) (ii)]

The compounds (XVI) and (XXXVI) can be prepared by reacting the compounds (XV) and (XXXIV) with hydroxylamine or a salt thereof, respectively.

Suitable salt of hydroxylamine can be referred to the ones exemplified for the compound (XIV).

The reaction conditions of the present reaction can also be referred to the ones exemplified for the processes of (XIII)+(XIV)→(III$_a$), (XXXIII)+(XIV)→(XXXV) and (XXXIV)+(XIV)→(III$f$) as mentioned in aforementioned (D).

(F) Processes of (XVII)→(XVIII) [Scheme (2) (ii)], (XXIV)→(XXV) [Scheme (4) (ii)] (XXVI)→(XXVII) [Scheme (5)] and (XXXVII)→(XXXVIII) [Scheme (6) (iii)]

The compounds (XVIII), (XXV), (XXVII) and (XXXVIII) can be prepared by alkylating the compounds (XVIII), (XXIV), (XXVI) and (XXXVII), respectively.

The alkylating agent to be used in the present alkylation reaction may include di(lower)alkyl sulfate (e.g., dimethyl sulfate, diethyl sulfate, etc.), diazo(lower)alkane (e.g., diazomethane, diazoethane, etc.), lower alkyl halide (e.g., methyl iodide, ethyl iodide, etc.), lower alkyl sulfonate (e.g., methyl p-toluenesulfonate, etc.), and the like.

The reaction using di(lower)alkyl sulfate, lower alkyl halide or lower alkyl sulfonate is usually carried out in a solvent such as water, acetone, ethanol, ether, dimethylformamide or any other solvent which does not adversely influence the reaction.

The present reaction is preferably carried out in the presence of a base such as an inorganic base or an organic base as aforementioned.

The reaction temperature is not critical and the reaction is usually carried out under cooling to heating around boiling point of the solvent.

The reaction using diazoalkane is usually carried out in a solvent such as ether, tetrahydrofuran or the like.

The reaction temperature is not critical and the reaction is usually carried out under cooling or at ambient temperature.

(G) Processes of (XVIII)→(III$_b$) [Scheme (2) (ii)] and (XXXVIII)+(III$_g$) [Scheme (6) (iii)]

The compounds (III$_b$) and (III$_g$) can be prepared by subjecting the compounds (XVIII) and (XXXVIII) to hydrolysis, respectively.

The hydrolysis is preferably carried out in the presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]non-5-ene, 1,4-diazabicyclo[2,2,2]octane, 1,5-diazabicyclo[5,4,0]-undecene-5, or the like.

Suitable acid may include an organic acid (e.g., formic acid, acetic acid, propionic acid, trifluoroacetic acid, etc.) and an inorganic acid (e.g., hydrochloric acid, hydrobromic acid, sulfuric acid, etc.).

The reaction is usually carried out in a solvent such as water, an alcohol (e.g., methanol, ethanol, etc.), a mixture thereof or any other solvent which does not adversely influence the reaction. A liquid base or acid can also be used as the solvent.

The reaction temperature is not critical and the reaction is usually carried out under cooling to warming.

(H) Process of (XIX)→(III$_c$) [Scheme (3)]

The compound (III$_c$) can be prepared by subjecting the compound (XIX) to acylation.

The acylating agent to be used for the present reaction and the reaction conditions of the present reaction can be referred to the ones exemplified for Process 3.

(I) Process of (XX)→(XXI) [Scheme (4) (i)]

The compound (XXI) can be prepared by subjecting the compound (XX) to nitrosation.

The nitrosating agent to be used for the present reaction may include conventional agent which give C-nitroso compound by reacting with activated methylene group, such as nitrous acid, alkali metal nitrite (e.g., sodium nitrite, etc.), lower alkyl nitrite (e.g., isopentyl nitrite, t-butyl nitrite, etc.) or the like.

In case that salt of nitrous acid is used as nitrosating agent, the present reaction is usually carried out in the presence of an acid such as an inorganic acid or an organic acid (e.g., hydrochloric acid, acetic acid, etc.) In case that ester of nitrous acid is used, the present reaction is preferably carried out in the presence of a strong base such as alkali metal alkoxide or the like.

The present reaction is usually carried out in a solvent such as water, acetic acid, benzene, alcohol (e.g., ethanol, methanol, etc.) or any other solvent which does not adversely influence the reaction.

The reaction temperature is not critical and the reaction is usually carried out under cooling or at ambient temperature.

(J) Processes of (XXI)+(XXII)→(XXIII) [Scheme (4) (i)] and (XXVIII)+(XXII)→(XXIX) [Scheme (5)]

The compounds (XXIII) and (XXIX) can be prepared by reacting the compounds (XXI) and (XXVIII) with the compound (XXII), respectively.

The present reaction is usually carried out in a solvent such as water, an alcohol (e.g., methanol, ethanol, etc.), benzene, dimethylacetamide, dimethylformamide, tetrahydrofuran, a mixture thereof or any other solvent which does not adversely influence the reaction.

The reaction temperature is not critical and the reaction is usually carried out from ambient temperature to under heating around the boiling point of the solvent.

In order to obtain syn-isomer of the compound (XXIII) or (XXIX) selectively and in high yield, it is necessary to use syn-isomer of the starting compound (XXI) or (XXVIII) and the present reaction is preferably carried out around neutral condition in the presence of a base as aforementioned. Preferable example of base may be week base such as alkali metal acetate (e.g., sodium acetate, potassium acetate, etc.), alkali metal bicarbonate (e.g., sodium bicarbonate, potassium bicarbonate, etc.) alkali metal carbonate (e.g., sodium carbonate, potassium carbonate, etc.) or the like.

(K) Processes of (XXIII)→(XXIII$_a$) [Scheme (4) (i)], (XXV)→(III$_d$) [Scheme (4) (ii)], (XXIX)→(III$_e$) [Scheme (5)], (XXXIII)→(XXXIV) [Scheme (6) (ii)]and (XXXV)→(III$_f$) [Scheme (6) (ii)]

The compounds (XXIII$_a$), (III$_d$), (III$_e$), (XXXIV) and (III$_f$) can be prepared by subjecting the compounds (XXIII), (XXV), (XXIX), (XXXIII) and (XXXV) to elimination reaction of the protective group of the carboxy, respectively.

In the present elimination reaction, conventional methods used in the elimination reaction of the protected carboxy, for example, hydrolysis etc. can be applicable. When the protective group is an ester, it can be eliminated by hydrolysis.

The present hydrolysis is carried out according to similar manners of those of processes (XVIII)→(III$_b$) and (XXXVIII)→(III$_g$) as mentioned in aforesaid (G).

(L) Process of (XXVII)→(XXVIII) [Scheme (5)]

The compound (XXVIII) can be prepared by halogenating the compound (XXVII).

The halogenating agent to be used in the present reaction may include a conventional halogenating agent used in halogenation of so-called activated methylene group such as halogen (e.g., bromine, chlorine, etc.), sulfuryl halide (e.g., sulfuryl chloride, etc.), hypohalite (e.g., hypochlorous acid, hypobromous acid, sodium hypochlorite, etc.), N-halogenated-imide (e.g., N-bromosuccinimide, N-bromophthalimide, N-chlorosuccinimide, etc.) and the like.

The present reaction is usually carried out in a solvent such as an organic acid (e.g., formic acid, acetic acid, propionic acid, etc.), carbon tetrachloride or any other solvent which does not adversely influence the reaction.

The reaction temperature is not critical and the reaction is usually carried out under cooling, at ambient temperature, under warming or heating.

(M) Processes of (XXX)→(XXXI) [Scheme (6) (i)] and (XXXIX)→(III$_h$) [Scheme (7)]

The compound (XXXI) can be prepared by reacting the compound (XXX) or its reactive derivative at the amino group or a salt thereof with an amino-protecting agent and the compound (III$_h$) can be prepared by reacting the compound (XXXIX) or its reactive derivative at the amino group or a salt thereof with an amino-protecting agent.

Suitable reactive derivative at the amino group of the compound (XXX) or (XXXIX) and suitable salt of the compound (XXX) or (XXXIX) may include the same ones as illustrated in the explanations of the reactive derivative at the amino group of the compound (II) and salt of the compound (II), respectively.

Suitable amino-protecting agent may include acylating agent which may include an aliphatic, aromatic and heterocyclic carboxylic acid, and the corresponding sulfonic acid, haloformic acid ester, isocyanic acid ester and carbamic acid, and the corresponding thio acid thereof, and the reactive derivative of the above acids.

Suitable reactive derivative of the above acids may include the same ones as illustrated in the explanation of Process 3. The example of the protective group (e.g. acyl group) to be introduced into the amino group in the compound (XXX) or (XXXIX) by the above amino-protecting agent (e.g. acylating agent) may be the same protecting group (e.g., acyl group) as illustrated in the explanation of the protective group moiety (e.g., acyl moiety) in the term of "acylamino".

The present amino-protecting reaction is carried out in a similar manner as illustrated in the reaction of the compound (II) with the compound (III) (Process 1).

(N) Process of (XXIII$_b$)→(XXXIII) [Scheme (6) (ii)]

The compound (XXXIII) can be prepared by subjecting the compound (XXIII$_b$) to hydrolysis.

The present hydrolysis is carried out in the presence of alkali metal bisulfite (e.g., sodium bisulfite, etc.) titanium trichloride, inorganic or organic acid such as hydrohalogenic acid (e.g., hydrochloric acid, hydrobromic acid, etc.), formic acid, nitrous acid or the like. Hydrohalogenic acid is preferably used in a combination of aldehyde (e.g., formaldehyde, etc.).

The present reaction is usually carried out in a solvent such as water, aqueous alcohol (e.g., aqueous methanol, aqueous ethanol, etc.), water-acetic acid or any other solvent which does not adversely influence the reaction.

The reaction temperature is not critical and the reaction is usually carried out at ambient temperature, under warming or heating.

In the present reaction, protected carboxy group may be occasionally transformed into free carboxy group. This case is also included in the scope of the present invention.

In the aforementioned reactions and/or the post-treating of the reactions of the present invention, the aforementioned tautomeric isomers may be occasionally transformed into the other tautomeric isomers and such case is also included in the scope of the present invention.

In case that the object compound (I) is obtained in a form of the free acid at 4 position and/or in case that the object compound (I) has free amino group, it may be transformed into its pharmaceutically acceptable salt as aforementioned by a conventional method.

The object compound (I) and pharmaceutically acceptable salt thereof of the present invention are all novel compounds which exhibit high antibacterial activity, inhibiting the growth of a wide variety of pathogenic microorganisms including Gram-positive and Gram-negative bacteria and are useful as antibacterial agents. Particularly, it is to be noted that the object compound (I), i.e., syn-isomer has much higher antibacterial activities than the corresponding anti-isomer to the compound (I), and accordingly the object compound (I), i.e., syn-isomer is characterized by having much superiority to the corresponding anti-isomer in the therapeutic value.

Now, in order to show the utility of the object compound (I), with regard to some representative compounds of this invention, there are shown the test data on the in vitro anti-bacterial activity, the test data on in vivo, i.e. the protecting effect against experimental infections and the acute toxicity in the following. Additionally, there are also shown the comparative test data on in vitro antibacterial activities relating to the corresponding anti-isomer to the object compound (I) for the reference's sake in the following.

Test Compounds (1)  7-[2-Methoxyimino-2-(3-hydroxyphenyl)acetamido]-3-carbamoyloxymethyl-3-cephem-4-carboxylic acid (syn isomer)

(2)  7-[2-Methoxyimino-2-(3-hydroxyphenyl)acetamido]-3-(1-methyl-1H-tetrazol-5-yl)thiomethyl-3-cephem-4-carboxylic acid (syn isomer)

(3)  7-[2-Methoxyimino-2-(3-hydroxyphenyl)acetamido]-3-(1-methyl-1H-tetrazol-5-yl)thiomethyl-3-cephem-4-carboxylic acid (syn isomer)

(4)  7-[2-Methoxyimino-2-(3-hydroxyphenyl)acetamido]-3-(1,3,4-thiadiazol-2-yl)thiomethyl-3-cephem-4-carboxylic acid (syn isomer)

(5)  7-[2-Methoxyimino-2-(3-acetoxyphenyl)acetamido]-3-(1,3,4-thiadiazol-2-yl)thiomethyl-3-cephem-4-carboxylic acid (syn isomer)

(6)  7-[2-Methoxyimino-2-(2-amino-1,3-thiazol-4-yl)acetamido]-3-(1-methyl-1H-tetrazol-5-yl)thiomethyl-3-cephem-4-carboxylic acid (syn isomer)

(7)  7-[2-Methoxyimino-2-(2-amino-1,3-thiazol-4-yl)acetamido]-3-(1-methyl-1H-tetrazol-5-yl)thiomethyl-3-cephem-4-carboxylic acid (anti isomer)

(8)  7-[2-Methoxyimino-2-(2-amino-1,3-thiazol-4-yl)acetamido]-cephalosporanic acid (syn isomer)

(9)  7-[2-Methoxyimino-2-(2-amino-1,3-thiazol-4-yl)acetamido-cephalosporanic acid (anti isomer)

(10) 7-[2-Methoxyimino-2-(2-formamido-1,3-thiazol-4-yl)acetamido]-3-(1,3,4-thiadiazol-2-yl)thiomethyl-3-cephem-4-carboxylic acid (syn isomer)

(11) 7-[2-Methoxyimino-2-(2-formamido-1,3-thiazol-4-yl)acetamido]-3-(1,3,4-thiadiazol-2-yl)thiomethyl-3-cephem-4-carboxylic acid (anti isomer)

(12) 7-[2-Methoxyimino-2-(2-formamido-1,3-thiazol-4-yl)acetamido]cephalosporanic acid (syn isomer)

(13) 7-[2-Methoxyimino-2-(2-amino-1,3-thiazol-4-yl)acetamido]-3-carbamoyloxymethyl-3-cephem-4-carboxylic acid (syn isomer)

(14) 7-[2-Methoxyimino-2-(2-amino-1,3-thiazol-4-yl)acetamido]-3-(1,3,4-thiadiazol-2-yl)thiomethyl-3-cephem-4-carboxylic acid (syn isomer)

(15) 7-[2-Methoxyimino-2-(2-amino-1,3-thiazol-4-yl)acetamido]-3-hydroxymethyl-3-cephem-4-carboxylic acid (syn isomer)

(16) 7-[2-Methoxyimino-2-(2-amino-1,3-thiazol-4yl)acetamido]-3-(5-methyl-1,3,4-thiadiazol-2-yl)thiomethyl-3-cephem-4-carboxylic acid (syn isomer)

(17) 7-[2-Methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer)

(18) 7-[2-Methoxyimino-2-{2-(2,2,2-trifluoroacetamido)-1,3-thiazol-4-yl}acetamido]-3-carbamoyloxymethyl-3-cephem-4-carboxylic acid (syn isomer)

(19) 7-[2-(2-Propynyl)oxyimino-2-(2-amino-1,3-thiazol-4-yl)acetamido]cephalosporanic acid (syn isomer)

(20) 7-[2-Isopropoxyimino-2-(2-amino-1,3-thiazol-4-yl)acetamido]-3-carbamoyloxymethyl-3-cephem-4-carboxylic acid (syn isomer)

1. In vitro antibacterial activity

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu$g/ml. after incubation at 37° C. for 20 hours.

Test Results

MIC (μg/ml) Test Compounds

| Test Bacteria | (1) | (2) | (3) | (4) | (5) | (6) | (7) | (8) | (9) | (10) | (11) | (12) | (13) | (14) | (15) | (16) | (17) | (18) |
|---|---|---|---|---|---|---|---|---|---|---|---|---|---|---|---|---|---|---|
| Escherichia coli NIHJ JC-2 | 1.56 | 1.56 | 50 | 3.13 | 12.5 | 0.20 | 12.5 | 0.10 | 3.13 | 0.78 | 12.5 | 1.56 | 1.56 | 0.10 | 0.78 | 0.39 | 0.20 | 3.13 |
| Klebsiella pneumoniae 417 | 0.39 | 0.39 | 6.25 | 0.78 | 0.78 | 0.10 | 6.25 | 0.10 | 1.56 | 1.56 | 3.13 | 1.56 | 0.05 | 0.20 | 0.05 | 0.10 | 0.20 | 0.05 |
| Proteus mirabilis 525 | 0.78 | 0.78 | 25 | 0.78 | 1.56 | 0.10 | 3.13 | 0.05 | 0.78 | 0.39 | 3.13 | 0.78 | 0.025 | 0.10 | 0.10 | 0.39 | 0.39 | 0.025 |

| Test Bacteria | MIC (μg/ml) Test Compounds | |
|---|---|---|
| | (19) | (20) |
| Bacillus subtilis ATCC 6633 | 3.13 | 1.56 |
| Proteus vulgaris IAM-1025 | 0.78 | 0.2 |
| Proteus vulgaris 1 | 0.78 | 0.2 |

As clearly seen from the above test results, the object compounds (I) of the present invention, i.e., syn-isomers have much higher antibacterial activity as compared with the corresponding anti-isomers thereof.

2. Protecting effect against experimental infections in mice

Test Method

Male ICR strain mice aged 4 weeks, each weighing 20–23 g were used in groups of 8 mice. The test bacteria were cultured overnight at 37° C. on HI-agar and then suspended in 2.5–5% mucin solution to obtain the suspension corresponding to each challenge cells. Mice were inoculated intraperitoneally with 0.5 ml of the suspension. A solution containing each test compounds was given subcutaneously to the mice in various dosage one hour after challenge. The $ED_{50}$ values were calculated from the number of surviving mice for each dosage after one week of observation.

Test Results
Protecting Effect against Experimental Infections in Mice

| Test Bacteria | Challenge cells/mouse | viable cells/ml | MIC of used strain (μg/ml) Test Compounds | | | | | $ED_{50}$ (S. C.) (mg/mouse) Test Compounds | | | | |
|---|---|---|---|---|---|---|---|---|---|---|---|---|
| | | | (8) | (14) | (5) | (4) | CET* | (8) | (14) | (5) | (4) | CET |
| Escherichia coli 29 | 6 × 10⁶ | 10⁸ | 0.2 | ≦0.03 | 0.78 | 0.78 | 12.5 | | | | | |
| | | 10⁶ | ≦0.03 | ≦0.03 | 0.39 | 0.78 | 3.13 | <0.005 | <0.005 | 0.081 | 0.111 | 1.402 |

*CET: 7-(2-Thienyl)acetamidocephalosporanic acid

| Test Bacteria | Challenge cells/mouse | viable cells/ml | MIC of used strain (μg/ml) Test Compounds | | | $ED_{50}$ (S. C.) (mg/mouse) Test Compounds | | |
|---|---|---|---|---|---|---|---|---|
| | | | (13) | (12) | Cefuro-* xime | (13) | (12) | Cefuroxime |
| Serratia marcesens 4 | 1.0 × 10⁶ | 10⁸ | 25 | 200 | 400 | | | |
| | | 10⁶ | ≦0.025 | 6.25 | 50 | <0.156 | 0.018 | 4.329 |

*Cefuroxime: 7-[2-Methoxyimino-2-(2-furyl)acetamido]-3-carbamoyloxymethyl-3-cephem-4-carboxylic acid (syn isomer)

| Test Bacteria | Challenge cells/mouse | viable cells/ml | MIC of used strain (μg/ml) Test Compounds | | $ED_{50}$ (S. C.) (mg/mouse) Test Compounds | |
|---|---|---|---|---|---|---|
| | | | (6) | Cefuroxime | (6) | Cefuroxime |
| Escherichia coli 100 | 3.5 × 10⁴ | 10⁸ | 1.56 | 12.5 | | |
| | | 10⁶ | 0.2 | 12.5 | 0.023 | 1.158 |

| Test Bacteria | Challenge cells/mouse | viable cells/ml | MIC of used strain (μg/ml) Test Compounds | | | $ED_{50}$ (S. C.) (mg/mouse) Test Compounds | | |
|---|---|---|---|---|---|---|---|---|
| | | | (2) | (1) | CEZ Na* | (2) | (1) | CEZ Na |
| Escherichia coli 29 | 5.5 × 10⁵ | 10⁸ | 0.78 | 0.39 | 3.13 | | | |
| | | 10⁶ | ≦0.1 | 0.2 | 0.78 | 0.386 | 0.079 | 0.182 |

*CEZ Na: Sodium 7-[2-(1H-tetrazol-1-yl)acetamido]-3-(5-methyl-1,3,4-thiadiazol-2-yl)thiomethyl-3-cephem-4-carboxylate 3. Acute Toxicity in Mice The same strain mice as aforesaid protecting test against experimental infections were used in groups of 10 mice. Test compound (8) (2 g) was administered intravenously to said mice. All mice survived without showing any disorder after one week observation.

For therapeutic administration, the object compound (I) of the present invention is used in the form of conventional pharmaceutical preparation which contains said compound, as an active ingredient, in admixture with a pharmaceutically acceptable carriers such as an organic or inorganic solid or liquid excipient which is suitable for oral, parenteral or external administration.

The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc., an average single dose of about 50 mg., 100 mg., 250 mg., and 500 mg. of the object compound (I) of the present invention has proved to be effective in treating diseases infected by pathogenic bacteria.

In general, amounts between 1 mg. and about 1000 mg. or even more may be administered to a patient.

The following examples are given for the purpose of illustrating the present invention:

EXAMPLE 1

A mixture of dimethylformamide (2.81 g.) and phosphorus oxychloride (5.36 g.) was warmed at 40° C. for 1 hour. After cooling, methylene chloride (60 ml.) was aded thereto and distilled off. To the residue was added dry ethyl acetate (50 ml.). Then, 2-methoxyimino-2-(3-hydroxyphenyl)acetic acid (syn isomer) (6.83 g.) was added thereto at 5° C. with stirring under ice-cooling. The resultant mixture was then stirred for 50 minutes at the same temperature. On the other hand, 7-amino-3-(1-methyl-1H-tetrazol-5-yl)thiomethyl-3-cephem-4-carboxylic acid (11.5 g.) and bis(trimethylsilyl)acetamide (28.4 g.) were dissolved in dry ethyl acetate (150 ml.) and stirred under cooling, to which was at a time added the above obtained solution at $-40°$ C. After stirring for 2 hours at $-30°$ to $-20°$ C., a saturated sodium chloride aqueous solution (100 ml.) was added at $-°$ C. to the reaction mixture. The mixture was stirred for 5 minutes. The precipitates were filtered off and ethyl acetate layer in the filtrate was separated. The aqueous layer was extracted twice with ethyl acetate (50 ml.). Ethyl acetate layer separated from the filtrate and the extracts were combined. The combined ethyl acetate solution was washed with a saturated sodium chloride aqueous solution (50 ml.). To the ethyl acetate layer was added activated charcoal and the mixture was stirred for 5 minutes and filtered. Water (100 ml.) was added to the filtrate and the resulting mixture was adjusted to pH 7 with an aqueous solution of sodium bicarbonate. The aqueous layer was separated and washed with methylene chloride. After the aqueous layer was separated, methylene chloride was removed from the aqueous layer by bubbling of nitrogen gas under ice-cooling. After filtration, the aqueous layer was adjusted to pH 2 with 10% hydrochloric acid with stirring and ice-cooling. Precipitating crystals were collected by filtration, washed with water and dried to give 7-[2-methoxyimino-2-(3-hydroxyphenyl)acetamido]-3-(1-methyl-1H-tetrazol-5-yl)thiomethyl-3-cephem-4-carboxylic acid (syn isomer) (11.3 g.).

I.R. spectrum (Nujol): 3250, 1770, 1725, 1670 cm$^{-1}$.

N.M.R. spectrum (d$_6$-DMSO, δ): ppm: 9.76 (1H, d, J=8 Hz); 6.7–7.40 (4H, m); 5.86 (1H, dd, J=5 Hz); 5.18 (1H, d, J=5 Hz); 4.34 (2H, AB$_q$, J=13 Hz); 3.92 (6H, s); 3.72 (2H, AB$_q$, J=17 Hz).

EXAMPLE 2

A mixture of dimethylformamide (1.41 g.) and phosphorus oxychloride (2.95 g.) was warmed for 1 hour at 40° C. After cooling, methylene chloride (30 ml.) was added thereto and distilled off. To the residue was added dry ethyl acetate (20 ml.). 2-Methoxyimino-2-(3-hydroxyphenyl)acetic acid (syn isomer) (3.4 g.) was added thereto with stirring and ice-cooling and the mixture was stirred for 30 minutes under ice-cooling. On the other hand, 7-amino-3-carbamoyloxymethyl-3-cephem-4-carboxylic acid (4.8 g.) was dissolved in a solution of trimethylsilylacetamide (27.5 g.) in dry ethyl acetate (70 ml.). To the solution was at a time added the above obtained solution at $-30°$ C. and the mixture was stirred for 1.5 hours at $-30°$ to $-10°$ C. A saturated sodium chloride aqueous solution was added to the reaction mixture at $-20°$ C. The ethyl acetate layer was separated and the aqueous layer was extracted with ethyl acetate. Two ethyl acetate layers were combined, washed with a sodium chloride aqueous solution and treated with activated charcoal. After filtration, water (100 ml.) was added to the filtrate and the mixture was adjusted to pH 7 with a sodium bicarbonate aqueous solution. The aqueous layer was separated and ethyl acetate was added thereto. The mixture was adjusted to pH 5 with 10% hydrochloric acid and the aqueous layer was separated. Ethyl acetate was added thereto and the mixture was adjusted to pH 2 with 10% hydrochloric acid. The ethyl acetate layer was separated and the aqueous layer was further extracted with ethyl acetate. Two ethyl acetate layers were combined, washed with a sodium chloride aqueous solution and dried over magnesium sulfate. The solvent was distilled off and the residue was pulverized with diisopropyl ether. The powder was collected by filtration and dried to give 7-[2-methoxyimino-2-(3-hydroxyphenyl)acetamido]-3-carbamoyl-oxymethyl-3-cephem-4-carboxylic acid (syn isomer) (3.26 g.).

I.R. spectrum (Nujol): 3500–3200, 1765, 1720, 1655 cm$^{-1}$.

N.M.R. spectrum (d$_6$-DMSO, δ): ppm 9.64 (1H, d, J=8 Hz); 6.70–7.20 (4H, m); 6.78 (2H, s); 5.92 (1H, dd, J=5,8 Hz); 5.16 (1H, d, J=5 Hz); 4.73 (2H, AB$_q$J=13 Hz); 3.91 (3H, s); 3.72 (2H, AB$_q$, J=17 Hz).

7-[2-Methoxyimino-2-(3-hydroxyphenyl)acetamido]-3-carbamoyloxymethyl-3-cephem-4-carboxylic acid (syn isomer) (1.98 g.) was suspended in water (15 ml.) and dissolved by adding sodium bicarbonate (0.35 g.) with stirring at ambient temperature. The solution was lyophilized and dried to give sodium 7-[2-methoxyimino-2-(3-hydroxyphenyl)acetamido]-3-carbamoyloxymethyl-3-cephem-4-carboxylate (syn isomer) (1.9 g.).

I.R. spectrum (Nujol): 3300, 1765, 1715, 1665 cm$^{-1}$.

N.M.R. spectrum (D$_2$O, δ): ppm: 6.83–7.60 (4H, m); 5.85 (1H, d, J=5 Hz); 5.17 (1H, d, J=5 Hz); 4.77 (2H, AB$_q$, J=13 Hz); 4.03 (3H, s); 3.48 (2H, AB$_q$, J=18 Hz).

EXAMPLE 3

A mixture of dry dimethylformamide (0.18 g.) and phosphorus oxychloride (0.38 g.) was stirred for 30 minutes at 40° C. Dry methylene chloride (15 ml.) was added thereto and distilled off under reduced pressure. To the residue was added dry ethyl acetate (15 ml.) and 2-methoxyimino-2-(3-chloro-4-hydroxyphenyl)acetic acid (syn isomer) (0.53 g.) was added thereto with stirring at $-20°$ C. The mixture was stirred for 1 hour below $-10°$ C. On the other hand, a mixture of 7-amino-3-trichloroacetylcarbamoyloxymethyl-3-cephem-4-carboxylic acid (1 g.), trimethylsilylacetamide (5 g.) and dry ethyl acetate (25 ml.) was stirred for 1 hour at ambient temperature. To this solution was dropwise added the above obtained solution with stirring below −10° and the resulting mixture was stirred for 2 hours at the same temperature. Water (50 ml.) and ethyl acetate (50 ml.) were added to the reaction mixture at −20° C, and the mixture was shaken. The organic layer containing 7-[2-methoxyimino-2-(3-chloro-4-hydroxyphenyl)acetamido]-3-trichloroacetylcarbamoyloxymethyl-3-cephem-4-carboxylic acid (syn isomer) was adjusted to pH 7.0 by adding water (50 ml.) and sodium bicarbonate and the mixture was stirred for 2 hours at ambient temperature. Ethyl acetate (50 ml.) was added to the aqueous layer and the mixture was adjusted to pH 5.0 with 10% hydrochloric acid. The aqueous layer was separated, adjusted to pH 2.0 with 10% hydrochloric acid and extracted with ethyl acetate (50 ml.). The extract was washed with ice-water and dried over magnesium sulfate. The solvent was distilled off under reduced pressure. The residue was thoroughly washed with ether, collected by filtration and dried to give 7-[2-methoxyimino-2-(3-chloro-4-hydroxyphenyl)acetamido]-3-carbamoyloxymethyl-3-cephem-4-carboxylic acid (syn isomer) (0.3 g.).

I.R. spectrum (Nujol): 3450, 3300, 1770, 1730, 1715, 1660, 1650, 1600 cm$^{-1}$.

N.M.R. spectrum (d$_6$-DMSO, δ): ppm: 9.72 (1H, d, J=8 Hz); 7.48 (1H, d, J=2 Hz); 7.40 (1H, dd, J=2,8 Hz); 6.98 (1H, d, J=8 Hz); 6.60 (2H, s); 5.70 (1H, q, J=5 Hz); 5.20 (1H, d, J=5 Hz); 4.74 (2H, AB$_q$, J=13 Hz); 3.90 (3H, s); 3.50 (2H, AB$_q$, J=18 Hz).

EXAMPLE 4

2-Methoxyimino-2-(3-hydroxyphenyl)acetic acid (syn isomer) (1.1 g.) and 7-amino-3-trichloroacetylcarbamoyloxymethyl-3-cephem-4-carboxylic acid (2.35 g.) were reacted and post-treated according to a similar manner to that of Example 3 to give 7-[2-methoxyimino-2-(3-hydroxyphenyl)acetamido]-3-carbamoyloxymethyl-3-cephem-4-carboxylic acid (syn isomer) (0.5 g.). This compound is identified with the compound obtained in Example 2 by I.R. and N.M.R. spectra.

EXAMPLE 5

(a) 2-t-Butoxycarbonylmethoxyimino-2-(3-chloro-4-hydroxyphenyl)acetic acid (syn isomer) (1 g.) and 7-amino-3-(1-methyl-1H-tetrazol-5-yl)thiomethyl-3-cephem-4-carboxylic acid (1 g.) were reacted according to similar manners to those of Examples 1 and 2 to give powder of 7-[2-t-butoxycarbonylmethoxyimino-2-(3-chloro-4-hydroxyphenyl)acetamido]-3-(1-methyl-1H-tetrazol-5-yl)thiomethyl-3-cephem-4-carboxylic acid (syn isomer) (1.5 g.).

(b) The powder obtained in Example 5(a) (1.5 g.) was added to a mixture of anisole (1.5 ml.) and trifluoroacetic acid (6 ml.) and the resulting mixture was stirred for 30 minutes at ambient temperature. The reaction mixture was adjusted to pH 8 by adding a sodium bicarbonate aqueous solution (50 ml.), ethyl acetate (50 ml.) and sodium bicarbonate under ice-cooling. The aqueous layer was separated, adjusted to pH 5.0 with 10% hydrochloric acid and washed with ethyl actatate (50 ml.). The aqueous layer was further adjusted to pH 2.0 with 10% hydrochloric acid and extracted with ethyl acetate (100 ml.). The extract was washed with water and dried over magnesium sulfate. The solvent was distilled off under reduced pressure and the residue was dissolved in pH 5.0 acetate buffer and subjected to column chromatography on Woelm neutral alumina (trade mark; made by ICN Company) using pH 5.0 acetate buffer as developing solvent. The eluate was adjusted to pH 2.0 with 10% hydrochloric acid under ice-cooling. Precipitating materials were collected by filtration, washed with water and dried to give 7-[2-carboxymethoxyimino-2-(3-chloro-4-hydroxyphenyl)acetamido]-3-(1-methyl-1H-tetrazol-5-yl)thiomethyl-3-cephem-4-carboxylic acid (syn isomer) (0.5 g.), mp 145° to 148° C. (dec.).

I.R. spectrum (Nujol): 3400, 3200–3300, 2500–2600, 1780, 1720, 1670, 1600 cm$^{-1}$.

N.M.R. spectrum (d$_6$-DMSO, δ): ppm: 9.70 (1H, d, J=8 Hz); 7.50 (1H, d, J=2 Hz); 7.45 (1H, dd, J=2,8 Hz); 7.10 (1H, d, J=8 Hz); 5.90 (1H, q, J=5 Hz); 5.22 (1H, d, J=5 Hz); 4.70 (2H, s); 4.35 (2H, AB$_q$, J=13 Hz); 3.95 (3H, s); 3.75 (2H, AB$_q$, J=18 Hz).

EXAMPLE 6

(a) 2-(1-t-Butoxycarbonylethoxyimino)-2-(3-chloro-4-hydroxyphenyl)acetic acid (syn isomer) (2 g.) and 7-amino-3-(1-methyl-1H-tetrazol-5-yl)thiomethyl-3-cephem-4-carboxylic acid (2 g.) were reacted according to similar manners to those of Examples 1 and 2 to give powder of 7-[2-(1-t-butoxycarbonylethoxyimino)-2-(3-chloro-4-hydroxyphenyl)acetamido]-3-(1-methyl-1H-tetrazol-5-yl)thiomethyl-3-cephem-4-carboxylic acid (syn isomer) (3.6 g.).

(b) The powder obtained in Example 6(a) (3.6 g.), anisole (4 ml.) and trifluoroacetic acid (16 ml.) were reacted according to a similar manner to that of Example 5(b) to give yellow powder of 7-[2-(1-carboxyethoxyimino)-2-(3-chloro-4-hydroxyphenyl)acetamido]-3-(1-methyl-1H-tetrazol-5-yl)thiomethyl-3-cephem-4-carboxylic acid (syn isomer) (2.0 g.), mp 147° to 151° C. (dec.).

I.R. spectrum (Nujol): 3500, 3250, 2500–2600, 1780, 1730, 1660, 1630, 1600 cm$^{-1}$.

N.M.R. spectrum (d$_6$-DMSO, δ): ppm: 9.62 (1H, d, J=8 Hz); 7.46 (1H, d, J=2 Hz); 7.34 (1H, dd, J=2,8 Hz); 7.04 (1H, d, J=8 Hz); 5.90 (1H, q, J=5 Hz); 5.22 (1H, d, J=5 Hz); 4.73 (1H, q, J=6 Hz); 4.33 (2H, AB$_q$, J=13 Hz); 4.00 (3H, s); 3.73 (2H, AB$_q$, J=18 Hz); 1.37 (3H, d, J=6 Hz).

EXAMPLE 7

The following compounds were obtained according to similar manners to those of Examples 1 and 2.

(1) 7-[2-Methoxyimino-2-(3-hydroxyphenyl)acetamido]-3-(4H-1,2,4-triazol-3-yl)thiomethyl-3-cephem-4-carboxylic acid (syn isomer).

I.R. spectrum (Nujol): 3250, 1775, 1710, 1665 cm$^{-1}$.

N.M.R. spectrum (d$_6$-DMSO, δ): ppm: 9.67 (1H, d, J=8 Hz); 8.40 (1H, s); 6.70–7.43 (4H, m); 5.82 (1H, dd, J=5,8 Hz); 5.13 (1H, d, J=5 Hz); 4.18 (2H, AB$_q$, J=13 Hz); 3.90 (3H, s); 3.67 (2H, broad s).

(2) 7-[2-Methoxyimino-2-(3-hydroxyphenyl)acetamido]-3-(1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ): ppm: 9.78 (1H, d, J=8 Hz); 9.55 (1H, s); 6.70–7.40 (4H, m); 5.89 (1H, dd, J=5,8 Hz); 5.22 (1H, d, J=5 Hz); 4.46 (2H, AB$_q$, J=13 Hz); 3.92 (3H, s); 3.76 (2H, AB$_q$, J=18 Hz).

(3) 7-[2-Methoxyimino-2-(3-hydroxyphenyl)acetamido]-3-(5-methyl-1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d6-DMSO, δ): ppm: 9.72 (1H, d, J=8 Hz); 6.62–7.40 (4H, m); 5.94 (1H, dd, J=5,8 Hz); 5.18 (1H, d, J=5 Hz); 4.18 (2H, AB$_q$, J=13 Hz); 3.89 (3H, s); 3.70 (2H, AB$_q$, J=17 Hz); 2.65 (3H, s).

(4) 7-[2-Methoxyimino-2-(3-hydroxyphenyl)acetamido]-cephalosporanic acid (syn isomer).

I.R. spectrum (Nujol): 3250, 1785, 1740, 1720 cm$^{-1}$.

N.M.R. spectrum (d6-DMSO, δ): ppm: 9.78 (1H, d, J=8 Hz); 6.86–7.36 (4H, m); 5.86 (1H, dd, J=5,8 Hz); 5.18 (1H, d, J=5 Hz); 4.84 (2H, AB$_q$, J=13 Hz); 3.98 (3H, s); 3.54 (2H, AB$_q$, J=17 Hz); 2.00 (3H, s).

(5) 7-[2-Methoxyimino-2-(3-methoxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d6-DMSO, δ): ppm: 9.78 (1H, d, J=8 Hz); 6.95–7.54 (4H, m); 5.94 (1H, dd, J=5,8 Hz); 5.18 (1H, d, J=5 Hz); 4.12 (2H, AB$_q$, J=13 Hz); 3.92 (6H, s); 3.76 (3H, s); 3.72 (2H, AB$_q$, J=18 Hz).

(6) 7-[2-Methoxyimino-2-(4-hydroxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d6-DMSO, δ): ppm: 9.70 (1H, d, J=8 Hz); 7.44 (2H, d, J=8 Hz); 6.84 (2H, d, J=8 Hz); 5.86 (1H, dd, J=5,8 Hz); 5.18 (1H, d, J=5 Hz); 4.34 (2H, AB$_q$, J=13 Hz); 3.93 (3H, s); 3.87 (3H, s); 3.74 (2H, AB$_q$, J=18 Hz).

(7) 7-[2-Methoxyimino-2-(3-chloro-4-hydroxyphenyl)acetamido]-3-(1-methyl-1H-tetrazol-5-yl)thiomethyl-3-cephem-4-carboxylic acid (syn isomer), mp 145° to 148° C. (dec).

I.R. spectrum (Nujol): 3500, 3250, 2500–2600, 1780, 1720, 1655, 1625, 1600 cm$^{-1}$.

N.M.R. spectrum (d6-DMSO, δ): ppm: 10.80 (1H, broad s); 9.68 (1H, d, J=2 Hz); 7.46 (1H, d, J=2 Hz); 7.32 (1H, q, J=2,8 Hz); 7.00 (1H, d, J=8 Hz); 5.80 (1H, q, J=5 Hz); 5.16 (1H, d, J=5 Hz); 4.28 (2H, AB$_q$, J=13 Hz); 3.92 (3H, s); 3.87 (3H, s); 3.72 (2H, AB$_q$, J=18 Hz).

(8) 7-[2-Methoxyimino-2-(3-chloro-4-methoxyphenyl)acetamido]-3-(1-methyl-1H-tetrazol-5-yl)thiomethyl-3-cephem-4-carboxylic acid (syn isomer), mp 143° to 145° C. (dec.).

I.R. spectrum (Nujol): 3300, 2500–2600, 1785, 1730, 1670, 1630, 1600 cm$^{-1}$.

N.M.R. spectrum (d6-DMSO, δ): ppm: 9.76 (1H, d, J=8 Hz); 7.56 (1H, d, J=2 Hz); 7.48 (1H, dd, J=2,8 Hz); 7.22 (1H, d, J=8 Hz); 5.84 (1H, q, J=5 Hz); 5.18 (1H, d, J=5 Hz); 4.27 (2H, AB$_q$, J=13 Hz); 3.90 (6H, s); 3.88 (3H, s); 3.70 (2H, AB$_q$, J=18 Hz).

(9) 7-[2-Methoxyimino-2-(3-nitro-4-hydroxyphenyl)acetamido]3-(1-methyl-1H-tetrazol-5-yl)thiomethyl-3-cephem-4-carboxylic acid (syn isomer), mp 149° to 152° C. (dec.).

I.R. spectrum (Nujol): 3400–3450, 3200, 2500–2600, 1780, 1720, 1660, 1620, 1600, 1535, 1350 cm$^{-1}$.

N.M.R. spectrum (d6-DMSO, δ): ppm: 9.72 (1H, d, J=8 Hz); 7.97 (1H, d, J=2 Hz); 7.72 (1H, dd, J=2, 8 Hz); 7.21 (1H, d, J=8 Hz); 5.82 (1H, q, J=5 Hz); 5.16 (1H, d, J=5 Hz); 4.3 (2H, AB$_q$, J=13 Hz); 3.92 (3H, s); 3.87 (3H, s); 3.72 (2H, AB$_q$, J=18 Hz).

(10) 7-[2-Allyloxyimino-2-(3-chloro-4-hydroxyphenyl)acetamido]-3-(1-methyl-1H-tetrazol-5-yl)thiomethyl-3-cephem-4-carboxylic acid (syn isomer), mp 163° to 165° C. (dec.).

I.R. spectrum (Nujol): 3200–3300, 2500–2600, 1780, 1720, 1670, 1600 cm$^{-1}$.

N.M.R. spectrum (d6-DMSO, δ): ppm: 9.70 (1H, d, J=8 Hz); 7.40 (1H, d, J=2 Hz); 7.30 (1H, dd, J=2, 8 Hz); 6.95 (1H, d, J=8 Hz); 5.80 (2H, m); 5.30 (2H, d, J=8 Hz); 5.10 (1H, d, J=5 Hz); 4.60 (2H, d, J=5 Hz); 4.27 (2H, AB$_q$, J=13 Hz); 3.85 (3H, s); 3.65 (2H, AB$_q$, J=18 Hz).

(11) 7-[2-Allyloxyimino-2-(3-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3250–3350, 2550–2600, 1780, 1730, 1670, 1650, 1600 cm$^{-1}$.

N.M.R. spectrum (d6-DMSO, δ): ppm: 9.70 (1H, d, J=8 Hz); 7.2–6.8 (4H, m); 6.1–5.8 (2H, m); 5.35 (2H, d, J=8 Hz); 5.17 (1H, d, J=5 Hz); 4.7 (2H, d, J=5 Hz); 4.17 (2H, AB$_q$, J=13 Hz); 3.93 (3H, s); 3.75 (2H, AB$_q$, J=18 Hz).

(12) Sodium 7-[2-methoxyimino-2-(3-hydroxyphenyl)acetamido]cephalosporanate (syn isomer).

I.R. spectrum (Nujol): 3250, 1765, 1730, 1665 cm$^{-1}$.

N.M.R. spectrum (D$_2$O, δ): ppm: 6.83–7.13 (4H, m); 5.83 (1H, d, J=5 Hz); 5.17 (1H, d, J=5 Hz); 4.82 (2H, AB$_q$, J=13 Hz); 4.03 (3H, s); 3.50 (2H, AB$_q$, J=17 Hz); 2.1 (3H, s).

(13) 7-[2-(3-Hydroxy-4-bromobenzyloxyimino)-2-(4-hydroxyphenyl)acetamido]-3-(1-methyl-1H-tetrazol-5-yl)thiomethyl-3-cephem-4-carboxylic acid (syn isomer), powder.

I.R. spectrum (Nujol): 3150, 1780, 1720, 1670 cm$^{-1}$.

N.M.R. spectrum (d6-DMSO, δ): ppm: 9.60 (1H, d, J=8 Hz); 6.72–7.52 (7H, m); 5.80 (1H, dd, J=4, 8 Hz); 5.15 (1H, d, J=4 Hz); 5.00 (2H, s); 4.28 (2H, AB$_q$, J=13 Hz); 3.90 (3H, s); 3.65 (2H, AB$_q$, J=18 Hz).

(14) 7-[2-(2-Thienylmethoxyimino)-2-(4-hydroxyphenyl)acetamido]-3-(1-methyl-1H-tetrazol-5-yl)thiomethyl-3-cephem-4-carboxylic acid (syn isomer), powder.

I.R. spectrum (Nujol): 3200–3300, 1780, 1720, 1660 cm$^{-1}$.

N.M.R. spectrum (d6DMSO, δ): ppm: 9.77 (1H, d, J=8 Hz); 6.7–7.7 (7H, m); 5.83 (1H, dd, J=5, 8 Hz); 5.29 (2H, s); 5.15 (1H, d, J=5 Hz); 4.3 (2H, AB$_q$, J=13 Hz); 3.92 (3H, s); 3.72 (2H, AB$_q$, J=18 Hz).

(15) 7-[2-Ethoxyimino-2-(3-chloro-4-hydroxyphenyl)acetamido]-3-(1-methyl-1H-tetrazol-5-yl)thiomethyl-3-cephem-4-carboxylic acid (syn isomer), colorless powder, mp 153° to 156° C. (dec.).

I.R. spectrum (Nujol): 3450, 3250, 2550–2600, 1780, 1725, 1665, 1630, 1600 cm$^{-1}$.

N.M.R. spectrum (d6-DMSO, δ): ppm: 9.71 (1H, d, J=8 Hz); 7.50 (1H, d, J=2 Hz); 7.36 (1H, dd, J=2, 8 Hz); 7.03 (1H, d, J=8 Hz); 5.83 (1H, q, J=5 Hz); 5.17 (1H, d, J=5 Hz); 4.33 (2H, AB$_q$, J=13 Hz); 4.17 (2H, q, J=7 Hz); 3.97 (3H, s); 3.73 (2H, AB$_q$, J=18 Hz); 1.25 (3H, t, J=7 Hz).

(16) 7-[2-Allyloxyimino-2-(3-methoxyphenyl)acetamido]-3-(1-methyl-1H-tetrazol-5-yl)thiomethyl-3-cephem-4-carboxylic acid (syn isomer), powder, mp 135° to 138° C. (dec.).

I.R. spectrum (Nujol): 3300, 2600, 1785, 1730, 1670, 1645, 1600 cm$^{-1}$.

N.M.R. spectrum (d6-DMSO, δ): ppm: 9.82 (1H, d, J=8 Hz); 7.0–7.45 (4H, m); 5.8–6.2 (2H, m); 5.36 (2H, t, J=10 Hz); 5.21 (1H, d, J=5 Hz); 4.72 (2H, d, J=5 Hz); 4.36 (2H, AB$_q$, J=13 Hz); 3.95 (3H, s); 3.91 (3H, s); 3.87 (2H, AB$_q$, J=18 Hz).

(17) 7-[2-Ethoxyimino-2-(3-hydroxyphenyl)acetamido]-3-(1-methyl-1H-tetrazol-5-yl)thiomethyl-3- cephem-4-carboxylic acid (syn isomer), yellow powder, mp 145° to 148° C. (dec.).

I.R. spectrum (Nujol): 3450, 3250, 2500–2600, 1775, 1720, 1665, 1620, 1600 cm$^{-1}$.

N.M.R. spectrum (d$_6$-DMSO, δ): ppm: 9.70 (1H, d, J=8 Hz); 6.8–7.4 (4H, m); 5.90 (1H, q, J=5 Hz); 5.20 (1H, d, J=5 Hz); 4.36 (2H, AB$_q$, J=13 Hz); 4.20 (2H, q, J=7 Hz); 4.00 (3H, s); 3.76 (2H, AB$_q$, J=18 Hz); 1.33 (3H, t, J=7 Hz).

(18) 7-[2-Ethoxyimino-2-(3-methoxyphenyl)acetamido]-3-(1-methyl-1H-tetrazol-5-yl)thiomethyl-3-cephem-4-carboxylic acid (syn isomer), pale yellow powder, mp 140° to 143° C. (dec.).

I.R. spectrum (Nujol): 3300, 2500–2600, 1785, 1730, 1670, 1630, 1600 cm$^{-1}$.

N.M.R. spectrum (d$_6$-DMSO, δ): ppm: 9.71 (1H, d, J=8 Hz); 6.9–7.5 (4H, m); 5.90 (1H, q, J=5 Hz); 5.17 (1H, d, J=5 Hz); 4.33 (2H, AB$_q$, J=13 Hz); 4.20 (2H, q, J=7 Hz); 3.95 (3H, s); 3.85 (3H, s); 3.75 (2H, AB$_q$, J=18 Hz); 1.30 (3H, t, J=7 Hz).

(19) 7-[2-Allyloxyimino-2-(3-chloro-4-methoxyphenyl)acetamido]-3-(1-methyl-1H-tetrazol-5-yl)thiomethyl-3-cephem-4-carboxylic acid (syn isomer), pale yellow powder, mp 153° to 156° C. (dec).

I.R. spectrum (Nujol): 3250, 2600, 1780, 1720, 1670, 1645, 1630, 1600 cm$^{-1}$.

N.M.R. spectrum (d$_6$-DMSO, δ): ppm: 9.65 (1H, d, J=8 Hz); 7.27 (1H, d, J=2 Hz); 7.20 (1H, dd, J=2, 8 Hz); 7.09 (1H, d, J=8 Hz); 5.85–6.15 (2H, m); 5.15 (2H, t, J=9 Hz); 5.05 (1H, d, J=5 Hz); 4.60 (2H, d, J=5 Hz); 4.15 (2H, AB$_q$, J=13 Hz); 3.95 (3H, s); 3.90 (3H, s); 3.47 (2H, AB$_q$, J=18 Hz).

(20) 7-[2-Methoxyimino-2-(3-acetoxyphenyl)acetamido]-3-carbamoyloxymethyl-3-cephem-4-carboxylic acid (syn isomer).

I.R. spectrum (Nujol): 3450, 3250, 1765, 1710, 1655, 1530 cm$^{-1}$.

N.M.R. spectrum (d$_6$-DMSO, δ): ppm: 9.77 (1H, d, J=8 Hz); 7.6–7.1 (4H, m); 6.56 (2H, s); 5.83 (1H, dd, J=4,8 Hz); 5.20 (1H, d, J=4 Hz); 4.76 (2H, AB$_q$, J=13 Hz); 3.94 (3H, s); 3.55 (2H, broad s); 2.28 (3H, s).

(21) 7-[2-Phenylthiomethoxyimino-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3300, 1760, 1660, 1600, 1580, 1520 cm$^{-1}$.

N.M.R. spectrum (d$_6$-DMSO, δ): ppm: 9.7 (1H, d, J=8 Hz); 7.7–6.7 (9H, m); 5.8–5.4 (3H, broad s); 5.06 (1H, d, J=5 Hz); 4.33 (2H, broad s); 3.9 (3H, s); 3.56 (2H, broad s).

(22) 7-[2-Methoxyimino-2-(3-mesylaminophenyl)acetamido]-3-(1,3,4-thiadiazol-2-yl)thiomethyl-3-cephem-4-carboxylic acid (syn isomer), mp 155° C. (dec.).

I.R. spectrum (Nujol): 3300, 1780, 1730, 1670 cm$^{-1}$.

N.M.R. spectrum (d$_6$-DMSO), δ): ppm: 9.98 (1H, s); 9.81 (1H, d, J=9 Hz); 9.62 (1H, s); 5.90 (1H, dd, J=5, 9 Hz); 5.24 (1H, d, J=5 Hz); 4.49 (2H, ABq, J=14 Hz); 3.98 (3H, s); 3.77 (2H, broad s); 2.96 (3H, s).

(23) 7-[2-Methoxyimino-2-(3-carbamoyloxyphenyl)acetamido]-3-(1-methyl-1H-tetrazol-5-yl)thiomethyl-3-cephem-4-carboxylic acid (syn isomer).

I.R. spectrum (Nujol): 3450, 3300, 3200, 1780, 1725, 1670 1620, 1590, 1520 cm$^{-1}$.

N.M.R. spectrum (d$_6$-DMSO, δ): ppm: 9.77 (1H, d, J=7 Hz); 7.6–6.8 (6H, m); 5.83 (1H, dd, J=4, 7 Hz); 5.17 (1H, d, J=4 Hz); 4.31 (2H, ABq, J=14 Hz); 3.96 (6H, s); 3.72 (2H, broad s).

(24) 7-[2-Methoxyimino-2-(3-carbamoyloxyphenyl)acetamido]-3-(1,3,4-thiadiazol-2-yl)thiomethyl-3-cephem-4-carboxylic acid (syn isomer).

I.R. spectrum (Nujol): 3250, 1780, 1735, 1675 cm$^{-1}$.

N.M.R. spectrum (d$_6$-DMSO, δ): ppm: 9.81 (1H, d, J=8 Hz); 9.62 (1H, s); 6.7–7.58 (4H, m); 5.87 (1H, dd, J=5, 8 Hz); 5.2 (1H, d, J=5 Hz); 4.25, 4.63 (2H, ABq, J=14 Hz); 3.9 (3H, s); 3.7 (2H, broad s).

(25) 7-[2-Methoxyimino-2-(3-acetoxyphenyl)acetamido]-3-(1,3,4-thiadiazol-2-yl)thiomethyl-3-cephem-4-carboxylic acid (syn isomer).

I.R. spectrum (Nujol): 3250, 1780, 1740, 1720, 1680 cm$^{-1}$.

N.M.R. spectrum (d$_6$-DMSO, δ): ppm: 9.86 (1H, d, J=8 Hz); 9.61 (1H, s); 7.00–7.65 (4H, m); 5.84 (1H, dd, J=5, 8 Hz); 5.2 (1H, d, J=5 Hz); 4.25, 4.63 (2H, ABq, J=14 Hz); 3.92 (3H, s); 3.53, 3.86 (2H, ABq, J=19 Hz); 2.3 (3H, s).

(26) 7-[2-(3-Phenylallyloxyimino)-2-(3-hydroxyphenyl)acetamido]-3-(1-methyl-1H-tetrazol-5-yl)thiomethyl-3-cephem-4-carboxylic acid (syn isomer), mp 138° to 142° C. (dec.)

I.R. spectrum (Nujol): 3300–3400, 2600, 1780, 1720, 1665, 1600 cm$^{-1}$.

N.M.R. spectrum (d$_6$-DMSO, δ): ppm: 9.80 (1H, d, J=8 Hz); 6.4–7.4 (11H, m); 5.85 (1H, dd, J=5, 8 Hz); 5.20 (1H, d, J=5 Hz); 4.83 (2H, d, J=5 Hz); 4.32 (2H, ABq, J=15 Hz); 3.95 (3H, s); 3.68 (2H, ABq, J=18 Hz).

(27) 7-[2-Methoxyimino-2-(4-dimethylaminophenyl)acetamido]3-(1-methyl-1H-tetrazol-5-yl)thiomethyl-3-cephem-4-carboxylic acid (syn isomer), mp 88° C. (dec.).

I.R. spectrum (Nujol): 3250, 1780, 1730, 1680, 1610 cm$^{-1}$.

N.M.R. spectrum (d$_6$-DMSO, δ): ppm: 9.63 (1H, d, J=8 Hz); 7.40 (2H, d, J=8 Hz); 6.73 (2H, d, J=8 Hz); 5.83 (1H, dd, J=5, 8 Hz); 5.17 (1H, d, J=5 Hz); 4.33 (2H, ABq, J=13 Hz); 3.97 (3H, s); 3.87 (3H, s); 3.73 (2H, broad s); 3.00 (6H, s).

(28) 7-[2-Methoxyimino-2-(3-hydroxyphenyl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d$_6$-DMSO, δ): ppm: 9.67 (1H, d, J=9 Hz); 6.72–7.36 (4H, m); 5.78 (1H, dd, J=5, 9 Hz); 5.12 (1H, d, J=5 Hz); 4.55 (2H, broad s); 4.30 (2H, broad s); 3.90 (3H, s); 3.40–3.80 (2H, m); 3.14 (2H, broad s); 2.48 (6H, s).

(29) 7-[2-{2-(2-Hydroxyphenoxy)ethoxyimino}-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3270, 1780, 1725, 1670, 1560 cm$^{-1}$.

N.M.R. spectrum (d$_6$-DMSO, δ): ppm: 6.5–7.4 (8H, m); 5.86 (1H, dd, J=5, 8 Hz); 5.14 (1H, d, J=5 Hz); 4.0–4.6 (6H, m); 3.92 (3H, s); 3.52, 3.70 (2H, AB$_q$, J=7 Hz).

EXAMPLE 8

A mixture of dimethylformamide (0.73 g) and phosphorus oxychloride (1.6 g) was warmed for 30 minutes at 40° C. Benzene was added thereto and the mixture was concentrated. The residue was suspended in ethyl acetate (20 ml) and 2-methoxyimino-2-(3-hydroxyphenyl) acetic acid (syn isomer) (1.95 g) was added thereto at −15° to −5° C., after which the resulting mixture was stirred for 30 minutes at the same temperature. On the other hand, a solution of sodium hydroxide (0.9 g) in water (5 ml) was dropwise added at 0° to 5° C. over 25 minutes to a suspension of 7-aminocephalosporanic acid (2.7 g) in water (12.5 ml) and the mixture was stirred for 5 minutes, after which acetone (20 ml) was added thereto. To the resulting mixture containing sodium 7-amino-3-hydroxymethyl-3-cephem-4-carboxylate was dropwise added at 0° to 5° C. over 3 minutes the above obtained ethyl acetate solution keeping the pH value at 7.5 to 8.5 by adding triethylamine. After stirring for 30 minutes, the organic solvents were distilled off. The aqueous layer was washed with ethyl acetate (20 ml), adjusted to pH 2.0 with hydrochloric acid and extracted with ethyl acetate (60 ml) at 0° to 3° C. The aqueous layer was further extracted with ethyl acetate (30 ml). The combined ethyl acetate extracts were washed with a saturated aqueous solution of sodium chloride and dried. The solvent was distilled off and the residue was pulverized with diisopropyl ether to give a mixture of 7-[2-methoxyimino-2-(3-hydroxyphenyl)acetamido]-3-hydroxymethyl-3-cephem-4-carboxylic acid (syn isomer) (I) and 6-[2-methoxyimino-2-(3-hydroxyphenyl)acetamido]-5a,6-dihydro-3H,7H-azeto[2,1-b]-furo[3,4-d][1,3]thiazine-1,7(4H)-dione (syn isomer) (II) (2.64 g).

I.R. spectrum of (I) (Nujol): 3250, 1785, 1755, 1660, 1600, 1570, 1540 cm$^{-1}$.

N.M.R. spectrum of (I) (d$_6$-DMSO, $\delta$): ppm: 9.83 (1H, d, J=8 Hz); 7.5–6.75 (4H, m); 5.8 (1H, dd, J=5,8 Hz); 5.21 (1H, d, J=5 Hz); 4.3 (2H, broad s); 3.95 (3H, s); 3.63 (2H, broad s).

I.R. spectrum of (II) (Nujol): 3250, 1785, 1755, 1660, 1600, 1570, 1540 cm$^{-1}$.

N.M.R. spectrum of (II) (d$_6$-DMSO, $\delta$): ppm: 9.83 (1H, d, J=8 Hz); 7.5–6.75 (4H, m); 6.02 (1H, dd, J=5, 8 Hz); 5.21 (1H, d, J=5 Hz); 5.07 (2H, broad s); 3.95 (3H, s); 3.84 (2H, broad s).

EXAMPLE 9

7-[2-Methoxyimino-2-(3-hydroxyphenyl)acetamido]-3-carbamoyloxymethyl-3-cephem-4-carboxylic acid (syn isomer) (0.23 g) was dissolved in pyridine (1 ml) with stirring and ice-cooling, and acetyl chloride (0.082 g) was added thereto. The mixture was stirred for 40 minutes under ice-cooling. The reaction mixture was poured into ice-water, acidified with hydrochloric acid and extracted with ethyl acetate. The extract was washed with a saturated aqueous solution of sodium chloride and dried over magnesium sulfate. After treating with activated charcoal, it was filtered and the filtrate was concentrated. The residue was pulverized with diisopropyl ether to give a mixture of 7-[2-methoxyimino-2-(3-acetoxyphenyl)acetamido]-3-carbamoyloxymethyl-3-cephem-4-carboxylic acid (syn isomer) and 7-[2-methoxyimino-2-(3-acetoxyphenyl)acetamido]-3-carbamoyloxymethyl-2-cephem-4-carboxylic acid (syn isomer) (0.18 g).

N.M.R. spectrum (d$_6$-DMSO, $\delta$): ppm: 9.82 (1H, d, J=8 Hz); 9.77 (1H, d, J=8 Hz); 7.6–7.1 (8H, m); 6.60 (1H, s); 6.56 (2H, s); 5.83 (1H, dd, J=4, 8 Hz); 5.60 (1H, dd, J=4,8 Hz); 5.24 (1H, d, J=4 Hz); 5.20 (1H, d, J=4 Hz); 4.84 (1H, s); 4.76 (2H, ABq, J=13 Hz); 4.56 (2H, broad s); 3.94 (6H, s); 3.55 (2H, broad s); 2.28 (6H, s).

EXAMPLE 10

The following compounds were obtained according to a similar manner to that of Example 9.

(1) 7-[2-Methoxyimino-2-(3-acetoxyphenyl)acetamido]-3-(1,3,4-thiadiazol-2-yl)thiomethyl-3-cephem-4-carboxylic acid (syn isomer).

I.R. spectrum (Nujol): 3250, 1780, 1740, 1720, 1680 cm$^{-1}$.

N.M.R. spectrum (d$_6$-DMSO, $\delta$): ppm: 9.86 (1H, d, J=8 Hz); 9.61 (1H, s); 7.00–7.65 (4H, m); 5.84 (1H, dd, J=5, 8 Hz); 5.2 (1H, d, J=5 Hz); 4.25, 4.63 (2H, ABq, J=14 Hz); 3.92 (3H, s); 3.53, 3.86 (2H, ABq, J=19 Hz); 2.3 (3H, s).

(2) 7-[2-Methoxyimino-2-(3-carbamoyloxyphenyl)acetamido]-3-(1-methyl-1H-tetrazol-5-yl)thiomethyl-3-cephem-4-carboxylic acid (syn isomer).

I.R. spectrum (Nujol): 3450, 3300, 3200, 1780, 1725, 1670, 1620, 1590, 1520 cm$^{-1}$.

N.M.R. spectrum (d$_6$-DMSO, $\delta$): ppm: 9.77 (1H, d, J=7 Hz); 7.6–6.8 (6H, m); 5.83 (1H, dd, J=4, 7 Hz); 5.17 (1H, d, J=4 Hz); 4.31 (2H, ABq, J=14 Hz); 3.96 (6H, s); 3.72 (2H, broad s).

(3) 7-[2-Methoxyimino-2-(3-carbamoyl-oxyphenyl)acetamido]-3-(1,3,4-thiadiazol-2-yl)thiomethyl-3-cephem-4-carboxylic acid (syn isomer).

I.R. spectrum (Nujol): 3250, 1780, 1735, 1675 cm$^{-1}$.

N.M.R. spectrum (d$_6$-DMSO, $\delta$): ppm: 9.81 (1H, d, J=8 Hz); 9.62 (1H, s); 6.7–7.58 (4H, m); 5.87 (1H, dd, J=5, 8 Hz); 5.2 (1H, d, J=5 Hz); 4.25, 4.63 (2H, ABq, J=14 Hz); 3.9 (3H, s); 3.7 (2H, broad s).

EXAMPLE 11

Phosphorus oxychloride (0.26 g.) was added under ice-cooling to dimethylformamide (0.15 g.) and the mixture was warmed at 40° C. for 1 hour. Ethyl acetate (1.5 ml.) was added thereto and to the mixture was at a time added 2-methoxyimino-2-(2-methyl-1,3-thiazol-4-yl)acetic acid (syn isomer) (0.3 g.) with stirring and ice-cooling, after which the resulting mixture was stirred for 20 minutes at 0° to 5° C. On the other hand, bis(trimethylsilyl)acetamide (1.2 g.) was added to a suspension of 7-amino-3-(1-methyl-1H-tetrazol-5-yl)thiomethyl-3-cephem-4-carboxylic acid (0.53 g.) in ethyl acetate (7 ml.) and the mixture was stirred at ambient temperature. To this solution was dropwise added the above obtained ethyl acetate solution at −20° C. and the mixture was stirred for 2 hours at −10° to −20° C. Water (20 ml.) was added to the reaction mixture below −25° C. and ethyl acetate (20 ml.) was added thereto, after which the mixture was stirred. An insoluble material was filtered off and the ethyl acetate layer was separated. Water (15 ml.) was added to the ethyl acetate layer and the mixture was adjusted to pH 7.5 with a saturated aqueous solution of sodium bicarbonate. The aqueous layer was separated, washed with methylene chloride and methylene chloride in the aqueous layer was removed by bubbling of nitrogen gas. The aqueous solution was adjusted to pH 2.2 with 10% hydrochloric acid and precipitates were collected by filtration and dried to give 7-[2-methoxyimino-2-(2-methyl-1,3-thiazol-4-yl)acetamido]-3-(1-methyl-1H-tetrazol-5-yl)thiomethyl-3-cephem-4-carboxylic acid (syn isomer) (0.28 g.).

I.R. spectrum (Nujol): 1780, 1710, 1675 cm$^{-1}$.

N.M.R spectrum (d$_6$-DMSO, $\delta$): ppm: 9.65 (1H, d, J=10 Hz); 7.66 (1H, s); 5.81 (1H, dd, J=5,10 Hz); 5.15 (1H, d, J=5 Hz); 4.31 (2H, AB$_q$, J=13 Hz); 3.93 (3H, s); 3.90 (3H, s); 3.70 (2H, AB$_q$, J=16 Hz); 2.65 (3H, s).

EXAMPLE 12

Phosphorus oxychloride (0.89 g.) and dry dimethylformamide (0.44 g.) were mixed under ice-cooling and then warmed for 30 minutes at 40° C. Dry methylene chloride (20 ml.) was added thereto and then distilled off. To the residue were added dry ethyl acetate (10 ml.) and then 2-methoxyimino-2-[2-(2,2,2-trifluoroacetamido)-1,3-thiazol-4-yl]acetic acid (syn isomer) (1.8 g.) with stirring and ice-cooling. The mixture was stirred for 40 minutes at the same temperature to give clear solution. On the other hand, trimethylsilylacetamide (6.36 g.) was added to a suspension of 7-aminocephalosporanic acid (1.65 g.) in dry ethyl acetate (25 ml.) with stirring at ambient temperature, after which the mixture was stirred for 1 hour to give a clear solution. To this solution was at a time added the above-obtained ethyl acetate solution with stirring at $-20°$ to $-25°$ C., and the resulting mixture was stirred for 2 hours at the same temperature. Water (30 ml.) was added to the reaction mixture at the same temperature, and then the mixture was stirred for 5 minutes at ambient temperature. The ethyl acetate layer was separated, and the aqueous layer was further extracted with ethyl acetate. The ethyl acetate layers were combined and water (50 ml.) was added thereto. The mixture was adjusted to pH 7.5 with sodium bicarbonate, and the aqueous layer was separated. Ethyl acetate (40 ml.) was added to the aqueous layer, and the mixture was adjusted to pH 2.5 with 10% hydrochloric acid with stirring and ice-cooling. The ethyl acetate layer was separated, and the aqueous layer was further extracted twice with ethyl acetate (30 ml.). The ethyl acetate layers were combined, washed with an aqueous solution of sodium chloride and treated with activated charcoal. The solvent was distilled off to give 7-[2-methoxyimino-2-{2-(2,2,2-trifluoroacetamido)-1,3-thiazol-4-yl}acetamido]cephalosporanic acid (syn isomer) (3.05 g.), mp 205° C. (dec.).

I.R. spectrum (Nujol): 3250, 1790, 1735, 1680, 1650 cm$^{-1}$.

N.M.R. spectrum (d$_6$-DMSO, $\delta$): ppm: 9.8 (1H, d, J=8 Hz); 7.55 (1H, s); 5.88 (1H, dd, J=5,8 Hz); 5.25 (1H, d, J=5 Hz); 4.8 (2H, AB$_q$, J=13 Hz); 3.95 (3H, s); 3.59 (2H, broad s); 2.03 (3H, s).

EXAMPLE 13

Phosphorus oxychloride (2.0 g.) was at a time added at 5° to 10° C. to a suspension of 2-methoxyimino-2-(2-amino-1,3-thiazol-4-yl)acetic acid (syn isomer) (2 g.) in dry ethyl acetate (20 ml.). After stirring for 20 minutes at 7° to 10° C., bis(trimethylsilyl)acetamide (0.4 g.) was added thereto at the same temperature. After stirring for 10 minutes at 7° to 10° C., phosphorus oxychloride (2.0 g.) was dropwise added thereto at the same temperature. The resulting mixture was stirred for 10 minutes at 7° to 10° C., and dry dimethylformamide (0.8 g.) was dropwise added thereto at the same temperature. The mixture was stirred for 30 minutes at 7° to 10° C. to give a clear solution. On the other hand, trimethylsilylacetamide (7.35 g.) was added to a suspension of 7-aminocephalosporanic acid (2.45 g.) in dry ethyl acetate (8 ml.), after which the mixture was stirred at 40° C. to give a clear solution. To this solution was at a time added the above-obtained ethyl acetate solution at $-15°$ C., and the resulting mixture was stirred for 1 hour at $-10°$ to $-15°$ C. The reaction mixture was cooled to $-30°$ C., and water (80 ml.) was added thereto. The aqueous layer was separated, adjusted to pH 4.5 with sodium bicarbonate and subjected to column chromatography on Diaion HP-20 resin (Trademark: prepared by Mitsubishi Chemical Industries Ltd.) using 25% aqueous solution of isopropyl alcohol as an eluent. The eluate was lyophilized to give 7-[2-methoxyimino-2-(2-amino-1,3-thiazol-4-yl)acetamido]cephalosporanic acid (syn isomer) (1.8 g.), mp 227° C. (dec.).

I.R. spectrum (Nujol): 3300-3350, 1780, 1740, 1670 cm$^{-1}$.

N.M.R. spectrum (d$_6$-DMSO, $\delta$): ppm: 9.6 (1H, d, J=8 Hz); 6.8 (1H, s); 5.8 (1H, dd, J=5,8 Hz); 5.2 (1H, d, J=5 Hz); 4.87 (2H, AB$_q$, J=13 Hz); 3.89 (3H, s); 3.6 (2H, broad s); 2.08 (3H, s).

EXAMPLE 14

Phosphorus oxychloride (3.8 g.) was dropwise added at 5° to 8° C. to a suspension of 2-methoxyimino-2-(2-amino-1,3-thiazol-4-yl)acetic acid (syn isomer) (4.0 g.) in dry ethyl acetate (40 ml.). After stirring for 30 minutes around 5° C., bis(trimethylsilyl)acetamide (0.86 g.) was added thereto at the same temperature. After stirring for 10 minutes at the same temperature, phosphorus oxychloride (3.8 g.) was dropwise added thereto at 5° to 8° C., after which the mixture was stirred for 30 minutes at the same temperature. Dry dimethylformamide (1.6 g.) was dropwise added thereto at 5° to 7° C., after which the resulting mixture was stirred for 30 minutes at the same temperature to give a clear solution. On the other hand, sodium acetate (3.3 g.) was added to a solution of 7-aminocephalosporanic acid (2.7 g.) in an aqueous solution (20 ml.) of sodium bicarbonate (1.7 g.), and then acetone (20 ml.) was added thereto. To this solution was dropwise added the above-obtained ethyl acetate solution with stirring at 0° to 5° C. keeping the pH of this solution at 7.0 to 7.5 by 20% aqueous solution of sodium carbonate. The mixture was stirred for 1 hour at the same temperature. An insoluble material was filtered off, and the aqueous layer in the filtrate was separated. The aqueous layer was concentrated under reduced pressure to remove the organic solvents, adjusted to pH 4.5 with sodium bicarbonate and subjected to column chromatography on Diaion HP-20 resin (Trademark: prepared by Mitsubishi Chemical Industries Ltd.) using 25% aqueous solution of isopropyl alcohol as an eluent. The eluate was lyophilized to give 7-[2-methoxyimino-2-(2-amino-1,3-thiazol-4-yl)acetamido]cephalosporanic acid (syn isomer) (2.8 g.). This compound was identified with the compound obtained in Example 13 by I.R. and N.M.R. spectra.

EXAMPLE 15

The following compounds were obtained according to similar manners to those of Examples 11 to 14.

(1) 7-[2-Methoxyimino-2-(2-mesylimino-3-methyl-2,3-dihydro-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3250, 1780, 1718, 1675 cm$^{-1}$.

N.M.R. spectrum (d$_6$-DMSO, $\delta$): ppm: 9.80 (1H, d, J=8 Hz); 7.08 (1H, s); 5.80 (1H, dd, J=5,8 Hz); 5.18 (1H, d, J=5 Hz); 4.34 (2H, AB$_q$, J=13 Hz); 3.99 (3H, s); 3.96 (3H, s); 3.72 (2H, AB$_q$, J=17 Hz); 3.66 (3H, s); 2.98 (3H, s).

(2) 7-[2-Methoxyimino-2-(2-mesylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3300-3150, 1780, 1710, 1670 cm$^{-1}$.

N.M.R. spectrum (d$_6$-DMSO, $\delta$): ppm: 9.84 (1H, d, J=8 Hz); 6.97 (1H, s); 5.76 (1H, dd, J=5,8 Hz); 5.12 (1H, d, J=5 Hz); 4.33 (2H, AB$_q$, J=13 Hz); 3.93 (6H, s); 3.74 (2H, AB$_q$, J=17 Hz); 2.96 (3H, s).

(3) 7-Methoxyimino-2-(2-oxo-2,3-dihydro-1,3-thiazol-4-yl)acetamido]-3-(1-methyl-1H-tetrazol-5-yl)thiomethyl-3-cephem-4-carboxylic acid (syn isomer).

I.R. spectrum (Nujol): 1780, 1665 cm$^{-1}$.

N.M.R. spectrum (d6-DMSO, δ): ppm: 11.67 (1H, s); 9.83 (1H, d, J=8 Hz); 6.61 (1H, s); 5.80 (1H, dd, J=5,8 Hz); 5.17 (1H, d, J=5.5 Hz); 4.37 (2H, broad s); 4.00 (3H, s); 3.96 (3H, s); 3.75 (2H, broad s).

(4) 7-[2-Methoxyimino-2-{2-(2,2,2-trifluoroacetamido)-1,3-thiazol-4-yl}acetamido]-3-(1-methyl-1H-tetrazol-5-yl)thiomethyl-3-cephem-4-carboxylic acid (syn isomer).

I.R. spectrum (Nujol): 1790, 1730, 1660 cm$^{-1}$.

N.M.R. spectrum (d6-DMSO, δ): ppm: 9.73 (1H, d, J=8 Hz); 7.53 (1H, s); 5.83 (1H, dd, J=5,8 Hz); 5.15 (1H, d, J=5 Hz); 4.33 (2H, broad s); 3.93 (6H, s); 3.72 (2H, broad s).

(5) 7-[2-Methoxyimino-2-(2-t-pentyloxycarbonylamino-1,3-thiazol-4-yl)acetamido]-3-(5-methyl-1,3,4-thiadiazol-2-yl)-thiomethyl-3-cephem-4-carboxylic acid (syn isomer).

I.R. spectrum (Nujol): 3200, 1780, 1720, 1680 cm$^{-1}$.

N.M.R. spectrum (d6-DMSO, δ): ppm: 9.65 (1H, d, J=8 Hz); 7.28 (1H, s); 5.80 (1H, dd, J=5,8 Hz); 5.16 (1H, d, J=5 Hz); 4.38 (2H, AB$_q$, J=13 Hz); 3.86 (3H, s); 3.70 (2H, AB$_q$, J=17 Hz); 2.66 (3H, s); 1.78 (2H, q, J=8 Hz); 1.44 (6H, s); 0.88 (3H, t, J=8 Hz).

(6) 7-[2-Allyloxyimino-2-(2-mesylamino-1,3-thiazol-4-yl)-acetamido]-3-(1-methyl-1H-tetrazol-5-yl)thiomethyl-3-cephem-4-carboxylic acid (syn isomer).

I.R. spectrum (Nujol): 3100–3300, 1780, 1720, 1675 cm$^{-1}$.

N.M.R. spectrum (d6-DMSO, δ): ppm: 9.90 (1H, d, J=8 Hz); 7.00 (1H, s); 6.07–5.63 (2H, m); 5.43 (2H, d, J=8 Hz); 5.18 (1H, d, J=5 Hz); 4.70 (2H, d, J=5 Hz); 4.37 (2H, broad s); 3.98 (3H, s); 3.75 (2H, broad s); 3.00 (3H, s).

(7) 7-[2-Allyloxyimino-2-(2-t-pentyloxycarbonylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3250, 1780, 1720, 1678, 1625 cm$^{-1}$.

N.M.R. spectrum (d6-DMSO,δ): ppm: 9.74 (1H, d, J=8 Hz); 7.31 (1H, s); 6.28–5.76 (2H, m); 5.28 (2H, dd, J=8, 16 Hz); 5.18 (1H, d, J=5 Hz); 4.66 (2H, d, J=5 Hz); 4.36 (2H, ABq, J=13 Hz); 3.96 (3H, s); 3.74 (2H, ABq, J=17 Hz); 1.80 (2H, q, J=8 Hz); 1.45 (6H, s); 0.89 (3H, t, J=8 Hz).

(8) 7-[2-Methoxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200, 1765, 1600 cm$^{-1}$.

N.M.R. spectrum (d6-DMSO, δ): ppm: 9.51 (1H, d, J=8.5 Hz); 7.22 (2H, broad s); 6.72 (1H, s); 5.59 (1H, dd, J=5, 8.5 Hz); 5.00 (1H, d, J=5 Hz); 4.35 (2H, ABq, J=12 Hz); 3.90 (3H, s); 3.81 (3H, s); 3.55 (2H, ABq, J=18 Hz).

(9) 7-[2-Methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer).

I.R. spectrum (Nujol): 3400–3150, 1770, 1670, 1625 cm$^{-1}$.

N.M.R. spectrum (d6-DMSO, δ): ppm: 9.66 (1H, d, J=8 Hz); 7.34 (2H, broad s); 6.76 (1H, s); 5.78 (2H, dd, J=5,8 Hz); 5.16 (1H, d, J=5 Hz); 4.40 (2H, ABq, J=14 Hz); 3.85 (3H, s); 3.70 (2H, ABq, J=17 Hz); 2.68 (3H, s).

(10) 7-[2-Allyloxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100–3400, 1775, 1660, 1625 cm$^{-1}$.

N.M.R. spectrum (d6-DMSO, δ): ppm: 9.70 (1H, d, J=8 Hz); 6.80 (1H, s); 6.30–5.60 (2H, m); 5.24 (2H, dd, J=8,16 Hz); 5.15 (1H, d, J=5 Hz); 4.63 (2H, d, J=5 Hz); 4.32 (2H, ABq, J=12 Hz); 3.94 (3H, s); 3.70 (2H, ABq, J=17 Hz).

(11) 7-[2-Methoxyimino-2-(2-formamido-1,3-thiazol-4-yl)acetamido]-3-(1,3,4-thiadiazol-2-yl)thiomethyl-3-cephem-4-carboxylic acid (syn isomer), mp 145° to 147° C. (dec.).

I.R. spectrum (Nujol): 3150–3400, 1780, 1725, 1680, 1640 cm$^{-1}$.

N.M.R. spectrum (d6-DMSO, δ): ppm: 12.58 (1H, broad s); 9.70 (1H, d, J=8 Hz); 9.58 (1H, s); 8.50 (1H, s); 7.40 (1H, s); 5.82 (1H, dd, J=5,8 Hz); 5.17 (1H, d, J=5 Hz); 4.43 (2H, ABq, J=13 Hz); 3.88 (3H, s); 3.70 (2H, broad s).

(12) 7-[2-Methoxyimino-2-(2-acetamido-1,3-thiazol-4-yl)acetamido]-3-(1-methyl-1H-tetrazol-5-yl)thiomethyl-3-cephem-4-carboxylic acid (syn isomer), mp 171° to 173° C. (dec.).

I.R. spectrum (Nujol): 3500, 3250, 1780, 1720, 1670 cm$^{-1}$.

N.M.R. spectrum (d6-DMSO, δ): ppm: 9.65 (1H, d, J=8 Hz); 7.3 (1H, s); 5.8 (1H, dd, J=5, 8 Hz); 5.15 (1H, d, J=5 Hz); 4.35 (2H, broad s); 3.97 (3H, s); 3.9 (3H, s); 3.75 (2H, broad s); 2.15 (3H, s).

(13) 7-[2-Methoxyimino-2-{2-(2,2,2-trifluoroacetamido)-1,3-thiazol-4-yl}acetamido]-cephalosporanic acid (syn isomer), mp 205° C. (dec.).

I.R. spectrum (Nujol): 3250, 1790, 1735, 1680, 1650 cm$^{-1}$.

N.M.R. spectrum (d6-DMSO, δ): ppm: 9.8 (1H, d, J=8 Hz); 7.55 (1H, s); 5.88 (1H, dd, J=5, 8 Hz); 5.25 (1H, d, J=5 Hz); 4.8 (2H, ABq, J=13 Hz); 3.95 (3H, s); 3.59 (2H, broad s); 2.03 (3H, s).

(14) 7-[2-Methoxyimino-2-{2-(2,2,2-trifluoroacetamido)-1,3 thiazol-4-yl}acetamido]-3-carbamoyloxymethyl-3-cephem-4-carboxylic acid (syn isomer).

I.R. spectrum (Nujol): 3500, 3200, 1785, 1700, 1660 cm$^{-1}$.

N.M.R. spectrum (d6-DMSO, δ): ppm: 9.75 (1H, d, J=8 Hz); 8.4 (2H, m); 7.53 (1H, s); 6.6 (1H, m); 6.20 (1H, d, J=5 Hz); 5.83 (1H, m); 4.77 (2H, ABq, J=14 Hz); 3.91 (3H, s); 3.55 (2H, m).

(15) 7-[2-Methoxyimino-2-{2-(2,2,2-trifluoroacetamido)-1,3-thiazol-4-yl}acetamido]-3-(1,3,4-thiadiazol-2-yl)thiomethyl-3-cephem-4-carboxylic acid (syn isomer).

I.R. spectrum (Nujol): 3200, 1780, 1720, 1650 cm$^{-1}$.

N.M.R. spectrum (d6-DMSO, δ): ppm: 9.81 (1H, d, J=8 Hz); 9.6 (1H, m); 9.57 (1H, s); 7.56 (1H, s); 5.83 (1H, dd, J=5, 8 Hz); 5.20 (1H, d, J=5 Hz); 4.47 (2H, ABq, J=14 Hz); 3.96 (3H, s); 3.72 (2H, ABq, J=18 Hz).

(16) 7-[2-Methoxyimino-2-(2-amino-1,3-thiazol-4-yl)acetamido]-3-hydroxymethyl-3-cephem-4-carboxylic acid (syn isomer), mp 260° to 270° C. (dec.).

I.R. spectrum (Nujol): 3370, 3270, 1765, 1660, 1610, 1590, 1550 cm$^{-1}$.

N.M.R. spectrum (d6-DMSO, δ): ppm: 9.58 (1H, d, J=8 Hz); 6.76 (1H, s); 5.75 (1H, dd, J=5, 8 Hz); 5.12 (1H, d, J=5 Hz); 4.27 (2H, broad s); 3.85 (3H, s); 3.57 (2H, broad s).

(17) 7-[2-Methoxyimino-2-(2-amino-1,3-thiazol-4-yl)acetamido]-cephalosporanic acid (syn isomer), mp 227° C. (dec.).

I.R. spectrum (Nujol): 3300–3350, 1780, 1740, 1670 cm$^{-1}$.

N.M.R. spectrum (d6-DMSO, δ): ppm: 9.6 (1H, d, J=8 Hz); 6.8 (1H, s); 5.8 (1H, dd, J=5, 8 Hz); 5.2 (1H, d, J=5 Hz); 4.87 (2H, ABq, J=13 Hz); 3.89 (3H, s); 3.6 (2H, broad s); 2.08 (3H, s).

(18) 7-[2-Methoxyimino-2-(2-amino-1,3-thiazol-4-yl)acetamido]-3-carbamoyloxymethyl-3-cepham-4-carboxylic acid (syn isomer), mp 210° to 220° C. (dec.).

I.R. spectrum (Nujol): 3250, 1765, 1650 cm$^{-1}$.

N.M.R. spectrum (d6-DMSO, δ): ppm: 9.64 (1H, d, J=8 Hz); 7.4 (2H, m); 6.79 (1H, s); 6.60 (2H, m); 5.77 (1H, dd, J=5, 8 Hz); 5.16 (1H, d, J=5 Hz); 4.75 (2H, ABq, J=12 Hz); 3.87 (3H, s); 3.53 (2H, ABq, J=18 Hz).

(19) 7-[2-Methoxyimino-2-(2-amino-1,3-thiazol-4-yl)acetamido]-3-(1,3,4-thiadiazol-2-yl)thiomethyl-3-cephem-4-carboxylic acid (syn isomer), mp 172° to 175° C. (dec.).

I.R. spectrum (Nujol): 3300, 1770, 1665 cm$^{-1}$.

N.M.R. spectrum (d6-DMSO, δ): ppm: 9.80 (1H, d, J=8 Hz); 9.63 (1H, s); 6.95 (1H, s); 6.8 (2H, m); 5.82 (1H, dd, J=5, 8 Hz); 5.22 (1H, d, J=5 Hz); 4.48 (2H, ABq, J=15 Hz); 3.97 (3H, s); 3.76 (2H, ABq, J=18 Hz).

(20) 7-[2-Methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer), mp 185° C. (dec.).

I.R. spectrum (Nujol): 3150–3350, 1770, 1710, 1660, 1630 cm$^{-1}$.

N.M.R. spectrum (d6-DMSO, δ): ppm: 9.61 (1H, d, J=8 Hz); 8.69 (1H, s); 6.73 (1H, s); 5.72 (1H, dd, J=4, 8 Hz); 5.1 (1H, d, J=4 Hz); 4.1 (2H, ABq, J=13 Hz); 3.87 (3H, s); 3.65 (2H, broad s); 3.59 (3H, s).

(21) 7-[2-Methoxyimino-2-{2-(2,2,2-trifluoroacetamido)-1,3-thiazol-4-yl}acetamido]-3-hydroxymethyl-3-cephem-4-carboxylic acid (syn isomer), mp 155° to 160° C. (dec.).

I.R. spectrum (Nujol): 3250, 1780, 1730, 1660, 1585, 1520 cm$^{-1}$.

N.M.R. spectrum (d6-DMSO, δ): ppm: 9.76 (1H, d, J=8 Hz); 7.57 (1H, s); 5.80 (1H, dd, J=4, 8 Hz); 5.15 (1H, d, J=4 Hz); 4.29 (2H, s); 3.93 (3H, s); 3.60 (2H, s).

(22) 6-[2-Methoxyimino-2-(2-amino-1,3-thiazol-4-yl)acetamido]-5a, 6-dihydro-3H,7H-azeto[2,1-b]furo[3,4-d][1,3]thiazine-1,7(4H)-dione (syn isomer), mp 210° to 215° C. (dec.).

I.R. spectrum (Nujol): 3270, 1780, 1740, 1655, 1610, 1525 cm$^{-1}$.

N.M.R. spectrum (d6-DMSO, δ): ppm: 9.70 (1H, d, J=8 Hz); 7.26 (2H, broad s); 6.77 (1H, s); 5.93 (1H, dd, J=5, 8 Hz); 5.16 (1H, d, J=5 Hz); 5.05 (2H, broad s); 3.85 (3H, s); 3.81 (2H, broad s).

(23) 7-[2-Methoxyimino-2-(2-amino-1,3-thiazol-4-yl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d6-DMSO, δ): ppm: 9.56 (1H, d, J=8 Hz); 6.75 (1H, s); 5.75 (1H, m); 5.10 (1H, d, J=4 Hz); 4.58 (2H, broad s); 4.32 (2H, broad s); 3.82 (3H, s); 3.68 (2H, broad s); 3.20 (2H, broad s); 2.50 (6H, s).

(24) 7-[2-Methoxyimino-2-(2-formamido-1,3-thiazol-4-yl)acetamido]cephalosporanic acid (syn isomer).

I.R. spectrum (Nujol): 3280, 1785, 1740, 1700, 1650 cm$^{-1}$.

N.M.R. spectrum (d6-DMSO, δ): ppm: 12.68 (1H, broad s); 9.68 (1H, d, J=8 Hz); 8.54 (1H, s); 7.45 (1H, s); 5.86 (1H, dd, J=5,8 Hz); 5.20 (1H, d, J=5 Hz); 4.90 (2H, ABq, J=8 Hz); 3.61 (3H, broad s); 2.06 (3H, s).

(25) 7-[2-Methoxyimino-2-(2-ethoxycarbonylamino-1,3-thiazol-4-yl)acetamido]-3-(1,3,4-thiadiazol-2-yl)thiomethyl-3-cephem-4-carboxylic acid (syn isomer).

I.R. specetum (Nujol): 3200, 1775, 1720, 1680, 1660 cm$^{-1}$.

N.M.R. spectrum (d6-DMSO, δ): ppm: 11.9 (1H, m); 9.70 (1H, d, J=10 Hz); 9.55 (1H, s); 7.31 (1H, s); 5.80 (1H, dd, J=5,10 Hz); 5.18 (1H, d,J=5 Hz); 4.44 (2H, AB$_q$, J=16 Hz); 4.22 (2H, q, J=7 Hz); 3.89 (3H, s); 3.72 (2H, AB$_q$, J=16 Hz); 1.23 (3H, t, J=7 Hz).

(26) 7-[2-Methoxyimino-2-{2-(2,2,2-trifluoroacetamido)-1,3-thiazol-4-yl}acetamido]-3-formyl-3-cephem-4-carboxylic acid (syn isomer) [or this compound can be represented as 3-hydroxy-6-[2-methoxyimino-2-{2-(2,2,2-trifluoroacetamido)-1,3-thiazol-4-yl}acetamido]-5$_a$,6-dihydro-3H,7H-azeto[2,1-b]furo[3,4-d][1,3]thiazine-1,7(4H)dione (syn isomer)].

I.R. spectrum (Nujol): 3150, 1790, 1720, 1655, 1560, 1500 cm$^{-1}$.

N.M.R. spectrum (d6-DMSO, δ): ppm: 9.88 (1H, d, J=8 Hz); 7.60 (1H, s); 6.30 (1H, d, J=6 Hz); 6.05 (1H, dd, J=5,8 Hz); 5.23 (1H, d, J=5 Hz); 3.96 (3H, s); 3.80 (2H, broad s).

(27) 7-[2-Methoxyimino-2-(2-formamido-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200–3300, 2600, 1780, 1720, 1690, 1675 cm$^{-1}$.

N.M.R. spectrum (d6-DMSO, δ): ppm: 12.60 (1H, broad s); 9.70 (1H, d, J=8 Hz); 8.50 (1H, s); 7.44 (1H, s); 5.88 (1H, dd, J=5,8 Hz); 5.19 (1H, d, J=5 Hz); 4.25 (2H, AB$_q$, J=13 Hz); 3.95 (3H, s); 3.85 (3H, s); 3.65 (2H, AB$_q$, J=18 Hz).

(28) 7-[2-Methoxyimino-2-(2-formamido-1,3-thiazol-4-yl)acetamido]-3-carbamoyloxymethyl-3-cephem-4-carboxylic acid (syn isomer).

I.R. spectrum (Nujol): 3300, 1780, 1705, 1680 cm$^{-1}$.

N.M.R. spectrum (d6-DMSO, δ): ppm: 12.50 (1H, broad s); 9.67 (1H, d, J=8 Hz); 8.50 (1H, s); 7.43 (1H, s); 6.58 (2H, broad s); 5.80 (1H, dd, J=5, 8 Hz); 5.16 (1H, d, J=5 Hz); 4.78 (2H, AB$_q$, J=14 Hz); 3.95 (3H, s); 3.57 (2H, AB$_q$, J=18 Hz).

EXAMPLE 16

A solution of 7-[2-methoxyimino-2-{2-(2,2,2-trifluoroacetamido)-1,3-thiazol-4-yl}acetamido]-3-(1-methyl-1H-tetrazol-5-yl)thiomethyl-3-cephem-4-carboxylic acid (syn isomer) (0.3 g.) in a 0.1 N aqueous solution of sodium hydroxide (10.5 ml.) was warmed at 45° C. for 6 hours. Water (15 ml.) and ethyl acetate (30 ml.) were added to the reaction mixture and the resulting mixture was adjusted to pH 3.5 with 10% hydrochloric acid. The aqueous layer was separated, washed with ethyl acetate and adjusted to pH 5.0 with an aqueous solution of sodium bicarbonate. The aqueous solution was subjected to column chromatography on Amberlite XAD-2 (20 ml.) (prepared by Rohm & Haas Co.) using 10% ethanol as developing solvent. The eluate containing object compound was collected and lyophilized to give 7-[2-methoxyimino-2-(2-amino-1,3-thiazol-4-yl)acetamido]-3-(1-methyl-1H-tetrazol-5-yl)thiomethyl-3-cephem-4-carboxylic acid (syn isomer) (0.12 g.).

IR. spectrum (Nujol): 3200, 1765, 1600 cm$^{-1}$.

N.M.R. spectrum (d$_6$-DMSO, δ): ppm: 9.51 (1H, d, J=8.5 Hz); 7.22 (2H, broad s); 6.72 (1H, s); 5.59 (1H, dd, J=5, 8.5 Hz); 5.00 (1H, d, J=5 Hz); 4.35 (2H, AB$_q$, J=12 Hz); 3.90 (3H, s); 3.81 (3H, s); 3.55 (2H, AB$_q$, J=18 Hz).

EXAMPLE 17

Trifluoroacetic acid (3 ml) was added under ice-cooling to 7-[2-methoxyimino-2-(2-t-pentyloxycarbonylamino-1,3-thiazol-4-yl)acetamido]-3-(5-methyl-1,3,4-thiadiazol-2-yl)-thiomethyl-3-cephem-4-carboxylic acid (syn isomer) (0.5 g) and the mixture was stirred for 30 minutes at ambient temperature. To the mixture was added ether and precipitating powder was collected by filtration and dissolved in a mixture of water (20 ml) and an 1 N aqueous solution of sodium hydroxide to adjust to pH 12 to 13. The solution was adjusted to pH 4.6 with 10% hydrochloric acid, washed with ethyl acetate and methylene chloride. Excess methylene chloride in the aqueous layer was thoroughly removed by bubbling of nitrogen gas. The aqueous layer was adjusted to pH 2 with stirring and ice-cooling to precipitate powder. The powder was collected by filtration and dried to give 7-[2-methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer) (0.128 g)

I.R. spectrum (Nujol): 3400–3150, 1770, 1670, 1625 cm$^{-1}$.

N.M.R. spectrum (d$_6$-DMSO, δ): ppm: 9.66 (1H, d, J=8 Hz); 7.34 (2H, broad s); 6.76 (1H, s); 5.78 (2H, dd, J=5, 8 Hz); 5.16 (1H, d, J=5 Hz); 4.40 (2H, ABq, J=14 Hz); 3.85 (3H, s); 3.70 (2H, ABq, J=17 Hz); 2.68 (3H, s).

EXAMPLE 18

Trifluoroacetic acid (4 ml.) and anisole (2 ml.) were added under ice-cooling to 7-[2-allyloxyimino-2-(2-t-pentyloxycarbonylamino-1,3-thiazol-4-yl)acetamido]-3-(1-methyl-1H-tetrazol-5-yl)thiomethyl-3-cephem-4-carboxylic acid (syn isomer) (0.9 g.) and the mixture was stirred for 40 minutes at ambient temperature. The reaction mixture was post-treated according to a similar manner to that of Example 17 to give 7-[2-allyloxyimino-2-(2-amino-1,3-thiazol-4-yl)acetamido]-3-(1-methyl-1H-tetrazol-5-yl)thiomethyl-3-cephem-4-carboxylic acid (syn isomer) (0.425 g.).

I.R. spectrum (Nujol): 3100–3400, 1775, 1660, 1625 cm$^{-1}$.

N.M.R. spectrum (d$_6$-DMSO, δ): ppm: 9.70 (1H, d, J=8 Hz); 6.80 (1H, s); 6.30–5.60 (2H, m); 5.24 (2H, dd, J=8, 16 Hz); 5.15 (1H, d, J=5 Hz); 4.63 (2H, d, J=5 Hz); 4.32 (2H, AB$_q$, J=12 Hz); 3.94 (3H, s); 3.70 (2H, AB$_q$, J=17 Hz).

EXAMPLE 19

Disodium hydrogen phosphate (0.26 g) was added to a suspension of 7-[2-methoxyimino-2-{2-(2,2,2-trifluoroacetamido)-1,3-thiazol-4-yl}acetamido]cephalosporanic acid (syn isomer) (1 g) in water (15 ml). A saturated aqueous solution of disodium hydrogen phosphate was further added thereto to adjust the pH value of the mixture at 6. The resulting mixture was stirred for 23 hours at ambient temperature. The reaction mixture was adjusted to pH 4 under ice-cooling with 10% hydrochloric acid, washed with ethyl acetate and adjusted to pH 2.5 with 10% hydrochloric acid. Precipitating crystals were collected by filtration, washed with cold water and dried to give 7-[2-methoxyimino-2-(2-amino-1,3-thiazol-4-yl)acetamido]cephalosporanic acid (syn isomer) (0.18 g), mp 227° C. (dec.).

I.R. spectrum (Nujol): 3300–3350, 1780, 1740, 1670 cm$^{-1}$.

N.M.R. spectrum (d$_6$-DMSO, δ): ppm: 9.6 (1H, d, J=8 Hz); 6.8 (1H, s); 5.8 (1H, dd, J=5, 8 Hz); 5.2 (1H, d, J=5 Hz); 4.87 (2H, ABq, J=13 Hz); 3.89 (3H, s); 3.6 (2H, broad s); 2.08 (3H, s).

EXAMPLE 20

7-[2-Methoxyimino-2-{2-(2,2,2-trifluoroacetamido)-1,3-thiazol-4-yl}acetamido]-3-(1,3,4-thiadiazol-2-yl)thiomethyl-3-cephem-4-carboxylic acid (syn isomer) (23 g) was suspended in a solution of sodium acetate trihydrate (74.8 g) in water (230 ml) and the suspension was stirred for 15 hours at ambient temperature. The reaction mixture was adjusted to pH 5.0 with conc. hydrochloric acid and insoluble material was filtered off. The filtrate was adjusted to pH 2.5 and precipitating crystals were collected by filtration and dried to give 7-[2-methoxyimino-2-(2-amino-1,3-thiazol-4-yl)acetamido]-3-(1,3,4-thiadiazol-2-yl)thiomethyl-3-cephem-4-carboxylic acid (syn isomer) (14 g), mp 172° to 175° C. (dec.).

I.R. spectrum (Nujol): 3300, 1770, 1665 cm$^{-1}$.

N.M.R. spectrum (d$_6$-DMSO, δ): ppm: 9.80 (1H, d, J=8 Hz); 9.63 (1H, s); 6.95 (1H, s); 6.8 (2H, m); 5.82 (1H, dd, J=5, 8 Hz); 5.22 (1H, d, J=5 Hz); 4.48 (2H, ABq, J=15 Hz); 3.97 (3H, s); 3.76 (2H, ABq, J=18 Hz).

EXAMPLE 21

7-[2-Methoxyimino-2-{2-(2,2,2-trifluoroacetamido)-1,3-thiazol-4-yl}acetamido]-3-carbamoyloxymethyl-3-cephem-4-carboxylic acid (syn isomer) (3.5 g.) was suspended in a solution of sodium acetate trihydrate (12.2 g.) in water (30 ml.). The mixture was stirred for 15 hours at ambient temperature. The reaction mixture was saturated with sodium chloride and adjusted to pH 5.0 with conc. hydrochloric acid with stirring and ice-cooling. Precipitating insoluble material was filtered off. The filtrate was adjusted to pH 3.0 with conc. hydrochloric acid and further adjusted to pH 1.5 with 10% hydrochloric acid. Precipitates were collected by filtration and dried to give 7-[2-methoxyimino-2-(2-amino-1,3-thiazol-4-yl)acetamido]-3-carbamoyloxymethyl-3-cephem-4-carboxylic acid (syn isomer) (2.1 g.), mp 210° to 220° C. (dec.).

I.R. spectrum (Nujol): 3250, 1765, 1650 cm$^{-1}$.

N.M.R. spectrum (d$_6$-DMSO, δ): ppm: 9.64 (1H, d, J=8 Hz); 7.4 (2H, m); 6.79 (1H, s); 6.60 (2H, m); 5.77 (1H, dd, J=5, 8 Hz); 5.16 (1H, d, J=5 Hz); 4.75 (2H, AB$_q$, J=12 Hz); 3.87 (3H, s); 3.53 (2H, AB$_q$, J=18 Hz).

EXAMPLE 22

Conc. hydrochloric acid (10.4 ml.) was added with stirring at ambient temperature to a suspension of 7-[2-methoxyimino-2-(2-formamido-1,3-thiazol-4-yl)acetamido]cephalosporanic acid (syn isomer) (48.35 g.) in methanol (725 ml.). After stirring for 3 hours at ambient temperature, the reaction mixture was adjusted to pH 4.5 with aqueous solution of ammonia and methanol was distilled off. To the residue was added water (100 ml). The mixture was adjusted to pH 6.5 with an aqueous solution of sodium bicarbonate, and insoluble material was collected by filtration to give 6-[2-methoxyimino-2-(2-amino-1,3-thiazol-4-yl)acetamido]-5a,6-dihydro-3H,7H-azeto[2,1-b]furo[3,4-d][1,3]-thiazine-1,7(4H)dione (syn isomer) (6.5 g.). The filtrate was adjusted to pH 4.5 with acetic acid, adsorbed by Diaion HP-20 resin (Trademark: prepered by Mitsubishi Chemical Industries Ltd.) (600 ml.), washed with water (2 l.) and then eluted with 25% aqueous solution of isopropyl alcohol. Eluates containing the object compounds were collected and cooled after addition of isopropyl alcohol (⅓ volume of the eluates). Precipitates were collected by filtration, washed with isopropyl alcohol and dried to give 7-[2-methoxyimino-2-(2-amino-1,3-thiazol-4-yl)-acetamido]cephalosporanic acid (syn isomer) (10.4 g.). The mother liquor was concentrated under reduced pressure until crystals began to precipitate. To the residue was added isopropyl alcohol (⅔ volume of the residue). The mixture was cooled and precipitates were collected by filtration to give the same object compound (5.8 g.). Total yield (16.2 g.). This compound was identified with the compound obtained in the foregoing Examples by I.R. and N.M.R. spectra.

EXAMPLE 23

7-[2-Methoxyimino-2-(2-formamido-1,3-thiazol-4-yl)-acetamido]-3-(1,3,4-thiadiazol-2-yl)thiomethyl-3-cephem-4-carboxylic acid (syn isomer) (10.8 g.) was added to methanol (200 ml.), and phosphorus oxychloride (7.2 g.) was dropwise added thereto with stirring and ice-cooling at 2° to 9° C. After stirring for 1.5 hours at the same temperature, the reaction mixture was concentrated under reduced pressure on a water bath of 25° to 28° C. to the volume of 100 ml. To the residue was added ether (300 ml.) with stirring and ice-cooling. Precipitates were collected by filtration and dried to give 7-[2-methoxyimino-2-(2-amino-1,3-thiazol-4-yl)acetamido]-3-(1,3,4-thiadiazol-2-yl)-thiomethyl-3-cephem-4-carboxylic acid hydrochloride (syn isomer) (12.3 g.). This powder (12.3 g.) was suspended in water (100 ml.) and dissolved by adjusting pH of the suspension to 7.5 by addition of a saturated aqueous solution of sodium bicarbonate. To the solution was added ethyl acetate (100 ml.), and the mixture was adjusted to pH 2.5 with 10% hydrochloric acid. Precipitates were collected by filtration, washed with cold water and dried to give 7-[2-methoxyimino-2-(2-amino-1,3-thiazol-4-yl)acetamido]-3-(1,3,4-thiadiazol-2-yl)thiomethyl-3-cephem-4-carboxylic acid (syn isomer) (6.1 g.). The aqueous layer in the mother liquor was separated and stirred under cooling after addition of sodium chloride. Precipitates were collected by filtration to give the same object compound (3.8 g.). Total yield (9.9 g.). This compound was identified with the compound obtained in the foregoing Examples by I.R. and N.M.R. spectra.

EXAMPLE 24

The following compounds were obtained according to similar manners to those of Examples 16 to 23.

(1) 7-[2-Methoxyimino-2-(2-amino-1,3-thiazol-4-yl)acetamido]-3-hydroxymethyl-3-cephem-4-carboxylic acid (syn isomer), mp 260° to 270° C. (dec.).

I.R. spectrum (Nujol): 3370, 3270, 1765, 1660, 1610, 1590, 1550 cm$^{-1}$.

N.M.R. spectrum (d$_6$-DMSO, δ): ppm: 9.58 (1H, d, J=8 Hz); 6.76 (1H, s); 5.75 (1H, dd, J=5, 8 Hz); 5.12 (1H, d, J=5 Hz); 4.27 (2H, broad s); 3.85 (3H, s); 3.57 (2H, broad s).

(2) 7-[2-Methoxyimino-2-(2-amino-1,3-thiazol-4-yl)acetamido]-3-carbamoyloxymethyl-3-cephem-4-carboxylic acid (syn isomer), mp 210° to 220° C. (dec.).

I.R. spectrum (Nujol): 3250, 1765, 1650 cm$^{-1}$.

N.M.R. spectrum (d$_6$-DMSO, δ): ppm: 9.64 (1H, d, J=8 Hz); 7.4 (2H, m); 6.79 (1H, s); 6.60 (2H, m); 5.77 (1H, dd, J=5, 8 Hz); 5.16 (1H, d, J=5 Hz); 4.75 (2H, ABq, J=12 Hz); 3.87 (3H, s); 3.53 (2H, ABq, J=18 Hz);

(3) 7-[2-Methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer), mp 185° C. (dec.).

I.R. spectrum (Nujol): 3150-3350, 1770, 1710, 1660, 1630 cm$^{-1}$.

N.M.R. spectrum (d$_6$-DMSO, δ): ppm: 9.61 (1H, d, J=8 Hz); 8.69 (1H, s); 6.73 (1H. s); 5.72 (1H, dd, J=4, 8 Hz); 5.1 (1H, d, J=4 Hz); 4.1 (2H, ABq, J=13 Hz); 3.87 (3H, s); 3.65 (2H, broad s); 3.59 (3H, s).

(4) 6-[2-Methoxyimino-2-(2-amino-1,3-thiazol-4-yl)acetamido]-5a,6-dihydro-3H,7H-azeto[2,1-b]furo[3,4-d][1,3]thiazine-1,7(4H)-dione (syn isomer), mp 210° to 215° C. (dec.).

I.R. spectrum (Nujol): 3270, 1780, 1740, 1655, 1610, 1525 cm$^{-1}$.

N.M.R. spectrum (d$_6$-DMSO, δ): ppm: 9.70 (1H, d, J=8 Hz); 7.26 (2H, broad s); 6.77 (1H, s); 5.93 (1H, dd, J=5, 8 Hz); 5.16 (1H, d, J=5 Hz); 5.05 (2H, broad s); 3.85 (3H, s); 3.81 (2H, broad s).

(5) 7-[2-Methoxyimino-2-(2-amino-1,3-thiazol-4-yl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d$_6$-DMSO, δ): ppm: 9.56 (1H, d, J=8 Hz); 6.75 (1H, s); 5.75 (1H, m); 5.10 (1H, d, J=4 Hz); 4.58 (2H, broad s); 4.32 (2H, broad s); 3.82 (3H, s); 3.68 (2H, broad s); 3.20 (2H, broad s); 2.50 (6H, s).

EXAMPLE 25

A suspension of 7-[2-methoxyimino-2-{2-(2,2,2-trifluoroacetamido)-1,3-thiazol-4-yl}acetamido]cephalosporanic acid (syn isomer) (2.76 g) and 4-methyl-4H-1,2,4-triazole-3-thiol (0.63 g) in pH 6.4 phosphate buffer solution (50 ml) was adjusted to pH 6.4 with sodium bicarbonate and stirred for 6 hours at 65° to 70° C. The reaction mixture was cooled and ethyl acetate was added thereto. The mixture was adjusted to pH 5 with 10% hydrochloric acid and washed with ethyl acetate. The aqueous layer was treated with activated charcoal and adjusted to pH 2.7 with 10% hydrochloric acid with stirring and ice-cooling. Precipitating crystals were collected by filtration, washed with cold water and dried to give 7-[2-methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer) (0.7 g), mp 185° C. (dec.).

I.R. spectrum (Nujol): 3150-3350, 1770, 1710, 1660, 1630 cm$^{-1}$.

N.M.R. spectrum (d$_6$-DMSO, δ): ppm: 9.61 (1H, d, J=8 Hz); 8.69 (1H, s); 6.73 (1H, s); 5.72 (1H, dd, J=4, 8 Hz); 5.1 (1 H, d, J=4 Hz); 4.1 (2H, ABq, J=13 Hz); 3.87 (3H, s); 3.59 (3H, s); 3.65 (2H, broad s).

EXAMPLE 26

The following compounds were obtained according to a similar manner to that of Example 25.

(1) 7-[2-Methoxyimino-2-(2-methyl-1,3-thiazol-4-yl)acetamido]-3-(1-methyl-1H-tetrazol-5-yl)thiomethyl-3-cephem-4-carboxylic acid (syn isomer).

I.R. spectrum (Nujol): 1780, 1710, 1675 cm$^{-1}$.

N.M.R. spectrum (d$_6$-DMSO, δ): ppm: 9.65 (1H, d, J=10 Hz); 7.66 (1H, s); 5.81 (1H, dd, J=5, 10 Hz); 5.15 (1H, d, J=5 Hz); 4.31 (2H, ABq, J=13 Hz); 3.93 (3H, s); 3.90 (3H, s); 3.70 (2H, ABq, J=16 Hz); 2.65 (3H, s).

(2) 7-[2-Methoxyimino-2-(2-mesylimino-3-methyl-2,3-dihydro1,3-thiazol-4-yl)acetamido]-3-(1-methyl-1H-tetrazol-5-yl)thiomethyl-3-cephem-4-carboxylic acid (syn isomer).

I.R. spectrum (Nujol): 3250, 1780, 1718, 1675 cm$^{-1}$.

N.M.R. spectrum (d$_6$-DMSO, δ): ppm: 9.80 (1H, d, J=8 Hz); 7.08 (1H, s); 5.80 (1H, dd, J=5, 8 Hz); 5.18 (1H, d, J=5 Hz); 4.34 (2H, ABq, J=13 Hz); 3.99 (3H, s); 3.96 (3H, s); 3.72 (2H, ABq, J=17 Hz); 3.66 (3H, s); 2.98 (3H, s).

(3) 7-[2-Methoxyimino-2-(2mesylamino-1,3-thiazol-4-yl)-acetamido]-3-(1-methyl-1H-tetrazol-5-yl)thiomethyl-3-cephem-4-carboxylic acid (syn isomer).

I.R. spectrum (Nujol): 3300-3150, 1780, 1710, 1670 cm$^{-1}$.

N.M.R. spectrum (d$_6$-DMSO, δ): ppm: 9.84 (1H, d, J=8 Hz); 6.97 (1H, s); 5.76 (1H, dd, J=5, 8 Hz); 5.12 (1H, d, J=5 Hz); 4.33 (2H, ABq, J=13 Hz); 3.93 (6H, s); 3.74 (2H, ABq, J=17 Hz); 2.96 (3H, s).

(4) 7-[2-Methoxyimino-2-(2-oxo-2,3-dihydro-1,3-thiazol-4-yl)acetamido]-3-(1-methyl-1H-tetrazol-5-yl)thiomethyl-3-cephem-4-carboxylic acid (syn isomer).

I.R. spectrum (Nujol): 1780, 1665 cm$^{-1}$.

N.M.R. spectrum (d$_6$-DMSO, δ): ppm: 11.67 (1H, s); 9.83 (1H, d, J=8 Hz); 6.61 (1H, s); 5.80 (1H, dd, J=5.5, 8 Hz); 5.17 (1H, d, J=5.5 Hz); 4.37 (2H, broad s); 4.00 (3H, s); 3.96 (3H, s); 3.75 (2H, broad s).

(5) 7-[2-Allyloxyimino-2-(2-mesylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100-3300, 1780, 1720, 1675 cm$^{-1}$.

N.M.R. spectrum (d$_6$-DMSO, δ): ppm: 9.90 (1H, d, J=8 Hz); 7.00 (1H, s); 6.07-5.63 (2H, m); 5.43 (2H, d, J=8 Hz); 5.18 (1H, d, J=5 Hz); 4.70 (2H, d, J=5 Hz); 4.37 (2H, broad s); 3.98 (3H, s); 3.75 (2H, broad s); 3.00 (3H, s).

(6) 7-[2-Methoxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200, 1765, 1600 cm$^{-1}$.

N.M.R. spectrum (d$_6$-DMSO, δ): ppm: 9.51 (1H, d, J=8.5 Hz); 7.22 (2H, broad s); 6.72 (1H, s); 5.59 (1H, dd, J=5, 8.5 Hz); 5.00 (1H, d, J=5 Hz); 4.35 (2H, ABq, J=12 Hz); 3.90 (3H, s); 3.81 (3H, s); 3.55 (2H, ABq, J=18 Hz).

(7) 7-[2-Methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer).

I.R. spectrum (Nujol): 3400-3150, 1770, 1670, 1625 cm$^{-1}$.

N.M.R. spectrum (d$_6$-DMSO, δ): ppm: 9.66 (1H, d, J=8 Hz); 7.34 (2H, broad s); 6.76 (1H, s); 5.78 (2H, dd, J=5, 8 Hz); 5.16 (1H, d, J=5 Hz); 4.40 (2H, ABq, J=14 Hz); 3.85 (3H, s); 3.70 (2H, ABq, J=17 Hz); 2.68 (3H, s).

(8) 7-[2-Allyloxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100-3400, 1775, 1660, 1625 cm$^{-1}$.

N.M.R. spectrum (d$_6$-DMSO, δ): ppm: 9.70 (1H, d, J=8 Hz); 6.80 (1H, s); 6.30-5.60 (2H, m); 5.24 (2H, dd, J=8, 16 Hz); 5.15 (1H, d, J=5 Hz); 4.63 (2H, d, J=5 Hz); 4.32 (2H, ABq, J=12 Hz); 3.94 (3H, s); 3.70 (2H, ABq, J=17 Hz).

(9) 7-[2-Methoxyimino-2-(2-formamido-1,3-thiazol-4-yl)acetamido]-3-(1,3,4-thiadiazol-2-yl)thiomethyl-3-cephem-4-carboxylic acid (syn isomer), mp 145° to 147° C. (dec.).

I.R. spectrum (Nujol): 3150-3400, 1780, 1725, 1680, 1640 cm$^{-1}$.

N.M.R. spectrum (d$_6$-DMSO, δ): ppm: 12.58 (1H, broad s); 9.70 (1H, d, J=8 Hz); 9.58 (1H, s); 8.50 (1H, s); 7.40 (1H, s); 5.82 (1H, dd, J=5, 8 Hz); 5.17 (1H, d, J=5 Hz); 4.43 (2H, ABq, J=13 Hz); 3.88 (3H, s); 3.70 (2H, broad s).

(10) 7-[2-Methoxyimino-2-(2-acetamido-1,3-thiazol-4-yl)acetamido]-3-(1-methyl-1H-tetrazol-5-yl)thiomethyl-3-cephem-4-carboxylic acid (syn isomer), mp 171° to 173° C. (dec.).

I.R. spectrum (Nujol): 3500, 3250, 1780, 1720, 1670 cm$^{-1}$.

N.M.R. spectrum (d$_6$-DMSO, δ): ppm: 9.65 (1H, d, J=8 Hz); 7.3 (1H, s); 5.8 (1H, dd, J=5, 8 Hz); 5.15 (1H, d, J=5 Hz); 4.35 (2H, broad s); 3.97 (3H, s); 3.9 (3H, s); 3.75 (2H, broad s); 2.15 (3H, s).

(11) 7-[2-Methoxyimino-2-(2-amino-1,3-thiazol-4-yl)acetamido]-3-(1,3,4-thiadiazol-2-yl)thiomethyl-3-cephem-4-carboxylic acid (syn isomer), mp 172° to 175° C. (dec.).

I.R. spectrum (Nujol): 3300, 1770, 1665 cm$^{-1}$.

N.M.R. spectrum (d$_6$-DMSO, δ): ppm: 9.80 (1H, d, J=8 Hz); 9.63 (1H, s); 6.95 (1H, s); 6.8 (2H, m); 5.82 (1H, dd, J=5, 8 Hz); 5.22 (1H, d, J=5 Hz); 4.48 (2H, ABq, J=15 Hz); 3.97 (3H, s); 3.76 (2H, ABq, J=18 Hz).

(12) 7-[2-Methoxyimino-2-(2-amino-1,3-thiazol-4-yl)acetamido]-3-[1-(2-dimethylaminoethyl))-1H-tetrazol-5-yl]thiomethyl-3-cephem4-carboxylic acid (syn isomer).

I.R. spectrum (Nujol): 1765 cm$^{-1}$.

N.M.R. spectrum (d$_6$-DMSO, δ): ppm: 9.56 (1H, d, J=8 Hz); 6.75 (1H, s); 5.75 (1H, m); 5.10 (1H, d, J=4 Hz); 4.58 (2H, broad s); 4.32 (2H, broad s); 3.82 (3H, s); 3.68 (2H, broad s); 3.20 (2H, broad s); 2.50 (6H, s).

(13) 7-[2-Methoxyimino-2-(2-ethoxycarbonylamino-1,3-thiazol-4-yl)acetamido]-3-(1,3,4-thiadiazol-2-yl)thiomethyl-3-cephem-4-carboxylic acid (syn isomer).

I.R. spectrum (Nujol): 3200, 1775, 1720, 1680, 1660 cm$^{-1}$.

N.M.R. spectrum (d$_6$-DMSO, δ): ppm: 11.9 (1H, m); 9.70 (1H, d, J=10 Hz); 9.55 (1H, s); 7.31 (1H, s); 5.80 (1H, dd, J=5, 10 Hz); 4.44 (2H, AB$_q$, J=16 Hz); 4.22 (2H, q, J=7 Hz); 3.89 (3H, s); 3.72 (2H, AB$_q$, J=16 Hz); 1.23 (3H, t, J=7 Hz).

(14) 7-[2-Methoxyimino-2-(2-formamido-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200-3300, 2600, 1780, 1720, 1690, 1675 cm$^{-1}$.

N.M.R. spectrum (d$_6$-DMSO, δ): ppm: 12.60 (1H, broad s); 9.70 (1H, d, J=8 Hz); 8.50 (1H, s); 7.44 (1H, s); 5.88 (1H, dd, J=5, 8 Hz); 5.19 (1H, d, J=5 Hz); 4.25 (2H, AB$_q$, J=13 Hz); 3.95 (3H, s); 3.85 (3H, s); 3.65 (2H, AB$_q$, J=18 Hz).

(15) 7-[2-Methoxyimino-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3250, 1770, 1725, 1670 cm$^{-1}$.

N.M.R. spectrum (d$_6$-DMSO, δ): ppm: 9.76 (1H, d, J=8 Hz); 6.7-7.40 (4H, m); 5.86 (1H, dd, J=5, 8 Hz); 5.18 (1H, d, J=5 Hz); 4.34 (2H, ABq, J=13 Hz); 3.92 (6H, s); 3.72 (2H, ABq, J=17 Hz).

(16) 7-[2-t-Butoxycarbonylmethoxyimino-2-(3-chloro-4-hydroxyphenyl)acetamido]-3-(1-methyl-1H- tetrazol-5-yl)thiomethyl-3-cephem-4-carboxylic acid (syn isomer), powder.

(17) 7-[2-Carboxy-methoxyimino-2-(3-chloro-4-hydroxyphenyl)acetamido]-3-(1-methyl-1H-tetrazol-5-yl)thiomethyl-3-cephem-4-carboxylic acid (syn isomer), mp 145° to 148° C. (dec.).

I.R. spectrum (Nujol): 3400, 3200–3300, 2500–2600, 1780, 1720, 1670, 1600 cm$^{-1}$.

N.M.R. spectrum (d$_6$-DMSO, δ): ppm: 9.70 (1H, d, J=8 Hz); 7.50 (1H, d, J=2 Hz); 7.45 (1H, dd, J=2, 8 Hz); 7.10 (1H, d, J=8 Hz); 5.90 (1H, q, J=5 Hz); 5.22 (1H, d, J=5 Hz); 4.70 (2H, s); 4.35 (2H, ABq, J=13 Hz); 3.95 (3H, s); 3.75 (2H, ABq, J=18 Hz).

(18) 7-[2-(1-t-Butoxycarbonylethoxyimino)-2-(3-chloro-4-hydroxyphenyl)acetamido]-3-(1-methyl-1H-tetrazol-5-yl)thiomethyl-3-cephem-4-carboxylic acid (syn isomer), powder.

(19) 7-[2-(1-Carboxyethoxyimino)-2-(3-chloro-4-hydroxyphenyl)acetamido]-3-(1-methyl-1H-tetrazol-5-yl)thiomethyl-3-cephem-4-carboxylic acid (syn isomer), mp 147° to 151° C. (dec.).

I.R. spectrum (Nujol): 3500, 3250, 2500–2600, 1780, 1730, 1660, 1630, 1600 cm$^{-1}$.

N.M.R. spectrum (d$_6$-DMSO, δ): ppm: 9.62 (1H, d, J=8 Hz); 7.46 (1H, d, J=2 Hz); 7.34 (1H, dd, J=2, 8 Hz); 7.04 (1H, d, J=8 Hz); 5.90 (1H, q, J=5 Hz); 5.22 (1H, d, J=5 Hz); 4.73 (1H, q, J=6 Hz); 4.33 (2H, ABq, J=13 Hz); 4.00 (3H, s); 3.73 (2H, ABq, J=18 Hz); 1.37 (3H, d, J=6 Hz).

(20) 7-[2-Methoxyimino-2-(3-hydroxyphenyl)acetamido]-3-(4H-1,2,4-triazol-3-yl)thiomethyl-3-cephem-4-carboxylic acid (syn isomer).

I.R. spectrum (Nujol): 3250, 1775, 1710, 1665 cm$^{-1}$.

N.M.R. spectrum (d$_6$-DMSO, δ): ppm: 9.67 (1H, d, J=8 Hz); 8.40 (1H, s); 6.70–7.43 (4H, m); 5.82 (1H, dd, J=5, 8 Hz); 5.13 (1H, d, J=5 Hz); 4.18 (2H, ABq, J=13 Hz); 3.90 (3H, s); 3.67 (2H, broad s).

(21) 7-[2-Methoxyimino-2-(3-hydroxyphenyl)acetamido]-3-(1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ): ppm: 9.78 (1H, d, H=8 Hz); 9.55 (1H, s); 6.70–7.40 (4H, m); 5.89 (1H, dd, J=5, 8 Hz); 5.22 (1H, d, J=5 Hz); 4.46 (2H, ABq, J=13 Hz); 3.92 (3H, s); 3.76 (2H, ABq, J=18 Hz).

(22) 7-[2-Methoxyimino-2-(3-hydroxyphenyl)acetamido]-3-(5-methyl-1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ): ppm: 9.72 (1H, d, J=8 Hz); 6.62–7.40 (4H, m); 5.94 (1H, dd, J=5, 8 Hz); 5.18 (1H, d, J=5 Hz); 4.18 (2H, ABq, J=13 Hz); 3.89 (3H, s); 3.70 (2H, ABq, J=17 Hz); 2.65 (3H, s).

(23) 7-[2-Methoxyimino-2-(3-methoxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ): ppm: 9.78 (1H, d, J=8 Hz); 6.95–7.54 (4H, m); 5.94 (1H, dd, J=5, 8 Hz); 5.18 (1H, d, J=5 Hz); 4.12 (2H, ABq, J=13 Hz); 3.92 (6H, s); 3.76 (3H, s); 3.72 (2H, ABq, J=18 Hz).

(24) 7-[2-Methoxyimino-2-(4-hydroxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ): ppm: 9.70 (1H, d, J=8 Hz); 7.44 (2H, d, J=8 Hz); 6.84 (2H, d, J=8 Hz); 5.86 (1H, dd, J=5, 8 Hz); 5.18 (1H, d, J=5 Hz); 4.34 (2H, ABq, J=13 Hz); 3.93 (3H, s); 3.87 (3H, s); 3.74 (2H, ABq, J=18 Hz).

(25) 7-[2-Methoxyimino-2-(3-chloro-4-hydroxyphenyl)acetamido]-3-(1-methyl-1H-tetrazol-5-yl)thiomethyl-3-cephem-4-carboxylic acid (syn isomer), mp 145° to 148° C. (dec.).

I.R. spectrum (Nujol): 3500, 3250, 2500–2600, 1780, 1720, 1655, 1625, 1600 cm$^{-1}$.

N.M.R. spectrum (d$_6$-DMSO, δ): ppm: 10.80 (1H, broad s); 9.68 (1H, d, J=2 Hz); 7.46 (1H, d, J=2 Hz); 7.32 (1H, q, J=2, 8 Hz); 7.00 (1H, d, J=8 Hz); 5.80 (1H, q, J=5 Hz); 5.16 (1H, d, J=5 Hz); 4.28 (2H, ABq, J=13 Hz); 3.92 (3H, s); 3.87 (3H, s); 3.72 (2H, ABq, J=18 Hz).

(26) 7-[2-Methoxyimino-2-(3-chloro-4-methoxyphenyl)acetamido]-3-(1-methyl-1H-tetrazol-5-yl)thiomethyl-3-cephem-4-carboxylic acid (syn isomer), mp 143° to 145° C. (dec.).

I.R. spectrum (Nujol): 3300, 2500–2600, 1785, 1730, 1670, 1630, 1600 cm$^{-1}$.

N.M.R. spectrum (d$_6$-DMSO, δ): ppm: 9.76 (1H, d, J=8 Hz); 7.56 (1H, d, J=2 Hz); 7.48 (1H, dd, J=2, 8 Hz); 7.22 (1H, d, J=8 Hz); 5.84 (1H, q, J=5 Hz); 5.18 (1H, d, J=5 Hz); 4.27 (2H, ABq, J=13 Hz); 3.90 (6H, s); 3.88 (3H, s); 3.70 (2H, ABq, J=18 Hz).

(27) 7-[2-Methoxyimino-2-(3-nitro-4-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3400–3450, 3200, 2500–2600, 1780, 1720, 1660, 1620, 1600, 1535, 1350 cm$^{-1}$.

N.M.R. spectrum (d$_6$-DMSO, δ): ppm: 9.72 (1H, d, J=8 Hz); 7.97 (1H, d, J=2 Hz); 7.72 (1H, dd, J=2, 8 Hz); 7.21 (1H, d, J=8 Hz); 5.82 (1H, q, J=5 Hz); 5.16 (1H, d, J=5 Hz); 4.3 (2H, ABq, J=13 Hz); 3.92 (3H, s); 3.87 (3H, s); 3.72 (2H, ABq, J=18 Hz).

(28) 7-[2-Allyloxyimino-2-(3-chloro-4-hydroxyphenyl)acetamido]-3-(1-methyl-1H-tetrazol-5-yl)thiomethyl-3-cephem-4-carboxylic acid (syn isomer), mp 163° to 165° C. (dec.).

I.R. spectrum (Nujol): 3200–3300, 2500–2600, 1780, 1720, 1670, 1600 cm$^{-1}$.

N.M.R. spectrum (d$_6$-DMSO, δ): ppm: 9.70 (1H, d, J=8 Hz); 7.40 (1H, d, J=2 Hz); 7.30 (1H, dd, J=2, 8 Hz); 6.95 (1H, d, J=8 Hz); 5.80 (2H, m); 5.30 (2H, d, J=8 Hz); 5.10 (1H, d, J=5 Hz); 4.60 (2H, d, J=5 Hz); 4.27 (2H, ABq, J=13 Hz); 3.85 (3H, s); 3.65 (2H, ABq, J=18 Hz).

(29) 7-[2-Allyloxyimino-2-(3-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3250–3350, 2550–2600, 1780, 1730, 1670, 1650, 1600 cm$^{-1}$.

N.M.R. spectrum (d$_6$-DMSO, δ): ppm: 9.70 (1H, d, J=8 Hz); 7.2–6.8 (4H, m); 6.1–5.8 (2H, m); 5.35 (2H, d, J=8 Hz); 5.17 (1H, d, J=5 Hz); 4.7 (2H, d, J=5 Hz); 4.17 (2H, ABq, J=13 Hz); 3.93 (3H, s); 3.75 (2H, ABq, J=18 Hz).

(30) 7-[2-(3-Hydroxy-4-bromobenzyloxyimino)-2-(4-hydroxyphenyl)acetamido]-3-(1-methyl-1H-tetrazol-5-yl)thiomethyl-3-cephem-4-carboxylic acid (syn isomer), powder.

I.R. spectrum (Nujol): 3150, 1780, 1720, 1670 cm$^{-1}$.

N.M.R. spectrum (d$_6$-DMSO, δ): ppm: 9.60 (1H, d, J=8 Hz); 6.72–7.52 (7H, m); 5.80 (1H, dd, J=4, 8 Hz); 5.15 (1H, d, J=4 Hz); 5.00 (2H, s); 4.28 (2H, ABq, J=13 Hz); 3.90 (3H, s); 3.65 (2H, ABq, J=18 Hz).

(31) 7-[2-(2-Thienylmethoxyimino)-2-(4-hydroxyphenyl)acetamido]-3-(1-methyl-1H-tetrazol-5-yl)thiomethyl-3-cephem-4-carboxylic acid (syn isomer), powder.

I.R. spectrum (Nujol): 3200–3300, 1780, 1720, 1660 cm$^{-1}$.

N.M.R. spectrum (d$_6$-DMSO, δ): ppm: 9.77 (1H, d, J=8 Hz); 6.7–7.7 (7H, m); 5.83 (1H, dd, J=5, 8 Hz); 5.29 (2H, s); 5.15 (1H, d, J=5 Hz); 4.3 (2H, ABq, J=13 Hz); 3.92 (3H, s); 3.72 (2H, ABq, J=18 Hz).

(32) 7-[2-Ethoxyimino-2-(3-chloro-4-hydroxyphenyl)acetamido]-3-(1-methyl-1H-tetrazol-5-yl)thiomethyl-3-cephem-4-carboxylic acid (syn isomer), colorless powder, mp 153° to 156° C. (dec.).

I.R. spectrum (Nujol): 3450, 3250, 2550–2600, 1780, 1725, 1665, 1630, 1600 cm$^{-1}$.

N.M.R. spectrum (d$_6$-DMSO, δ): ppm: 9.71 (1H, d, J=8 Hz); 7.50 (1H, d, J=2 Hz); 7.36 (1H, dd, J=2, 8 Hz); 7.03 (1H, d, J=8 Hz); 5.83 (1H, q, J=5 Hz); 5.17 (1H, d, J=5 Hz); 4.33 (2H, ABq, J=13 Hz); 4.17 (2H, q, J=7 Hz); 3.97 (3H, s); 3.73 (2H, ABq, J=18 Hz); 1.25 (3H, t, J=7 Hz).

(33) 7-[2-Allyloxyimino-2-(3-methoxyphenyl)acetamido]-3-(1-methyl-1H-tetrazol-5-yl)thiomethyl-3-cephem-4-carboxylic acid (syn isomer), powder, mp 135° to 138° C. (dec).

I.R. spectrum (Nujol): 3300, 2600, 1785, 1730, 1670, 1645, 1600 cm$^{-1}$.

N.M.R. spectrum (d$_6$-DMSO, δ): ppm: 9.82 (1H, d, J=8 Hz); 7.0–7.45 (4H, m); 5.8–6.2 (2H, m); 5.36 (2H, t, J=10 Hz); 5.21 (1H, d, J=5 Hz); 4.72 (2H, d, J=5 Hz); 4.36 (2H, ABq, J=13 Hz); 3.95 (3H, s); 3.91 (3H, s); 3.87 (2H, ABq, J=18 Hz).

(34) 7-[2-Ethoxyimino-2-(3-hydroxyphenyl)acetamido]-3-(1-methyl-1H-tetrazol-5-yl)thiomethyl-3-cephem-4-carboxylic acid (syn isomer), yellow powder, mp 145° to 148° C. (dec.).

I.R. spectrum (Nujol): 3450, 3250, 2500–2600, 1775, 1720, 1665, 1620, 1600 cm$^{-1}$.

N.M.R. spectrum (d$_6$-DMSO, δ): ppm: 9.70 (1H, d, J=8 Hz); 6.8–7.4 (4H, m); 5.90 (1H, q, J=5 Hz); 5.20 (1H, d, J=5 Hz); 4.36 (2H, ABq, J=13 Hz); 4.20 (2H, q, J=7 Hz); 4.00 (3H, s); 3.76 (2H, ABq, J=18 Hz); 1.33 (3H, t, J=7 Hz).

(35) 7-[2-Ethoxyimino-2-(3-methoxyphenyl)acetamido]-3-(1-methyl-1H-tetrazol-5-yl)thiomethyl-3-cephem-4-carboxylic acid (syn isomer), pale yellow powder, mp 140° to 143° C. (dec.).

I.R. spectrum (Nujol): 3300, 2500–2600, 1785, 1730, 1670, 1630, 1600 cm$^{-1}$.

N.M.R. spectrum (d$_6$-DMSO, δ): ppm: 9.71 (1H, d, J=8 Hz); 6.9–7.5 (4H, m); 5.90 (1H, q, J=5 Hz); 5.17 (1H, d, J=5 Hz); 4.33 (2H, ABq, J=13 Hz); 4.20 (2H, q, J=7 Hz); 3.95 (3H, s); 3.85 (3H, s); 3.75 (2H, ABq, J=18 Hz); 1.30 (3H, t, J=7 Hz).

(36) 7-[2-Allyloxyimino-2-(3-chloro-4-methoxyphenyl)acetamido]-3-(1-methyl-1H-tetrazol-5-yl)thiomethyl-3-cephem-4-carboxylic acid (syn isomer), pale yellow powder, mp 153° to 156° C. (dec.).

I.R. spectrum (Nujol): 3250, 2600, 1780, 1720, 1670, 1645, 1630, 1600 cm$^{-1}$.

N.M.R. spectrum (d$_6$-DMSO, δ): ppm: 9.65 (1H, d, J=8 Hz); 7.27 (1H, d, J=2 Hz); 7.20 (1H, dd, J=2, 8 Hz); 7.09 (1H, d, J=8 Hz); 5.85–6.15 (2H, m); 5.15 (2H, t, J=9 Hz); 5.05 (1H, d, J=5 Hz); 4.60 (2H, d, J=5 Hz); 4.15 (2H, ABq, J=13 Hz); 3.95 (3H, s); 3.90 (3H, s); 3.47 (2H, ABq, J=18 Hz).

(37) 7-[2-Phenylthiomethoxyimino-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3300, 1760, 1660, 1600, 1580, 1520 cm$^{-1}$.

N.M.R. spectrum (d$_6$-DMSO, δ): ppm: 9.7 (1H, d, J=8 Hz); 7.7–6.7 (9H, m); 5.8–5.4 (3H, broad s); 5.06 (1H, d, J=5 Hz); 4.33 (2H, broad s); 3.9 (3H, s); 3.56 (2H, broad s).

(38) 7-[2-Methoxyimino-2-(3-mesylaminophenyl)acetamido]-3-(1,3,4-thiadiazol-2-yl)thiomethyl-3-cephem-4-carboxylic acid (syn isomer), mp 155° C. (dec.).

I.R. spectrum (Nujol): 3300, 1780, 1730, 1670 cm$^{-1}$.

N.M.R. spectrum (d$_6$-DMSO, δ): ppm: 9.98 (1H, s); 9.81 (1H, d, J=9 Hz); 9.62 (1H, s); 5.90 (1H, dd, J=5,9 Hz); 5.24 (1H, d, J=5 Hz); 4.49 (2H, ABq, J=14 Hz); 3.98 (3H, s); 3.77 (2H, broad s); 2.96 (3H, s).

(39) 7-[2-Methoxyimino-2-(3-carbamoyloxyphenyl)acetamido]-3-(1-methyl-1H-tetrazol-5-yl)thiomethyl-3-cephem-4-carboxylic acid (syn isomer).

I.R. spectrum (Nujol): 3450, 3300, 3200, 1780, 1725, 1670, 1620, 1590, 1520 cm$^{-1}$.

N.M.R. spectrum (d$_6$-DMSO, δ): ppm: 9.77 (1H, d, J=7 Hz); 7.6–6.8 (6H, m); 5.83 (1H, dd, J=4, 7 Hz); 5.17 (1H, d, J=4 Hz); 4.31 (2H, ABq, J=14 Hz); 3.96 (6H, s); 3.72 (2H, broad s).

(40) 7-[2-Methoxyimino-2-(3-carbamoyloxyphenyl)acetamido]-3-(1,3,4-thiadiazol-2-yl)thiomethyl-3-cephem-4-carboxylic acid (syn isomer).

I.R. spectrum (Nujol): 3250, 1780, 1735, 1675, cm$^{-1}$.

N.M.R. spectrum (d$_6$-DMSO, δ): ppm: 9.81 (1H, d, J=8 Hz); 9.62 (1H, s); 6.7–7.58 (4H, m); 5.8 (1H, dd, J=5, 8 Hz); 5.2 (1H, d, J=5 Hz); 4.25, 4.63 (2H, ABq, J=14 Hz); 3.9 (3H, s); 3.7 (2H, broad s).

(41) 7-[2-Methoxyimino-2-(3-acetoxyphenyl)acetamido]-3-(1,3,4-thiadiazol-2-yl)thiomethyl-3-cephem-4-carboxylic acid (syn isomer).

I.R. spectrum (Nujol): 3250, 1780, 1740, 1720, 1680 cm$^{-1}$.

N.M.R. spectrum (d$_6$-DMSO, δ): ppm: 9.86 (1H, d, J=8 Hz); 9.61 (1H, s); 7.00–7.65 (4H, m); 5.84 (1H, dd, J=5, 8 Hz); 5.2 (1H, d, J=5 Hz); 4.25–4.63 (2H, ABq, J=14 Hz); 3.92 (3H, s); 3.53, 3.86 (2H, ABq, J=19 Hz); 2.3 (3H, s).

(42) 7-[2-(3-Phenylallyloxyimino)-2-(3-hydroxyphenyl)acetamido]-3-(1-methyl-1H-tetrazol-5-yl)thiomethyl-3-cephem-4-carboxylic acid (syn isomer), mp 138° to 142° C. (dec.).

I.R. spectrum (Nujol): 3300–3400, 2600, 1780, 1720, 1665, 1600 cm$^{-1}$.

N.M.R. spectrum (d$_6$-DMSO, δ): ppm: 9.80 (1H, d, J=8 Hz); 6.4–7.4 (11H, m); 5.85 (1H, dd, J=5, 8 Hz); 5.20 (1H, d, J=5 Hz); 4.83 (2H, d, J=5 Hz); 4.32 (2H, ABq, J=15 Hz); 3.95 (3H, s); 3.68 (2H, ABq, J=18 Hz).

(43) 7-[2-Methoxyimino-2-(4-dimethylaminophenyl)acetamido]-3-(1-methyl-1H-tetrazol-5-yl)thiomethyl-3-cephem-4-carboxylic acid (syn isomer), mp 88° C. (dec.).

I.R. spectrum (Nujol): 3250, 1780, 1730, 1680, 1610 cm$^{-1}$.

N.M.R. spectrum (d$_6$-DMSO, δ): ppm: 9.63 (1H, d, J=8 Hz); 7.40 (2H, d, J=8 Hz); 6.73 (2H, d, J=8 Hz); 5.83 (1H, dd, J=5, 8 Hz); 5.17 (1H, d, J=5 Hz); 4.33 (2H, ABq, J=13 Hz); 3.97 (3H, s); 3.87 (3H, s); 3.73 (2H, broad s); 3.00 (6H, s).

(44) 7-[2-Methoxyimino-2-(3-hydroxyphenyl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d$_6$-DMSO, δ): ppm: 9.67 (1H, d, J=9 Hz); 6.72-7.36 (4H, m); 5.78 (1H, dd, J=5, 9 Hz); 5.12 (1H, d, J=5 Hz); 4.55 (2H, broad s); 4.30 (2H, broad s); 3.90 (3H, s); 3.40-3.80 (2H, m); 3.14 (2H, broad s); 2.48 (6H, s).

(45) 7-[2-{2-(2-Hydroxyphenoxy)ethoxyimino}-2-(3-hydroxyphenyl)-acetamido]-3-(1-methyl-1H-tetrazol-5-yl)thiomethyl-3-cephem-4-carboxylic acid (syn isomer).

I.R. spectrum (Nujol): 3270, 1780, 1725, 1670, 1560 cm$^{-1}$.

N.M.R. spectrum (d$_6$-DMSO, δ): ppm: 6.5-7.4 (8H, m); 5.86(1H, dd, J=5, 8 Hz); 5.14(1H, d, J=5 Hz); 4.0-4.6 (6H, m); 3.92(3H, s); 3.52, 3.70(2H, AB$_q$, J=7 Hz).

EXAMPLE 27

A solution of 7-[2-methoxyimino-2-(2-amino-1,3-thiazol-4-yl)acetamido]-3-hydroxymethyl-3-cephem-4-carboxylic acid (syn isomer) (0.3 g) in a mixture of acetone (3 ml) and water (1.5 ml) was adjusted to pH 2 with 6 N hydrochloric acid and stirred for 4 hours at ambient temperature. After the acetone was distilled off, to the residue was added water (1 ml). The mixture was adjusted to pH 7 with a saturated aqueous solution of sodium bicarbonate and ice-cooled for 1 hour. Precipitating crystals were collected by filtration, washed with water and dried to give 6-[2-methoxyimino-2-(2-amino-1,3-thiazol-4-yl)acetamido]-5a,6-dihydro-3H,7H-azeto[2,1-b]furo[3,4-d][1,3]thiazine-1,7(4H)-dione (syn isomer) (0.23 g), mp 210° to 215° C. (dec.).

I.R. spectrum (Nujol): 3270, 1780, 1740, 1655, 1610, 1525 cm$^{-1}$.

N.M.R. spectrum (d$_6$-DMSO, δ): ppm: 9.70 (1H, d, J=8 Hz); 7.26 (2H, broad s); 6.77 (1H, s); 5.93 (1H, dd, J=5, 8 Hz); 5.16 (1H, d, J=5 Hz); 5.05 (2H, broad s); 3.85 (3H, s); 3.81 (2H, broad s).

EXAMPLE 28

The following compound was obtained according to a similar manner to that of Example 27.

6-[2-methoxyimino-2-(3-hydroxyphenyl)acetamido]-5a,6-dihydro-3H,7H-azeto[2,1-b]furo[3,4-d][1,3]thiazine-1,7(4H)-dione(syn isomer).

I.R. spectrum (Nujol): 3250, 1785, 1755, 1660, 1600, 1570, 1540 cm$^{-1}$.

N.M.R. spectrum (d$_6$-DMSO, δ): ppm: 9.83 (1H, d, J=8 Hz); 7.5-6.75 (4H, m); 6.02 (1H, dd, J=5, 8 Hz); 5.21 (1H, d, J=5 Hz); 5.07 (2H, broad s); 3.95 (3H, s); 3.84 (2H, broad s).

EXAMPLE 29

7-[2-Methoxyimino-2-{2-(2,2,2-trifluoroacetamido)-1,3-thiazol-4-yl}acetamido]-3-hydroxymethyl-3-cephem-4-carboxylic acid (syn isomer) (1.0 g.) was dissolved in a mixture of dimethylformamide (6 ml.) and acetone (30 ml.). Jones reagent (1.25 ml.), which was prepared from conc. sulfuric acid (0.28 ml.), chromium trioxide (0.33 g.) and water (0.9 ml.), was dropwise added thereto over 2 minutes with stirring and cooling at 0° to 2° C. After stirring for 20 minutes at the same temperature, the reaction mixture was poured into ice-water (50 ml). After acetone was distilled off, the residue was twice extracted with ethyl acetate (50 ml.). The extracts were washed with a saturated aqueous solution of sodium chloride and dried over magnesium sulfate. The solvent was distilled off and the residue was pulverized with diisopropyl ether to give 7-[2-methoxyimino-2-{2-(2,2,2-trifluoroacetamido)-1,3-thiazol-4-yl}-acetamido]-3-formyl-3-cephem-4-carboxylic acid (syn isomer) [or this compound can be represented as 3-hydroxy-6-[2-methoxyimino-2-{2-(2,2,2-trifluoroacetamido)-1,3-thiazol-4-yl}acetamido]-5$_a$,6-dihydro-3H, 7H-azeto[2,1-b]furo[3,4-d][1,3]thiazine-1,7(4H)dione (syn isomer)] (0.56 g.).

I.R. spectrum (Nujol): 3150, 1790, 1720, 1655, 1560, 1500 cm$^{-1}$.

N.M.R. spectrum (d$_6$-DMSO, δ): ppm: 9.88 (1H, d, J=8 Hz); 7.60 (1H, s); 6.30 (1H, d, J=6 Hz); 6.05 (1H, dd, J=5,8 Hz); 5.23 (1H, d, J=5 Hz); 3.96 (3H, s); 3.80 (2H, broad s).

EXAMPLE 30

The following compounds were obtained by conducting elimination reaction of protective group of amino on carbamoyl group according to a similar manner to that of Example 3.

(1) 7-[2-Methoxyimino-2-(2-amino-1,3-thiazol-4-yl)acetamido]-3-carbamoyloxymethyl-3-cephem-4-carboxylic acid (syn isomer), mp 210° to 220° C. (dec.).

I.R. spectrum (Nujol): 3250, 1765, 1650 cm$^{-1}$.

N.M.R. spectrum (d$_6$-DMSO, δ): ppm: 9.64 (1H, d, J=8 Hz); 7.4 (2H, m); 6.79 (1H, s); 6.60 (2H, m); 5.77 (1H, dd, J=5,8 Hz); 5.16 (1H, d, J=5 Hz); 4.75 (2H, AB$_q$, J=12 Hz); 3.87 (3H, s); 3.53 (2H, AB$_q$, J=18 Hz).

(2) 7-2-Methoxyimino-2-(2-formamido-1,3-thiazol-4-yl)acetamido]-3-carbamoyloxymethyl-3-cephem-4-carboxylic acid (syn isomer).

I.R. spectrum (Nujol): 3300, 1780, 1705, 1680 cm$^{-1}$.

N.M.R. spectrum (d$_6$-DMSO, δ): ppm: 12.50 (1H, broad s); 9.67 (1H, d, J=8 Hz); 8.50 (1H, s); 7.43 (1H, s); 6.58 (2H, broad s); 5.80 (1H, dd, J=5,8 Hz); 5.16 (1H, d, J=5 Hz); 4.78 (2H, AB$_q$, J=14 Hz); 3.95 (3H, s); 3.57 (2H, AB$_q$, J=18 Hz).

REFERENCE 1

Phosphorus pentachloride (3.3 g.) was added under ice-cooling to a suspension of 2-methoxyimino-2-(2-amino-1,3-thiazol-4-yl)acetic acid (syn isomer) (1.5 g.) in methylene chloride (30 ml.) and the mixture was stirred for 30 minutes at ambient temperature. Methylene chloride was distilled off under reduced pressure and acetone was added to the residue to give a suspension. On the other hand, a suspension of 7-amino-3-(1-methyl-1H-tetrazol-5-yl)thiomethyl-3-cephem-4-carboxylic acid (2.2 g.) in an aqueous solution of sodium bicarbonate (0.76 g. in 50 ml. of water) was stirred for 10 minutes and acetone (50 ml.) was added thereto to give a solution. To the solution was dropwise added the above obtained suspension containing acid chloride with stirring and ice-cooling and keeping the solution at pH 7.5 to 8.5 with a 20% aqueous solution of sodium carbonate. The mixture was stirred for 1 hour at 3° to 5° C. and pH 8.0. Acetone was distilled off under reduced pressure and the residue was adjusted to pH 7.4 with a saturated aqueous solution of sodium bicarbonate and further adjusted to pH 4.5 with 10% hydrochloric acid with stirring and ice-cooling. Precipitates were filtered off and the filtrate was saturated with sodium chloride, adjusted to pH 2.5 with 10% hydrochloric acid and stirred for 1 hour. Precipitates were collected by filtration, washed with water and dried to give 7-[2-methoxyimino-2-(2-amino-1,3-thiazol-4-yl)acetamido]-3-(1-methyl-1H-tetrazol-5-yl)thiomethyl-3-cephem-4-carboxylic acid (a mixture of syn and anti isomers) (0.95 g.).

I.R. spectrum (Nujol): 3400, 1775, 1710, 1670, 1630 cm$^{-1}$.

N.M.R. spectrum (d$_6$-DMSO, δ): ppm: 9.85 (1H, d, J=8 Hz); 9.50 (1H, d, J=8 Hz); 7.58 (1H, s); 6.87 (1H, s); 6.65 (4H, broad s); 5.77 (2H, m); 5.15 (2H, d, J=5 Hz); 4.35 (4H, broad s); 4.06 (6H, s); 3.97 (6H, s); 3.75 (4H, broad s).

REFERENCE 2

A suspension of phosphorus pentachloride (1.7 g.) in methylene chloride (20 ml.) was changed to a solution by stirring for 2 hours at ambient temperature. 2-Methoxyimino-2-(2-amino-1,3-thiazol-4-yl)acetic acid (syn isomer) (0.8 g.) was added thereto at a time at ambient temperature and the mixture was stirred. Methylene chloride was distilled off under reduced pressure and the residue was dissolved in acetone (20 ml.). On the other hand, 7-amino-3-carbamoyloxymethyl-3-cephem-4-carboxylic acid (1.0 g.) was suspended in a solution of sodium bicarbonate (0.59 g.) in water (20 ml.) and dissolved by adding acetone (10 ml.). To this solution was dropwise added the above obtained solution containing acid chloride with stirring and ice-cooling and keeping the solution at pH 7.5 to 8.5 with a 20% aqueous solution of sodium carbonate. After stirring for 1 hour at pH 8 under ice-cooling, an insoluble material was filtered off. Acetone was distilled off under reduced pressure from the filtrate and an insoluble material was filtered off. The filtrate was adjusted to pH 2.5 with 10% hydrochloric acid. Precipitates were collected by filtration and dried to give 7-[2-methoxyimino-2-(2-amino-1,3-thiazol-4-yl)acetamido]-3-carbamoyloxymethyl-3-cephem-4-carboxylic acid (a mixture of syn and anti isomers) (0.4 g.). The filtrate was saturated with sodium chloride and stirred under ice-cooling to give precipitates. The precipitates were collected by filtration and dried to give the same object compound (0.3 g.). Total yield (0.7 g.).

I.R. spectrum (Nujol): 3400, 1775, 1705 cm$^{-1}$.

N.M.R. spectrum (d$_6$-DMSO, δ): ppm: 9.71 (1H, d, J=8 Hz); 9.42 (1H, d, J=8 Hz); 7.70 (1H, s); 7.40 (4H, broad s); 7.00 (1H, s); 6.61 (4H, s); 5.76(2H, m); 5.16 (2H, d, J=4.5 Hz); 4.76 (4H, AB$_q$, J=12 Hz); 3.98 (3H, s); 3.89 (3H, s); 3.53 (4H, AB$_q$, J=18 Hz).

REFERENCE 3

A mixture of dimethylformamide (0.22 g.) and phosphorus oxychloride (0.46 g.) was warmed for 1 hour at 40° C. The mixture was dissolved in dry methylene chloride (20 ml.) and 2-methoxyimino-2-(2-mesylimino-3-methyl-2,3-dihydro-1,3-thiazol-4-yl)acetic acid (anti isomer) (0.73 g.) was added thereto with stirring and ice-cooling, after which the resulting mixture was stirred for 1.5 hours under ice-cooling. On the other hand, 7-amino-3-(1-methyl-1H-tetrazol-5-yl)thiomethyl-3-cephem-4-carboxylic acid (0.82 g.) was dissolved in a solution of bis(trimethylsilyl)acetamide (1.5 g.) in dry methylene chloride (20 ml.). To this solution was added at −30° C. the above obtained methylene chloride solution, after which the mixture was stirred for 2 hours at −5° to −20° C. After distilling off methylene chloride at low temperature, water was added to the residue and the mixture was extracted with ethyl acetate. The extract was washed with a sodium chloride aqueous solution and water (50 ml.) was added thereto. The resulting mixture was adjusted to pH 7 with an aqueous solution of sodium bicarbonate and the aqueous layer was separated. The aqueous layer was adjusted to pH 1.5, saturated with sodium chloride and extracted with ethyl acetate. The extract was washed with a sodium chloride aqueous solution and dried over magnesium sulfate. The solvent was distilled off and the residue was pulverized by a mixture of diisopropyl ether and ether. The powder was collected by filtration and dried to give 7-[2-methoxyimino-2-(2-mesylimino-3-methyl-2,3-dihydro-1,3-thiazol-4-yl)acetamido]-3-(1-methyl-1H-tetrazol-5-yl)thiomethyl-3-cephem-4-carboxylic acid (anti isomer) (1.0 g.). This powder (1.0 g.) was suspended in water (30 ml.) and dissolved by adjusting to pH 6 by an aqueous solution of sodium bicarbonate. After removing the solvent by bubbling of nitrogen gas, the aqueous solution was lyophilized to give sodium 7-[2-methoxyimino-2-(2-mesylimino-3-methyl-2,3-dihydro-1,3-thiazol-4-yl)acetamido]-3-(1-methyl-1H-tetrazol-5-yl)thiomethyl-3-cephem-4-carboxylate (anti isomer) (0.98 g.).

I.R. spectrum (KBr): 1760, 1675 cm$^{-1}$.

N.M.R. spectrum (D$_2$O, δ): ppm: 8.05 (1H, s); 5.76 (1H, d, J=5 Hz); 5.16 (1H, d, J=5 Hz); 4.14 (2H, AB$_q$, J=13 Hz); 4.10 (3H, s); 4.02 (3H, s); 3.52 (2H, AB$_q$, J=17 Hz); 3.45 (3H, s); 3.24 (3H, s).

REFERENCE 4

The following compounds were obtained according to a similar manner to that of Reference 3.

(1) 7-[2-Methoxyimino-2-(2-methyl-1,3-thiazol-4-yl)acetamido]-3-(1-methyl-1H-tetrazol-5-yl)thiomethyl-3-cephem-4-carboxylic acid (anti-isomer).

I.R. spectrum (Nujol): 1790, 1720, 1680 cm$^{-1}$.

N.M.R. spectrum (d$_6$-DMSO, δ): ppm: 9.53 (1H, d, J=8 Hz); 8.27 (1H, s); 5.83 (1H, dd, J=5.5, 8 Hz); 5.15 (1H, d, J=5.5 Hz); 4.30 (2H, AB$_q$, J=14 Hz); 4.00 (3H, s); 3.93 (3H, s); 3.70 (2H, AB$_q$, J=16 Hz); 2.65 (3H, s).

(2) 7-[2-Methoxyimino-2-(2-amino-1,3-thiazol-4-yl)acetamido]-3-(1-methyl-1H-tetrazol-5-yl)thiomethyl-3-cephem-4-carboxylic acid (anti isomer).

I.R. spectrum (Nujol): 3400, 1775, 1670 cm$^{-1}$.

N.M.R. spectrum (d$_6$-DMSO, δ): ppm: 9.44 (1H, d, J=8 Hz); 7.71 (1H, s); 6.40 (2H, broad s); 5.77 (1H, dd, J=8 Hz); 5.13 (1H, d, J=5 Hz); 4.31 (2H, broad s); 4.00 (3H, s); 3.95 (3H, s); 3.70 (2H, broad s).

(3) 7-[2-Methoxyimino-2-(2-amino-1,3-thiazol-4-yl)acetamido]cephalosporanic acid (anti isomer).

I.R. spectrum (Nujol): 3400–3100, 1780, 1730, 1675 cm$^{-1}$.

N.M.R. spectrum (d$_6$-DMSO, δ): ppm: 9.43 (1H, d, J=8 Hz); 9.16 (2H, broad s); 7.73 (1H, s); 5.82 (1H, dd, J=5,8 Hz); 5.18 (1H, d, J=5 Hz); 4.90 (2H, AB$_q$, J=13 Hz); 4.03 (3H, s); 3.60 (2H, broad s); 2.07 (3H, s).

(4) 7-[2-Methoxyimino-2-(2-formamido-1,3-thiazol-4-yl)acetamido]-3-(1,3,4-thiadiazol-2-yl)thiomethyl-3-cephem-4-carboxylic acid (anti isomer), mp 152° C. (dec.).

I.R. spectrum (Nujol): 3300–3100, 1775, 1720, 1670, 1630 cm$^{-1}$.

N.M.R. spectrum (d$_6$-DMSO, δ): ppm: 12.63 (1H, broad s); 9.66 (1H, s); 9.57 (1H, d, J=8 Hz); 8.50 (1H, s); 8.07 (1H, s); 5.75 (1H, dd, J=5,8 Hz); 5.15 (1H, d, J=5 Hz); 4.27 (2H, ABq, J=13 Hz); 4.00 (3H, s); 3.70 (2H, broad s).

(5) 7-[2-Methoxyimino-2-(3-hydroxyphenyl)acetamido]-3-(1-methyl-1H-tetrazol-5-yl)thiomethyl-3-cephem-4-carboxylic acid (anti isomer).

I.R. spectrum (Nujol): 3350, 1780, 1726, 1680 cm$^{-1}$.

N.M.R. spectrum (d$_6$-DMSO, δ)

| ppm | |
|---|---|
| 9.24 | (1H, d, J = 8Hz) |
| 7.36–7.10 | ⎫ |
|  | ⎬ (4H, m) |
| 7.00–6.74 | ⎭ |
| 5.70 | (1H, dd, J = 5,8Hz) |
| 5.13 | (1H, d, J = 5Hz) |
| 4.34 | (2H, AB$_q$, J = 13Hz) |
| 3.95 | (6H, s) |
| 3.72 | (2H, AB$_q$, J = 17Hz) |

PREPARATION OF THE STARTING COMPOUNDS TO BE USED FOR THE EXAMPLES AND REFERENCES

Preparation 1

A mixture of 3-chloro-4-hydroxyacetophenone (11.9 g.), benzyl chloride (9.35 g.), potassium carbonate (14.5 g.) and dimethylformamide (60 ml.) was stirred for 1 hour at 100° C. The reaction mixture was poured into water (150 ml.) and extracted with ethyl acetate. The extract was washed with a sodium chloride aqueous solution and dried over magnesium sulfate. After distilling off the solvent, the residue (18 g.) was recrystallized from ethanol (160 ml.) to give 3-chloro-4-benzyloxyacetophenone (13.2 g.), mp 110° to 112° C.

Preparation 2

(1) Selenium dioxide powder (12.6 g.) was added over 10 minutes to a solution of 3-chloro-4-benzyloxyacetophenone (19.7 g.) in dry pyridine (100 ml.) with stirring at 100° C., and the mixture was stirred for 3 hours at the same temperature. Precipitating selenium was filtered off and the filtrate was concentrated. The residue was dissolved in water (150 ml.) and the solution was washed with ether. The aqueous solution was acidified under cooling with conc. hydrochloric acid and extracted with ether. The extract was washed with a sodium chloride aqueous solution, dried over magnesium sulfate and concentrated to give 2-(3-chloro-4-benzyloxyphenyl)glyoxylic acid (15.9 g.), mp 134° to 135° C.

(2) The following compounds were obtained according to a similar manner to that of Preparation (2-1).

(1) 2-(3-Nitro-4-benzyloxyphenyl)glyoxylic acid, mp 161° to 164° C.

(2) 2-(3-Chloro-4-methoxyphenyl)glyoxylic acid, mp 81° to 82° C.

I.R. spectrum (Nujol): 2500–2600, 1715, 1670, 1600 cm$^{-1}$.

(3) 2-(3-Mesylaminophenyl)glyoxylic acid, mp 66° to 68° C.

I.R. spectrum (Nujol): 3560, 3250, 1720, 1670 cm$^{-1}$.

Preparation 3

(1) A mixture of 2-(3-nitro-4-benzyloxyphenyl)glyoxylic acid (30 g.), conc. hydrochloric acid (90 ml.) and acetic acid (120 ml.) was stirred for 3 hours at 100° C. To the reaction mixture was added under cooling ice-water (600 ml.) and the mixture was extracted with ethyl acetate. The extract was washed with ice-water, dried over magnesium sulfate and concentrated to dryness under reduced pressure. The residue was recrystallized from a mixture of benzene: ether: petroleum ether (2:1:4). The crystals were collected by filtration, washed with benzene and dried under reduced pressure to give 2-(3-nitro-4-hydroxyphenyl)glyoxylic acid (19.0 g.), mp 139° to 140.5° C.

(2) The following compound was obtained according to a similar manner to that of Preparation (3-1).

(1) 2-(3-Chloro-4-hydroxyphenyl)glyoxylic acid, mp 114° to 116° C.

Preparation 4

2-(3-Hydroxyphenyl)glyoxylic acid (3.32 g.) and 1 N-methanol solution of hydroxylamine (45 ml.) were refluxed with stirring for 25 minutes. The reaction mixture was concentrated under reduced pressure. The residue was dissolved in 1 N-aqueous solution of sodium hydroxide (70 ml.). An aqueous solution was washed with ether, acidified with dil. hydrochloric acid and then extracted with ethyl acetate. The extract was washed, dried and treated with an activated charcoal. The solvent was distilled off to give 2-hydroxyimino-2-(3-hydroxyphenyl)acetic acid (a mixture of syn and anti isomers) (2.9 g.).

I.R. spectrum (Nujol): 3200, 1700 cm$^{-1}$.

Preparation 5

(1) (a) Phenolphthalein indicator (3 drops) was added to a solution of O-methylhydroxylamine hydrochloride (5.5 g.) in dry methanol (60 ml.). To the solution was dropwise added with stirring at ambient temperature 1 N methanol solution of sodium methoxide (65 ml.) until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, 2-(3-hydroxyphenyl)glyoxylic acid (9.85 g.) was added to the filtrate and the mixture was refluxed for 30 minutes. After methanol was distilled off at low temperature, a saturated sodium chloride aqueous solution was added to the residue. The mixture was adjusted to pH 1 with 10% hydrochloric acid and extracted with ether (300 ml.). The extract was dried over magnesium sulfate. Ether was distilled off at low temperature to give 2-methoxyimino-2-(3-hydroxyphenyl)acetic acid (a mixture of syn and anti isomers).

(b) This material was dissolved in ether (60 ml.) and a solution of diazomethane in ether was gradually added thereto under ice-cooling until the color of the mixture was changed to yellow. Acetic acid was immediately added thereto and the mixture was washed with a sodium bicarbonate aqueous solution and a saturated sodium chloride aqueous solution and dried over magnesium sulfate. Ether was distilled off to give oily residue (10.8 g.). The oily residue was subjected to column chromatography on silica gel (165 g.) using a mixture of benzene and ethyl acetate (9:1) as developing solvent. Firstly the eluate containing syn isomer was eluted and the eluate was collected and concentrated to give oily methyl 2-methoxyimino-2-(3-hydroxyphenyl)acetate (syn isomer) (7.9 g.). The oil was allowed to stand to give crystals, mp 39.5° to 40.5° C.

I.R. spectrum (Nujol): 3450, 1730 cm$^{-1}$.

N.M.R. spectrum (CDCl$_3$, δ): ppm: 6.7–7.42 (4H, m); 3.98 (3H, s); 3.92 (3H, s).

After the eluate containing syn isomer was eluted, then the eluate containing anti isomer was eluted. The eluate was collected and concentrated to give methyl 2-methoxyimino-2-(3-hydroxyphenyl)acetate (anti isomer) (1.5 g.). This material was recrystallized from a mixture of benzene and petroleum ether to give crystals, mp 96° to 98° C.

I.R. spectrum (Nujol): 3350, 1715 cm$^{-1}$.

N.M.R. spectrum (CDCl$_3$, δ): ppm: 7.12–7.40 (1H, m); 6.96–7.02 (3H, m); 3.99 (3H, s); 3.84 (3H, s).

(c) A 2 N aqueous solution of sodium hydroxide (40 ml.) was added with stirring at ambient temperature to a suspension of methyl 2-methoxyimino-2-(3-hydroxyphenyl)acetate (syn isomer) (7.55 g.) in water (70 ml.) and the mixture was stirred for 1 hour at ambient temperature. The reaction mixture was adjusted to pH 6.5 with 10% hydrochloric acid, subjected to salting-out and washed with ether (60 ml.). The aqueous layer was adjusted to pH 1 with conc. hydrochloric acid and extracted once with 100 ml. of and twice with 60 ml. of ether. The extract was washed twice with a saturated sodium chloride aqueous solution (60 ml.) and dried over magnesium sulfate. Ether was distilled off to give oil. Benzene was added thereto and removed (twice) to give crystals of 2-methoxyimino-2-(3-hydroxyphenyl)acetic acid (syn isomer) (6.44 g.), mp 98° to 101° C. (dec.).

I.R. spectrum (Nujol): 3370, 1720 cm$^{-1}$.

An aqueous solution of 2 N sodium hydroxide (8 ml.) was added with stirring at ambient temperature to a solution of methyl 2-methoxyimino-2-(3-hydroxyphenyl)acetate (anti isomer) (1.56 g.) in methanol (30 ml.). After stirring for 3 hours at the same temperature, methanol was distilled off. To the residue was added water and the mixture was washed with ether. The aqueous layer was adjusted to pH 1 with 10% hydrochloric acid, subjected to salting-out and extracted with ether. The extract was washed with a sodium chloride aqueous solution and dried over magnesium sulfate. Ether was distilled off to give crystals of 2-methoxyimino-2-(3-hydroxyphenyl)acetic acid (anti isomer) (1.07 g.). The crystals were recrystallized from a mixture of petroleum ether and ether to give crystals (0.7 g.), mp 99° to 101° C. (dec.).

I.R. spectrum (Nujol): 3350, 1690 cm$^{-1}$.

(2) (a) Phenolphthalein indicator (3 drops) was added to a solution of O-methylhydroxylamine hydrochloride (3.7 g.) in dry methanol (45 ml.). To the solution was dropwise added with stirring at ambient temperature 1 N methanol solution of sodium methoxide (39 ml.) until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, 2-(4-hydroxyphenyl)-glyoxylic acid (6.56 g.) was added to the filtrate and the mixture was stirred for 1 hour at ambient temperature. After methanol was distilled off at low temperature, a saturated sodium chloride aqueous solution was added to the residue. The mixture was adjusted to pH 1 with 10% hydrochloric acid, subjected to salting-out and extracted with ether. The extract was dried over magnesium sulfate. Ether was distilled off at low temperature to give 2-methoxyimino-2-(4-hydroxyphenyl)acetic acid (syn isomer).

(b) This material was dissolved in ether (50 ml.) and a solution of diazomethane in ether was gradually added thereto under ice-cooling until the color of the mixture was changed to yellow. Acetic acid was immediately added thereto and the mixture was washed with a sodium bicarbonate aqueous solution and a saturated sodium chloride aqueous solution and dried over magnesium sulfate. Ether was distilled off to give oily residue (8 g.). The oily residue was subjected to column chromatography on silica gel using a mixture of benzene and ethyl acetate (9:1) as developing solvent to give methyl 2-methoxyimino-2-(4-hydroxyphenyl)acetate (syn isomer) (6.39 g.).

I.R. spectrum (Nujol): 3350, 1720 cm$^{-1}$.

N.M.R. spectrum (CDCl$_3$, δ): ppm: 7.40 (2H, d, J=8 Hz); 6.80 (2H, d, J=8 Hz); 3.96 (3H, s); 3.92 (3H, s).

(c) A 2 N aqueous solution of sodium hydroxide (11 ml.) was added with stirring at ambient temperature to a solution of methyl 2-methoxyimino-2-(4-hydroxyphenyl)acetate (syn isomer) (2.1 g.) in methanol (30 ml.) and the mixture was stirred for 18 hours at ambient temperature. The reaction mixture was adjusted to pH 7 with 10% hydrochloric acid and methanol was removed. To the residue was added water and the mixture was washed with ether. The aqueous layer was adjusted to pH 1 with 10% hydrochloric acid, subjected to salting-out and extracted with ethyl acetate. The extract was washed with a saturated sodium chloride aqueous solution and dried over magnesium sulfate. Ethyl acetate was distilled off to give crystals of 2-methoxyimino-2-(4-hydroxyphenyl)acetic acid (syn isomer) (1.5 g.).

I.R. spectrum (Nujol): 3150, 1700 cm$^{-1}$.

(3) (a) Phenolphthalein indicator (2 drops) was added to a solution of O-methylhydroxylamine hydrochloride (2.74 g.) in dry methanol (30 ml.). To the solution was dropwise added with stirring at ambient temperature 1 N methanol solution of sodium methoxide until the color of the solution was changed to purplish red. O-Methylhydroxylamine hydrochloride was added thereto by small portions until the solution was changed to colorless solution. The mixture was stirred for 1 hour at ambient temperature. After precipitating sodium chloride was filtered off, 2-(3-nitro-4-hydroxyphenyl)-glyoxylic acid (6.75 g.) was added to the filtrate and the mixture was stirred for 1 hour at ambient temperature. After methanol was distilled off at 35° C., a saturated sodium chloride aqueous solution was added to the residue. The mixture was adjusted to pH 1 with 10% hydrochloric acid and extracted with ether. The extract was dried over magnesium sulfate. Ether was distilled off at 35° C. under reduced pressure to give yellow crystals of 2-methoxyimino-2-(3-nitro-4-hydroxyphenyl)acetic acid (a mixture of syn and anti isomers) (7 g.)

(b) This material was dissolved in a mixture of tetrahydrofuran (15 ml.) and ether (100 ml.) and a solution of diazomethane in ether was gradually added thereto at ambient temperature until the color of the mixture was changed to yellow. Acetic acid was immediately added thereto and the mixture was concentrated to dryness at 35° C. under reduced pressure. The residue was dissolved in a mixed solvent of ethyl acetate and benzene (1:9) and subjected to column chromatography on silica gel using the same mixed solvent as developing solvent. The eluate containing syn isomer was collected and concentrated to give methyl 2-methoxyimino-2-(3-nitro-4-hydroxyphenyl)acetate (syn isomer) (3.7 g.), mp 93° to 95° C.

I.R. spectrum (Nujol): 3300, 1745, 1630, 1535, 1350 cm$^{-1}$.

N.M.R. spectrum (CDCl$_3$, δ): ppm: 10.87 (1H, s); 8.22 (1H, d, J=2 Hz); 7.86 (1H, dd, J=2, 8 Hz); 7.20 (1H, d, J=8 Hz); 4.03 (3H, s); 3.95 (3H, s).

(c) A 2 N aqueous solution of sodium hydroxide (14 ml.) was added with stirring at ambient temperature to a solution of methyl 2-methoxyimino-2-(3-nitro-4-hydroxyphenyl)acetate (syn isomer) (3.5 g.) in methanol (70 ml.) and the mixture was stirred for 60 hours at ambient temperature. The reaction mixture was concentrated to dryness at 40° C. under reduced pressure and the residue was dissolved in water. The solution was washed with ethyl acetate, adjusted to pH 1 with 10% hydrochloric acid under ice-cooling and extracted with ethyl acetate. The extract was back-extracted with a saturated sodium bicarbonate aqueous solution. The aqueous extract was adjusted to pH 1 with conc. hydrochloric acid under ice-cooling and extracted with ethyl acetate. The extract was washed with ice-water and dried over magnesium sulfate. The solvent was concentrated to dryness at 40° C. under reduced pressure to give yellow crystals of 2-methoxyimino-2-(3-nitro-4-hydroxyphenyl)acetic acid (syn isomer) (3.2 g.), mp 142° to 143° C. (dec.).

I.R. spectrum (Nujol): 3300, 2500–2600, 1710, 1630, 1600, 1535, 1375 cm$^{-1}$.

N.M.R. spectrum (CDCl$_3$, δ): ppm: 10.67 (2H, s); 8.33 (1H, d, J=2 Hz); 7.95 (1H, dd, J=2,8 Hz); 7.22 (1H, d, J=8 Hz); 4.13 (3H, s).

(4)(a) 2-(3-Chloro-4-hydroxyphenyl)glyoxylic acid (6.45 g.) and O-methylhydroxylamine hydrochloride (2.74 g.) were reacted according to a similar manner to that of Preparation (5-3)(a) to give oil of 2-methoxyimino-2-(3-chloro-4-hydroxyphenyl)acetic acid (a mixture of syn and anti isomers) (7 g.).

(b) 2-Methoxyimino-2-(3-chloro-4-hydroxyphenyl)acetic acid (a mixture of syn and anti isomers) (7 g.) and diazomethane (1.5 g.) were reacted and the product was purified by column chromatography according to a similar manner to that of Preparation (5-3)(b) to give crystals of methyl 2-methoxyimino-2-(3-chloro-4-hydroxyphenyl)acetate (syn isomer) (3.0 g.).

I.R. spectrum (Film) 3450, 1735, 1605, 1600 cm$^{-1}$.

N.M.R. spectrum (CDCl$_3$, δ): ppm: 7.55 (1H, d, J=2 Hz); 7.37 (1H, dd, J=2,8 Hz); 6.95 (1H, d, J=8 Hz); 6.12 (1H, s); 3.97 (3H, s); 3.91 (3H, s).

(c) Methyl 2-methoxyimino-2-(3-chloro-4-hydroxyphenyl)acetate (syn isomer) (2.6 g.) and a 2 N aqueous solution of sodium hydroxide (10.6 ml.) were treated according to a similar manner to that of Preparation 5-3)(c) to give 2-methoxyimino-2-(3-chloro-4-hydroxyphenyl)acetic acid (syn isomer) (2.4 g.), mp 147° to 150° C. (dec.).

I.R. spectrum (Nujol): 3500, 2500–2600, 1745, 1610, 1600 cm$^{-1}$.

N.M.R. spectrum (CDCl$_3$, δ): ppm: 8.40 (2H, broad s); 7.65 (1H, d, J=2 Hz); 7.40 (1H, dd, J=2,8 Hz); 7.00 (1H, d, J=8 Hz); 4.07 (3H, s).

(5) 2-(3-Hydroxyphenyl)glyoxylic acid (2.0 g.) and O-allylhydroxylamine hydrochloride (1.7 g.) were reacted according to a similar manner to that of Preparation (5-2)(a) to give oil of 2-allyloxyimino-2-(3-hydroxyphenyl)acetic acid (syn isomer) (2.7 g.).

I.R. spectrum (Film): 3350, 2550–2600, 1720, 1645, 1600 cm$^{-1}$.

(6) 2-(3-Chloro-4-hydroxyphenyl)glyoxylic acid (2 g.) and O-allylhydroxylamine hydrochloride (1.1 g.) were reacted according to a similar manner to that of Preparation (5-2)(a) to give oil of 2-allyloxyimino-2-(3-chloro-4-hydroxyphenyl)acetic acid (syn isomer) (2.5 g.).

I.R. spectrum (Film): 3450, 2600, 1730, 1700, 1650, 1610, 1600 cm$^{-1}$.

N.M.R. spectrum (d$_6$-DMSO, δ): ppm: 9.5–10.5 (2H, broad s); 7.52 (1H, d, J=2 Hz); 7.42 (1H, dd, J=2,8 Hz); 7.12 (1H, d, J=8 Hz); 6.0 (1H, m); 5.40 (2H, t, J=8 Hz); 4.70 (2H, d, J=5 Hz).

(7) A mixture of 2-(3-chloro-4-hydroxyphenyl)glyoxylic acid (2.0 g.), O-t-butoxycarbonylmethylhydroxylamine (1.62 g.) and methanol (20 ml.) was adjusted to pH 5 to 6 by adding an 1 N methanol solution of sodium methoxide and stirred for 3 hours at ambient temperature. The reaction mixture was concentrated to dryness under reduced pressure and the residue was dissolved in an 1 N aqueous solution of sodium hydroxide to adjust to pH 7.0. The aqueous solution was washed with ether, adjusted to pH 2.0 with 10% hydrochloric acid under ice-cooling and extracted with ether. The extract was washed with water and dried over magnesium sulfate. The solution was concentrated to dryness under reduced pressure to give crystals of 2-t-butoxycarbonylmethoxyimino-2-(3-chloro-4-hydroxyphenyl)acetic acid (syn isomer) (2.6 g.), mp 116° to 118° C. (dec.).

I.R. spectrum (Nujol): 3250, 2600, 1735, 1690, 1670, 1610, 1590 cm$^{-1}$.

N.M.R. spectrum (d$_6$-DMSO, δ): ppm: 11.00 (2H, broad s); 7.50 (1H, d, J=2 Hz); 7.40 (1H, dd, J=2,8 Hz); 7.08 (1H, d, J=8 Hz); 4.68 (2H, s); 1.45 (9H, s).

(8)(a) Potassium carbonate (49.7 g.) and dimethyl sulfate (45.4 g.) were added to a solution of 2-hydroxyimino-2-(3-hydroxyphenyl)acetic acid (a mixture of syn and anti isomers) (18.1 g.) in dry acetone (250 ml.) and the mixture was refluxed with stirring for 8.5 hours. After acetone was distilled off, the residue was dissolved in water and extracted with ethyl acetate. The extract was washed with a sodium chloride aqueous solution and dried over magnesium sulfate. The solvent was distilled off to give oil (24 g.). The oil was subjected to column chromatography on silica gel using benzene as developing solvent. Firstly the eluate containing syn isomer was eluted and the eluate was collected and concentrated to give oil of methyl 2-methoxyimino-2-(3-methoxyphenyl)acetate (syn isomer) (9.2 g.).

I.R. spectrum (Film): 1738 cm$^{-1}$.

N.M.R. spectrum (CDCl$_3$, δ): ppm: 7.47–6.77 (4H, m); 4.00 (3H, s); 3.92 (3H, s); 3.82 (3H, s).

After the eluate containing syn isomer was eluted, then the eluate containing anti isomer was eluted. The eluate was collected and concentrated to give methyl 2-methoxyimino-2-(3-methoxyphenyl)acetate (anti isomer) (3.9 g.), mp 66° to 68° C. This substance was recrystallized from petroleum ether to give prisms, mp 65° to 65.5° C.

I.R. spectrum (Nujol): 1720 cm$^{-1}$.

N.M.R. spectrum (CDCl$_3$, δ): ppm: 7.14–7.44 (1H, m); 6.80–7.04 (3H, m); 4.02 (3H, s); 3.84 (3H, s); 3.76 (3H, s).

(b) Methyl 2-methoxyimino-2-(3-methoxyphenyl)acetate (syn isomer) (1.6 g.) and a 2 N aqueous solution of sodium hydroxide (4 ml.) were treated according to a similar manner to that of Preparation (5-3) (c) to give oil of 2-methoxyimino-2-(3-methoxyphenyl)acetic acid (syn isomer) (1.23 g.).

I.R. spectrum (Film): 1735 cm$^{-1}$.

Methyl 2-methoxyimino-2-(3-methoxyphenyl)acetate (anti isomer) (1.6 g.) and a 2 N aqueous solution of sodium hydroxide (4 ml.) were treated according to a similar manner to that of Preparation (5-3)(c) to give colorless prisms of 2-methoxyimino-2-(3-methoxyphenyl)acetic acid (anti isomer) (1.3 g.), mp 97° to 98° C.

I.R. spectrum (Nujol): 1695 cm$^{-1}$.

(9)(a) A solution of diazomethane in ether was added at ambient temperature to a solution of 2-methoxyimino-2-(3-chloro-4-hydroxyphenyl)acetic acid (syn isomer) (7 g.) in dry ether (50 ml.) until the color of the mixture was changed to yellow. Acetic acid was immediately added thereto and the reaction mixture was concentrated to dryness at 35° C. under reduced pressure. The residue was subjected to column chromatography on silica gel (120 g.) using a mixture of benzene and ethyl acetate (9:1) as a developing solvent. The first eluate was collected and concentrated at 40° C. under reduced pressure to give oil of methyl 2-methoxyimino-2-(3-chloro-4-methoxyphenyl)acetate (syn isomer) (3.1 g.).

I.R. spectrum (Film): 2850, 1735, 1610, 1600, 1250 cm$^{-1}$.

N.M.R. spectrum (CDCl$_3$, δ): ppm: 7.57 (1H, d, J=2 Hz); 7.37 (1H, dd, J=2,8 Hz); 6.87 (1H, d, J=8 Hz); 3.97 (3H, s); 3.91 (3H, s); 3.88 (3H, s).

(b) Methyl 2-methoxyimino-2-(3-chloro-4-methoxyphenyl)acetate (syn isomer) (2.7 g.) and a 2 N aqueous solution of sodium hydroxide (10.6 ml.) were treated according to a similar manner to that of Preparation (5-3) (c) to give crystals of 2-methoxyimino-2-(3-chloro-4-methoxyphenyl)acetic acid (syn isomer) (2.6 g.), mp 133° to 135° C. (dec.).

I.R. spectrum (Nujol): 2500–2600, 1745, 1610, 1600 cm$^{-1}$.

N.M.R. spectrum (CDCl$_3$, δ): ppm: 9.95 (1H, broad s); 7.72 (1H, d, J=2 Hz); 7.50 (1H, dd, J=2,8 Hz); 6.92 (1H, d, J=8 Hz); 4.08 (3H, s); 3.95 (3H, s).

(10)(a) A solution of 2-bromopropionyl bromide (25 g.) in dry chloroform (50 ml.) was dropwise added with stirring and ice-cooling to a solution of N,N-dimethylaniline (24 g.) in t-butanol (11 g.) and the mixture was refluxed for 2 hours. After cooling, the reaction mixture was poured into 6 N sulfuric acid (150 ml.) and extracted with ether. The extract was in turn washed with 6 N sulfuric acid, water, a 10% potassium carbonate aqueous solution and water and dried over magnesium sulfate. The solvent was distilled off to give oil of t-butyl 2-bromopropionate (21 g.).

(b) This oil (21 g.) was added with stirring at ambient temperature to a mixture of N-hydroxyphthalimide (16.3 g.), triethylamine (24 g.), dimethylformamide (20 ml.) and dimethylsulfoxide (20 ml.) and the resulting mixture was stirred for 4 hours at ambient temperature. The reaction mixture was poured into water (800 ml.) and precipitating materials were collected by filtration, washed with water and dried to give t-butyl 2-phthalimidoxypropionate (22.7 g.).

(c) This compound (22.7 g.) was dissolved in methylene chloride (200 ml.). A solution of 10% hydrazine hydrate (9 ml.) in methanol (20 ml.) was added thereto and the mixture was stirred for 2 hours at ambient temperature. Precipitating materials were dissolved by adding 5 N aqueous solution of ammonia and the aqueous layer was extracted with methylene chloride. Two methylene chloride layers were combined and dried over magnesium sulfate. The solvent was distilled off under reduced pressure to give oil of O-(1-t-butoxycarbonylethyl)hydroxylamine (13.5 g.).

I.R. spectrum (Film): 3350, 3250, 1745 cm$^{-1}$.

(d) 2-(3-Chloro-4-hydroxyphenyl)glyoxylic acid (2.0 g.) and O-(1-t-butoxycarbonylethyl)hydroxylamine (3.2 g.) were reacted according to a similar manner to that of Preparation (5-7) to give 2-(1-t-butoxycarbonylethoxyimino)-2-(3-chloro-4-hydroxyphenyl)acetic acid (syn isomer) (3.3 g.), mp 148° to 151° C.

I.R. spectrum (Nujol): 3450, 2500–2600, 1725, 1690, 1620, 1600 cm$^{-1}$.

N.M.R. spectrum (d$_6$-DMSO, δ): ppm: 7.46 (1H, d, J=2 Hz); 7.33 (1H, dd, J=2,8 Hz); 7.07 (1H, d, J=8 Hz); 4.67 (1H, q, J=6 Hz); 1.50 (12H, s).

(11) Phenolphthalein indicator (3 drops) was added to a solution of O-methylhydroxylamine hydrochloride (8.8 g.) in dry methanol (60 ml.). To the solution was dropwise added with stirring at ambient temperature 1 N methanol solution of sodium methoxide (105 ml.) until the color of the solution was changed to pale pink. O-Methylhydroxylamine hydrochloride was added thereto by small portions until the solution was changed to colorless solution. The pH value of the solution was 8.0 to 8.5. The mixture was stirred for 30 minutes at ambient temperature. After precipitating sodium chloride was filtered off, 2-(3-hydroxyphenyl)glyoxylic acid (16.6 g.) was added to the filtrate and the mixture was stirred for 1 hour at ambient temperature. After methanol was distilled off at low temperature, water was added to the residue. The mixture was adjusted to pH 7 with an aqueous solution of sodium bicarbonate, washed with ether, adjusted to pH 1 with 10% hydrochloric acid, subjected to salting-out and extracted with ether. The extract was washed with a saturated sodium chloride aqueous solution and dried over magnesium sulfate. Ether was distilled off and the operation that benzene was added to the residue and distilled off was repeated twice to give crystals of 2-methoxyimino-2-(3-hydroxyphenyl)acetic acid (syn isomer) (14.8 g.). This compound was identified with the compound obtained in Preparation (5-1)(c) by I.R. spectrum.

(12) A solution of 2-(3-methoxyphenyl)glyoxylic acid (1.8 g.) in an aqueous solution of sodium bicarbonate was adjusted to pH 7.0. On the other hand, a solution of O-ethylhydroxylamine hydrochloride (1.4 g.) in water (20 ml.) was adjusted to pH 7.0 with sodium bicarbonate. Two solutions were combined together, adjusted to pH 5.5 with 10% hydrochloric acid and stirred overnight at ambient temperature. The reaction mixture was adjusted to pH 7.5 with sodium bicarbonate and washed with ethyl acetate. The aqueous layer was adjusted to pH 1.0 with conc. hydrochloric acid under ice-cooling and extracted with ethyl acetate. The extract was washed with ice-water and dried over magnesium sulfate. The solvent was distilled off under reduced pressure to give oil of 2-ethoxyimino-2-(3-methoxyphenyl)acetic acid (syn isomer) (2.2 g.).

I.R. spectrum (Film): 2600, 1735, 1700, 1610, 1600 cm$^{-1}$.

(13) The following compounds were obtained according to similar manners to those of Preparations (5-5) to (5-7) and (5-10) to (5-12).

(1) 2-Ethoxyimino-2-(3-chloro-4-hydroxyphenyl)acetic acid (syn isomer), oil.

I.R. spectrum (Film): 3450, 2250–2600, 1700–1720, 1610, 1600 cm$^{-1}$.

(2) 2-Ethoxyimino-2-(3-hydroxyphenyl)acetic acid (syn isomer) oil.

I.R. spectrum (Film): 3400, 2600, 1700–1730, 1605, 1600 cm$^{-1}$.

(3) 2-(3-Hydroxy-4-bromobenzyloxyimino)-2-(4-hydroxyphenyl)acetic acid (syn isomer), colorless powder.

I.R. spectrum (Nujol): 3500, 3200, 1700 cm$^{-1}$.
N.M.R. spectrum (d$_6$-acetone, δ): ppm: 6.68–8.05 (7H, m); 5.15 (2H, s).

(4) 2-(2-Thienylmethoxyimino)-2-(4-hydroxyphenyl)acetic acid (syn isomer), powder.
I.R. spectrum (Nujol): 1705 cm$^{-1}$.
N.M.R. spectrum (d$_6$-DMSO, δ): ppm: 6.7–7.7 (7H, m); 5.28 (2H, s).

(5) 2-Allyloxyimino-2-(3-methoxyphenyl)acetic acid (syn isomer), oil.
I.R. spectrum (Film): 3050–3100, 2600, 1730, 1645, 1610, 1600 cm$^{-1}$.
N.M.R. spectrum (d$_6$-DMSO, δ): ppm: 7.00–7.50 (4H, m); 5.80–6.30 (1H, m); 5.33 (2H, t, J=9 Hz); 4.70 (2H, d, J=5 Hz); 3.82 (3H, s).

(6) 2-Allyloxyimino-2-(3-chloro-4-methoxyphenyl)acetic acid (syn isomer), pale yellow oil.
I.R. spectrum (Film): 3100, 2600, 1710–1730, 1645, 1610, 1600 cm$^{-1}$.
N.M.R. spectrum (d$_6$-DMSO, δ): ppm: 7.63 (1H, d, J=2 Hz); 7.50 (1H, dd, J=2,8 Hz); 7.23 (1H, d, J=8 Hz); 5.9–6.3 (1H, m); 5.33 (2H, t, J=9 Hz); 4.73 (2H, d, J=5 Hz); 3.91 (3H, s).

(7) 2-Phenylthiomethoxyimino-2-(3-hydroxyphenyl)acetic acid (syn isomer), oil.
I.R. spectrum (Film): 3300, 1730 cm$^{-1}$.
N.M.R. spectrum (CDCl$_3$, δ): ppm: 6.8–7.7 (9H, m); 5.54 (2H, s).

(8) 2-Methoxyimino-2-(3-mesylaminophenyl) acetic acid (syn isomer), mp 128° C. (dec.).
I.R. spectrum (Nujol): 3300, 1740 cm$^{-1}$.

(9) 2-(3-Phenylallyloxyimino)-2-(3-hydroxyphenyl)acetic acid (syn isomer), mp 115° to 116° C.
I.R. spectrum (Nujol): 3400, 1725 cm$^{-1}$.

(10) 2-Methoxyimino-2-(4-dimethylamino-phenyl)acetic acid (syn isomer), mp 88° to 89° C. (dec.).
I.R. spectrum (Nujol): 2700–2100, 1720, 1660, 1612, 1590 cm$^{-1}$.

(14) Acetyl chloride (4.1 g.) was added with stirring and ice-cooling to a solution of 2-methoxyimino-2-(3-hydroxyphenyl)acetic acid (syn isomer) (5 g.) in pyridine (20 ml.) and the mixture was stirred for 50 minutes at ambient temperature. The reaction mixture was poured into ice-water, adjusted to pH 2.1 and extracted three times with ether. The extract was washed with a saturated sodium chloride aqueous solution and dried over magnesium sulfate. The solvent was thoroughly removed under reduced pressure to give 2-methoxyimino-2-(3-acetoxyphenyl)acetic acid (syn isomer) (6.1 g.).
I.R. spectrum (Film): 3500, 2950, 1760, 1735, 1605, 1575, 1485, 1440, 1425, 1370 cm$^{-1}$.
N.M.R. spectrum (CDCl$_3$, δ): ppm: 7.94 (1H, s); 7.6–7.0 (4H, m); 4.05 (3H, s); 2.30 (3H, s).

(15) Trichloroacetyl isocyanate (70 ml) was dropwise added over 6 minutes at ambient temperature to a solution of 2-methoxyimino-2-(3-hydroxyphenyl)acetic acid (syn isomer) (40 g) in dry dioxane (200 ml), and the resulting mixture was stirred for 5 hours at ambient temperature. Dioxane was distilled off and to the residue were added ethyl acetate (200 ml) and by small portions water (200 ml) under ice-cooling. The mixture containing trichloroacetylcarbamoyl 2-methoxyimino-2-(3-trichloroacetylcarbamoyloxyphenyl)acetate was stirred for 5 hours at ambient temperature keeping the pH value of the mixture at 6.0 to 6.4 by adding an aqueous solution of sodium bicarbonate. The resulting mixture was wahsed twice with ethyl acetate. The aqueous layer was adjusted to pH 2 with a 10% hydrochloric acid and extracted three times with ethyl acetate. The combined ethyl acetate extracts were washed twice with an aqueous solution of sodium chloride and dried over magnesium sulfate. The solvent was distilled off and precipitating crystals were collected by filtration to give colorless crystals of 2-methoxyimino-2-(3-carbamoyloxyphenyl)acetic acid (syn isomer) (15 g), mp 163° C. (dec.). The same compound (5.4 g) was obtained from the mother liquor.
I.R. spectrum (Nujol): 3480, 3360, 1730, 1660 cm$^{-1}$.
N.M.R. spectrum (d$_6$-DMSO, δ): ppm: 3.97 (3H, s), 7.16 (2H, broad s), 7.1–7.7 (4H, m), 9.7 (1H, broad s).

Preparation 6

(1) A solution of sodium nitrite (12.4 g.) in water (150 ml.) was dropwise added with stirring at 5° to 7° C. to a solution of ethyl 4-bromoacetoacetate (30 g.) in acetic acid (200 ml.) and the mixture was stirred for 2 hours at 10° C. Water (200 ml.) was added to the reaction mixture and the resultant mixture was extracted with ether (500 ml.). The extract was washed twice with water (200 ml.) and with a sodium chloride aqueous solution (200 ml.) and dried over magnesium sulfate. The solvent was distilled off under reduced pressure to give yellowish brown crystals of ethyl 2-hydroxyimino-4-bromoacetoacetate (a mixture of syn and anti isomers) (32.6 g.).
I.R. spectrum (Film): 3350, 1740, 1710, 1620 cm$^{-1}$.
N.M.R. spectrum (CDCl$_3$, δ): ppm: 8.75 (2H, broad s); 4.35 (8H, m); 1.35 (6H, m).

(2) Pulverized potassium carbonate (160 g.) was added to a solution of ethyl 2-hydroxyiminoacetoacetate (a mixture of syn and anti isomers) (152 g.) in acetone (500 ml.). Dimethyl sulfate (130 g.) was dropwise added thereto with stirring over 1 hour at 45° to 50° C. and the mixture was stirred for 2 hours. An insoluble material was filtered off and the filtrate was concentrated under reduced pressure. The filtered insoluble material was dissolved in water (500 ml.) and this solution was added to the residue. The mixture was extracted twice with ethyl acetate (300 ml.). The extract was washed twice with water (200 ml.) and with a saturated sodium chloride aqueous solution (200 ml.) and dried over magnesium sulfate. The solvent was distilled off under reduced pressure and the residue was distilled under reduced pressure to give colorless oil of ethyl 2-methoxyiminoacetoacetate (a mixture of syn and anti isomers) (145.3 g.), bp 55° to 64° C./0.5 mm Hg.
I.R. spectrum (Film): 1745, 1695, 1600 cm$^{-1}$.
N.M.R. spectrum (CDCl$_3$, δ): ppm: 4.33 (4H, q, J=8 Hz); 4.08 (3H, s); 3.95 (3H, s); 2.40 (3H, s); 1.63 (3H, s); 1.33 (6H, t, J=8 Hz). p (3) Bromine (100 g.) was dropwise added over 40 minutes under reflux to a solution of ethyl 2-methoxyiminoacetoacetate (a mixture of syn and anti isomers) (100 g.) in a mixture of carbon tetrachloride (300 ml.) and acetic acid (300 ml.). The mixture was stirred at 70° to 80° C. until the evolution of hydrogen bromide ceased. The reaction mixture was washed twice with water (300 ml.), a sodium bicarbonate aqueous solution and a saturated sodium chloride aqueous solution and dried over magnesium sulfate. The solution was treated with activated charcoal (2 g.) and concentrated under reduced pressure to give ethyl 2-methoxyimino-4-bromoacetoacetate (a mixture of syn and anti isomers) (120.8 g.).
I.R. spectrum (Film): 1740, 1705, 1600 cm$^{-1}$.
N.M.R. spectrum (CDCl$_3$, δ): ppm: 4.17–4.54 (8H, m); 4.15 (3H, s); 4.13 (3H, s); 1.33 (6H, t, J=8 Hz).

(4) A mixture of selenium dioxide (11.1 g.), dioxane (250 ml.) and water (5 ml.) was stirred for 15 minutes at 110° to 115° C. to give yellow solution. Ethyl 2-(2-mesylamino-1,3-thiazol-4-yl)acetate (26.4 g) was added thereto with stirring at the same temperature. After stirring for 1 hour, the reaction mixture was decanted with heating and cooled to precipitate yellow crystals. The crystals were collected by filtration, washed with dioxane and ether and dried to give ethyl 2-(2-mesylamino-1,3-thiazol-4-yl)glyoxylate (23.5 g.).

I.R. spectrum (Nujol): 3300, 1718, 1682 cm$^{-1}$.

(5) Ethyl 2-(2-mesylamino-1,3-thiazol-4-yl)glyoxylate (13.9 g.) was added with stirring at ambient temperature to a solution of sodium hydroxide (5.0 g.) in water (150 ml.). The mixture was stirred for 1 hour at ambient temperature, adjusted to pH 7 with conc. hydrochloric acid and washed with ethyl acetate. The aqueous layer was adjusted to pH 0.5 with conc. hydrochloric acid to precipitate yellow crystals. The crystals were collected by filtration, washed with water and dried to give 2-(2-mesylamino-1,3-thiazol-4-yl)glyoxylic acid (10.16 g.).

I.R. spectrum (Nujol): 3350, 1725, 1650 cm$^{-1}$.

(6) To a solution of ethyl 2-(2-amino-1,3-thiazol-4-yl)acetate (14 g.) in a mixture of pyridine (40 g.) and methylene chloride (300 ml.) was gradually added diethyl ether solution of t-pentyl chloroformate (70 ml.) containing 0.35 mole of t-pentyl chloroformate over 10 minutes at −20° C. with stirring, and the mixture was stirred for 2 hours at the same temperature and further stirred for 0.5 hour at 0° C. After the reaction, the reaction mixture was poured into water (200 ml.), and then the organic layer was separated. The organic layer was washed with 2 N hydrochloric acid, water, 5% sodium bicarbonate aqueous solution and water in turn and then dried over magnesium sulfate. The solvent was distilled off from the organic layer to give dark brown oil of ethyl 2-(2-t-pentyloxycarbonylamino-1,3-thiazol-4-yl)acetate (12 g.).

I.R. spectrum (liquid): 1667, 1660 (CO) cm$^{-1}$.

N.M.R. spectrum (CDCl$_3$, δ): ppm: 3.75 (2H, s); 6.75 (1H, s).

(7) Ethyl 2-(2-t-pentyloxycarbonylamino-1,3-thiazol-4-yl)acetate (0.3 g.) and selenium dioxide (0.11 g.) were treated according to a similar manner to that of Preparation (6-4) to give brown oil of ethyl 2-(2-t-pentyloxycarbonylamino-1,3-thiazol-4-yl)glyoxylate (0.22 g.).

I.R. spectrum (liquid): 1720, 1690 (CO) cm$^{-1}$.

N.M.R. spectrum (CDCl$_3$, δ): ppm: 8.3 (1H, s).

(8) Ethyl 2-(2-t-pentyloxycarbonylamino-1,3-thiazol-4-yl)glyoxylate (2.8 g.) and a solution of sodium hydroxide (0.54 g.) in water (20 ml.) were treated according to a similar manner to that of Preparation (6-5) to give brown powder of 2-(2-t-pentyloxycarbonylamino-1,3-thiazol-4-yl)glyoxylic acid (1.75 g.).

I.R. spectrum (Nujol): 1730, 1680 (CO) cm$^{-1}$.

N.M.R. spectrum (d$_6$-dimethylsulfoxide, δ): ppm: 8.4 (1H, s).

(9) A mixture of ethyl 2-hydroxyimino-2-(2-amino-1,3-thiazol-4-yl)acetate (a mixture of syn and anti isomers) (0.37 g), ethanol (5 ml), water (5 ml) and sodium bisulfite (0.72 g) was stirred for 12 hours at 65° to 70° C. The reaction mixture was concentrated and water (10 ml) was added to the residue. The resulting mixture was subjected to salting-out and extracted with ethyl acetate. The extract was dried over magnesium sulfate and concentrated to give yellow crystals of ethyl 2-(2-amino-1,3-thiazol-4-yl)glyoxylate (0.18 g), mp 115° to 120° C.

I.R. spectrum (Nujol): 3420, 3250, 3120, 1730, 1665, 1612 cm$^{-1}$.

(10) Sulfuryl chloride (235 ml.) was dropwise added over 20 minutes with stirring and ice-cooling to a solution of ethyl 2-methoxyiminoacetoacetate (syn isomer) (500 g.) in acetic acid (500 ml.), and the mixture was stirred overnight under cooling with water. Nitrogen gas was introduced to the reaction mixture for 2 hours, and the resulting mixture was poured into water (2.5 l). After extracting with methylene chloride (500 ml.) and twice with methylene chloride (200 ml.), the extracts were combined. The combined extracts were washed with a saturated aqueous solution of sodium chloride, and adjusted to pH 6.5 by adding water (800 ml.) and sodium bicarbonate. Methylene chloride layer was separated, washed with an aqueous solution of sodium chloride and dried over magnesium sulfate. The solvent was distilled off to give ethyl 2-methoxyimino-4-chloroacetoacetate (syn isomer) (559 g.).

I.R. spectrum (Film): 1735, 1705 cm$^{-1}$.

(11) To a suspension of ethyl 2-hydroxyimino-3-oxobutyrate (syn isomer) (40 g.) and potassium carbonate (52 g.) in dimethylformamide (200 ml.) was added pentyl bromide (37.9 g.) with stirring, and the mixture was stirred for 1.5 hours at ambient temperature. The insoluble material was collected by filtration and washed with dimethylformamide. The filtrate and the washings were combined together and evaporated to dryness under reduced pressure. To the residue was added water and the mixture was extracted with chloroform. The extract was washed with a saturated aqueous solution of sodium chloride, dried over magnesium sulfate and concentrated under reduced pressure to give an oil of ethyl 2-pentyloxyimino-3-oxobutyrate (syn isomer) (57.5 g.).

I.R. (Film): 1745, 1680, 1470 cm$^{-1}$.

N.M.R. (CCl$_4$, δ): 4.1–4.6 (4H, m), 2.36 (3H, s), 0.7–2.2 (12H, m).

(12) Ethyl 2-pentyloxyimino-3-oxobutyrate (syn isomer) (57.5 g.) and sulfuryl chloride (20.9 ml.) were reacted in acetic acid (58.5 ml.) according to a similar manner to that of Preparation (6-10) to give an oil of ethyl 2-pentyloxyimino-3-oxo-4-chlorobutyrate (syn isomer) (51.1 g.).

I.R. (Film): 1750, 1715, 1470 cm$^{-1}$.

N.M.R. (CCl$_4$, δ): 4.48 (2H, s), 4.1–4.6 (4H, m), 0.7–2.1 (11H, m).

Preparation 7

(1) A mixture of ethyl 2-hydroxyimino-4-bromoacetoacetate (a mixture of syn and anti isomers) (22.0 g.), thioacetamide (7.5 g.) and benzene (100 ml.) was refluxed for 3 hours. After cooling triethylamine (10 g.) was added thereto and the mixture was stirred for 1 hour. An insoluble material was filtered off and the filtrate was concentrated under reduced pressure to give ethyl 2-hydroxyimino-2-(2-methyl-1,3-thiazol-4-yl)acetate (a mixture of syn and anti isomers) (8.6 g.). This substance was subjected to column chromatography on silica gel (80 g.) using benzene as developing solvent. Firstly the eluate containing anti isomer was eluted, collected and concentrated to give ethyl 2-hydroxyimino-2-(2-methyl-1,3-thiazol-4-yl)acetate (anti isomer) (2.5 g.), mp 90° to 92° C.

I.R. spectrum (Nujol): 1720 cm$^{-1}$.

N.M.R. spectrum (d$_6$-DMSO, δ): ppm: 12.55 (1H, s); 8.25 (1H, s); 4.27 (2H, q, J=7 Hz); 2.63 (3H, s); 1.25 (3H, t, J=7 Hz).

After the eluate containing anti isomer was eluted, the eluate containing syn isomer was eluted, collected and concentrated to give ethyl 2-hydroxyimino-2-(2-methyl-1,3-thiazol-4-yl)acetate (syn isomer) (0.5 g.), mp 134° to 136° C.

I.R. spectrum (Nujol): 1720 cm$^{-1}$.

N.M.R. spectrum (d$_6$-DMSO, $\delta$): ppm: 11.81 (1H, s); 7.81 (1H, s); 4.35 (2H, q, J=7 Hz); 2.70 (3H, s); 1.30 (3H, t, J=7 Hz).

(2) Phenolphthalein indicator (3 drops) was added to a solution of hydroxylamine hydrochloride (4.2 g.) in dry methanol (60 ml.). To the solution was dropwise added with stirring at ambient temperature 1 N methanol solution of sodium methoxide (60 ml.) until the color of the solution was changed to purplish red. Hydroxylamine hydrochloride was added thereto by small portions until the solution was changed to colorless solution. The mixture was stirred for 30 minutes at ambient temperature. After precipitating sodium chloride was filtered off, 2-(2-mesylamino-1,3-thiazol-4-yl)glyoxylic acid (12.5 g.) was added to the filtrate and the mixture was refluxed with stirring for 1.5 hours. The reaction mixture was cooled to precipitate crystals. The crystals were collected by filtration and dried to give crude 2-hydroxyimino-2-(2-mesylamino-1,3-thiazol-4-yl)acetic acid (a mixture of syn and anti isomers) (5.5 g.). The filtrate was concentrated to the volume of ¼ and ether was added thereto. Precipitating crystals were collected by filtration, washed with ether and dried to give the same compound (8.78 g.). Total yield (14.3 g.).

(3) A mixture of ethyl 2-hydroxyimino-4-bromoacetoacetate (a mixture of syn and anti isomers) (2.4 g) and thiourea (0.76 g) in ethanol (15 ml) was stirred for 1 hour at 60° C. Ethanol was distilled off under reduced pressure and water was added to the residue. The resultant mixture was adjusted to pH 1.0 and washed with ethyl acetate. The aqueous layer was adjusted to pH 4.5 with triethylamine and extracted with ethyl acetate. The extract was washed with water and a saturated sodium chloride aqueous solution and dried over magnesium sulfate. The solvent was distilled off under reduced pressure and the residue was subjected to column chromatography on silica gel using a mixture of ethyl acetate and benzene (1:3) as developing solvent. The eluates containing syn isomer were collected and concentrated to give ethyl 2-hydroxyimino-2-(2-amino-1,3-thiazol-4-yl)acetate (syn isomer) (0.3 g).

I.R. spectrum (Nujol): 3450, 3300, 3200, 1725, 1620 cm$^{-1}$.

N.M.R. spectrum (CDCl$_3$, $\delta$): ppm: 7.65 (1H, s); 5.33 (2H, broad s); 4.40 (2H, q, J=7.5 Hz); 1.38 (3H, t, J=7.5 Hz).

After the eluates containing syn isomers were collected, the eluates containing a mixture of syn and anti isomers were collected and concentrated to give ethyl 2-hydroxyimino-2-(2-amino-1,3-thiazol-4-yl)acetate (a mixture of syn and anti isomers) (0.3 g.).

I.R. spectrum (Nujol): 3400, 3300, 3200, 1715, 1620 cm$^{-1}$.

N.M.R. spectrum (d$_6$-DMSO, $\delta$): ppm: 12.42 (1H, broad s); 11.55 (1H, s); 7.52 (1H, s); 7.12 (4H, broad s); 6.83 (1H, s); 4.23 (4H, m); 1.26 (6H, m).

(4) A solution of ethyl 2-hydroxyimino-2-(2-amino-1,3-thiazol-4-yl)acetate (a mixture of syn and anti isomers) (1.1 g) in an 1 N aqueous solution of sodium hydroxide (15 ml) was allowed to stand for 2 hours at ambient temperature. The reaction mixture was adjusted to pH 3.5 with 10% hydrochloric acid and precipitating crystals were collected by filtration, washed with acetone and dried to give 2-hydroxyimino-2-(2-amino-1,3-thiazol-4-yl)acetic acid (a mixture of syn and anti isomers) (0.52 g), mp 184° to 186° C. (dec.).

I.R. spectrum (Nujol): 3200, 1670, 1530 cm$^{-1}$.

Preparation 8

(1) Thioacetamide (3.8 g.) was added to a solution of ethyl 2-methoxyimino-4-bromoacetoacetate (a mixture of syn and anti isomers) (12.6 g.) in ethanol (50 ml.) and the mixture was stirred for 5 hours at 50° C. Ethanol was distilled off under reduced pressure and water was added to the residue. The resulting mixture was extracted with ethyl acetate. The extract was in turn washed with water, a sodium bicarbonate aqueous solution and a saturated sodium chloride aqueous solution and dried over magnesium sulfate. The solvent was distilled off under reduced pressure to give ethyl 2-methoxyimino-2-(2-methyl-1,3-thiazol-4-yl)acetate (a mixture of syn and anti isomers) (9.0 g.).

(2) A mixture of ethyl 2-methoxyimino-4-bromoacetoacetate (a mixture of syn and anti isomers) (7.6 g.), O-ethyl thiocarbamate (3.0 g.) and dimethylacetamide (5 ml.) was stirred for 3 hours at 50° C. Ethyl acetate (50 ml.) was added to the reaction mixture and the resulting mixture was washed with water and with a saturated sodium chloride aqueous solution and dried over magnesium sulfate. Ethyl acetate was distilled off to give crystalline residue. The residue was washed with diisopropyl ether to give ethyl 2-methoxyimino-2-(2-oxo-2,3-dihydro-1,3-thiazol-4-yl)acetate (syn isomer) (2.35 g.).

I.R. spectrum (Nujol): 3200, 1735, 1680, 1650 cm$^{-1}$.

N.M.R. spectrum (CDCl$_3$, $\delta$): ppm: 9.13 (1H, broad s); 6.37 (1H, s); 4.40 (2H, q, J=6 Hz); 4.01 (3H, s); 1.38 (3H, t, J=6 Hz).

The mother liquor of diisopropyl ether was concentrated and the residue was subjected to column chromatography on silica gel (70 g.) using a mixture of benzene and ethyl acetate (9:1) as developing solvent. The eluate containing syn isomer was collected and concentrated to further give the above obtained syn isomer (0.65 g.). Total yield (3.0 g.). Thereafter a mixture of benzene and ethyl acetate (5:1) was used as developing solvent. The eluate containing anti isomer was collected and concentrated to give ethyl 2-methoxyimino-2-(2-oxo-2,3-dihydro-1,3-thiazol-4-yl)acetate (anti isomer) (0.26 g.).

I.R. spectrum (Nujol): 3250, 3200, 1720, 1690 cm$^{-1}$.

N.M.R. spectrum (CDCl$_3$, $\delta$): ppm: 9.90 (1H, broad s); 7.30 (1H, s); 4.40 (2H, q, J=6 Hz); 4.03 (3H, s); 1.38 (3H, t, J=6 Hz).

(3) A solution of ethyl 2-methoxyimino-4-bromoacetoacetate (a mixture of syn and anti isomers) (17.4 g.) and thiourea (5.4 g.) in ethanol (100 ml.) was refluxed for 4 hours. The reaction mixture was allowed to stand and cooled in refrigerator to precipitate crystals. The crystals were collected by filtration, washed with ethanol and dried to give ethyl 2-methoxyimino-2-(2-amino-1,3-thiazol-4-yl)acetate hydrobromide (anti isomer) (9.5 g.). The filtrate and the washings were put together and concentrated under reduced pressure. Water (100 ml.) was added to the residue and the mixture was washed with ether. The aqueous layer was alkalized with a 28% aqueous solution of ammonia and extracted with ethyl acetate. The extract was washed with water and a saturated sodium chloride aqueous solution and dried over magnesium sulfate. The solvent was distilled off under reduced pressure to give crystalline substance of ethyl 2-methoxyimino-2-(2-amino-1,3-thiazol-4-yl)acetate (syn isomer) (5.2 g.).

I.R. spectrum (Nujol): 3400, 3300, 3150, 1725, 1630, 1559 cm$^{-1}$.

N.M.R. spectrum (CDCl$_3$, δ): ppm: 6.72 (1H, s); 5.91 (2H, broad s); 4.38 (2H, q, J=7 Hz); 4.03 (3H, s); 1.38 (3H, t, J=7 Hz).

The above obtained ethyl 2-methoxyimino-2-(2-amino-1,3-thiazol-4-yl)acetate hydrobromide (anti isomer) (9.5 g.) was suspended in ethyl acetate (200 ml.) and triethylamine (4.0 g.) was added thereto. After stirring for 1 hour at ambient temperature, an insoluble material was filtered off and the filtrate was concentrated under reduced pressure to give crystalline substance of ethyl 2-methoxyimino-2-(2-amino-1,3-thiazol-4-yl)acetate (anti isomer) (6.15 g.).

I.R. spectrum (Nujol): 3450, 3250, 3150, 1730, 1620 cm$^{-1}$.

N.M.R. spectrum (CDCl$_3$, δ): ppm: 7.50 (1H, s); 5.60 (2H, broad s); 4.35 (2H, q, J=7 Hz); 4.08 (3H, s); 1.33 (3H, t, J=7 Hz).

(4) Phenolphthalein indicator (3 drops) was added to a solution of O-methyl-hydroxlyamine hydrochloride (1.25 g.) in dry methanol (15 ml.). To the solution was dropwise added with stirring at ambient temperature 1 N methanol solution of sodium methoxide (13 ml.) until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, ethyl 2-(2-mesylamino-1,3-thiazol-4-yl)glyoxylate (3.8 g.) was added to the filtrate and the mixture was refluxed with stirring for 2 hours. After methanol was distilled off, the residue was dissolved in ethyl acetate. An insoluble material was filtered off and the filtrate was concentrated. The residue was subjected to column chromatography on silica gel using a mixture of benzene and ethyl acetate (9:1) as developing solvent. The eluate containing syn isomer was collected and concentrated to give ethyl 2-methoxyimino-2-(2-mesylamino-1,3-thiazol-4-yl)acetate (syn isomer) (2.8 g.).

I.R. spectrum (Nujol): 1725 cm$^{-1}$.

N.M.R. spectrum (CDCl$_3$, δ): ppm: 6.76 (1H, s); 4.44 (2H, q, J=7 Hz); 4.04 (3H, s); 3.04 (3H, s); 1.37 (3H, t, J=7 Hz).

(5) Pulverized potassium carbonate (0.33 g.) was suspended in a solution of ethyl 2-hydroxyimino-2-(2-methyl-1,3-thiazol-4-yl)acetate (syn isomer) (0.5 g.) in acetone (20 ml.). A solution of dimethyl sulfate (0.3 g.) in acetone (5 ml.) was dropwise added thereto with stirring at 40° to 45° C. After stirring for 2 hours at the same temperature, an insoluble material was filtered off. The filtrate was concentrated and water was added to the residue. The resulting mixture was extracted with ethyl acetate. The extract was in turn washed with water, a sodium bicarbonate aqueous solution and a saturated sodium chloride aqueous solution and dried over magnesium sulfate. The solvent was distilled off under reduced pressure to give pale yellow oil of ethyl 2-methoxyimino-2-(2-methyl-1,3-thiazol-4-yl)acetate (syn isomer) (0.5 g.).

I.R. spectrum (Film): 1740, 1710, 1595 cm$^{-1}$.

N.M.R. spectrum (CDCl$_3$, δ): ppm: 7.40 (1H, s); 4.25 (2H, q, J=7 Hz); 4.03 (3H, s); 2.73 (3H, s); 1.38 (3H, t, J=7 Hz).

(6) 2-Hydroxyimino-2-(2-mesylamino-1,3-thiazol-4-yl) acetic acid (a mixture of syn and anti isomers) (14.3 g.) obtained in Preparation (7-2) was suspended in dry acetone (300 ml.). To the suspension were added potassium carbonate (22.8 g.) and dimethyl sulfate (20.8 g.). The mixture was refluxed with stirring for 9 hours. Acetone was distilled off from the reaction mixture and water was added to the residue. The resulting mixture was extracted with ethyl acetate. The extract was washed with a sodium chloride aqueous solution and dried over magnesium sulfate. The solvent was distilled off to give oil (13 g.). The oil was subjected to column chromatography on silica gel using a mixture of benzene and ethyl acetate (9:1) as developing solvent. Firstly the eluate containing anti isomer was eluted, collected and concentrated. The residual oil (2.4 g.) was triturated under cooling to crystallize. The crystals were collected by filtration by adding petroleum ether to give methyl 2-methoxyimino-2-(2-mesylimino-3-methyl-2,3-dihydro-1,3-thiazol-4-yl)acetate (anti isomer) (2.1 g.).

I.R. spectrum (Nujol): 1740 cm$^{-1}$.

N.M.R. spectrum (CDCl$_3$, δ): ppm: 7.90 (1H, s); 4.10 (3H, s); 3.90 (3H, s); 3.47 (3H, s); 3.07 (3H, s).

After the eluate containing anti isomer was eluted, the eluate containing syn isomer was eluted, collected and concentrated to give crystals of methyl 2-methoxyimino-2-(2-mesylimino-3-methyl-2,3-dihydro-1,3-thiazol-4-yl)acetate (syn isomer) (5.5 g.).

I.R. spectrum (Nujol): 1740 cm$^{-1}$.

N.M.R. spectrum (CDCl$_3$, δ): ppm: 6.72 (1H, s); 4.05 (3H, s); 3.92 (3H, s); 3.72 (3H, s); 3.01 (3H, s).

(7) The following compound was obtained according to a similar manner to that of Preparation (8-4). Ethyl 2-methoxyimino-2-(2-amino-1,3-thiazol-4-yl)acetate (syn isomer).

I.R. spectrum (Nujol): 3400, 3300, 3150, 1725, 1630, 1559 cm$^{-1}$.

N.M.R. spectrum (CDCl$_3$, δ): ppm: 6.72 (1H, s); 5.91 (2H, broad s); 4.38 (2H, q, J=7 Hz); 4.03 (3H, s); 1.38 (3H, t, J=7 Hz).

(8) A mixture of acetic anhydride (6.1 g) and formic acid (2.8 g) was stirred for 2 hours at 50° C. The resulting mixture was cooled and ethyl 2-methoxyimino-2-(2-amino-1,3-thiazol-4-yl)acetate (syn isomer) (4.6 g) was added thereto at 15° C. After the mixture was stirred for 3.5 hours at ambient temperature, cooled water (100 ml) was added thereto. The resulting mixture was extracted with ethyl acetate (200 ml). The extract was washed with water and then with a saturated aqueous solution of sodium bicarbonate until the washing was changed to weakly alkaline solution. The extract was further washed with a saturated aqueous solution of sodium chloride and dried over magnesium sulfate. The solvent was distilled off and the residue was washed with diisopropyl ether, collected by filtration and dried to give ethyl 2-methoxyimino-2-(2-formamido-1,3-thiazol-4-yl)acetate (syn isomer) (4.22 g), mp 122° to 124° C. (dec.).

I.R. spectrum (Nujol): 3150, 1728, 1700 cm$^{-1}$.

N.M.R. spectrum (CDCl$_3$, δ): ppm: 12.58 (1H, broad s), 8.95 (1H, s), 7.17 (1H, s), 4.42 (2H, q, J=8 Hz), 4.00 (3H, s), 1.37 (3H, t, J=8 Hz).

(9) Pyridine (3 g.) was added to a solution of ethyl 2-methoxyimino-2-(2-amino-1,3-thiazol-4-yl)acetate (syn isomer) (6.5 g.) in a mixture of ethyl acetate (60 ml.) and dimethylformamide (20 ml.). To the solution was dropwise added with stirring at 4° C. ethyl chloroformate (8 g.). After adding water (50 ml.) to the reaction mixture, the organic layer was separated, washed with water and then with a saturated aqueous solution of sodium chloride and dried over magnesium sulfate. The solvent was distilled off under reduced pressure. The residue was subjected to column chromatography on silica gel (120 g.) using a mixture of ether and petroleum ether (5:2) as an eluent to give ethyl 2-methoxyimino-2-(2-ethoxycarbonylamino-1,3-thiazol-4-yl)acetate (syn isomer) (5.4 g.).

N.M.R. spectrum (CDCl$_3$, δ): ppm: 9.36 (1H, broad s); 7.10 (1H, s); 4.00–4.66 (4H, m); 4.00 (3H, s); 1.20–1.60 (6H, m).

(10) Ethyl 2-methoxyimino-4-chloroacetoacetate (syn isomer) (50 g.) was added over 3 minutes with stirring at ambient temperature to a solution of thiourea (18.4 g.) and sodium acetate (19.8 g.) in a mixture of methanol (250 ml.) and water (250 ml.). After stirring for 35 minutes at 40° to 45° C., the reaction mixture was cooled with ice and adjusted to pH 6.3 with a saturated aqueous solution of sodium bicarbonate. After stirring for 30 minutes at the same temperature, precipitates were collected by filtration, washed with water (200 ml.) and then with diisopropyl ether (100 ml.), and dried to give colorless crystals of ethyl 2-methoxyimino-2-(2-amino-1,3-thiazol-4-yl)acetate (syn isomer) (37.8 g.), mp 161° to 162° C.

I.R. spectrum (Nujol): 3400, 3300, 3150, 1725, 1630, 1559 cm$^{-1}$.

N.M.R. spectrum (CDCl$_3$, δ): ppm: 6.72 (1H, s); 5.91 (2H, broad s); 4.38 (2H, q, J=7 Hz); 4.03 (3H, s); 1.38 (3H, t, J=7 Hz).

(11) Ethyl 2-hydroxyimino-2-(2-methyl-1,3-thiazol-4-yl)acetate (anti isomer) (0.3 g.) and dimethyl sulfate (0.18 g.) were reacted according to a similar manner to that of Preparation (8-5) to give pale yellow oil of ethyl 2-methoxyimino-2-(2-methyl-1,3-thiazol-4-yl)acetate (anti isomer) (0.27 g.).

I.R. spectrum (Film): 1750, 1605 cm$^{-1}$.

N.M.R. spectrum (CDCl$_3$, δ): ppm: 8.07 (1H, s); 4.41 (2H, q, J=7 Hz); 4.13 (3H, s); 2.75 (3H, s); 1.40 (3H, t, J=7 Hz).

(12) The following compound was obtained according to a similar manner to that of Preparation (8-8).

Ethyl 2-methoxyimino-2-(2-formamido-1,3-thiazol-4-yl)acetate (anti isomer), mp 96° to 99° C. (dec.).

I.R. spectrum (Nujol): 3150, 1740, 1650, 1600 cm$^{-1}$.

N.M.R. spectrum (CDCl$_3$, δ): ppm: 11.20 (1H, broad s), 8.60 (1H, s), 7.90 (1H, s), 4.32 (2H, q, J=8 Hz), 4.13 (3H, s), 1.32 (3H, t, J=8 Hz).

(13) Ethyl 2-pentyloxyimino-3-oxo-4-chlorobutyrate (syn isomer) (51.1 g.) and thiourea (14.7 g.) were reacted in the presence of sodium acetate trihydrate (26.4 g.) in a mixture of water (125 ml.) and ethanol (175 ml.) according to a similar manner to that of Preparation (8-10) to give crystals of ethyl 2-pentyloxyimino-2-(2-amino-1,3-thiazol-4-yl)acetate (syn isomer) (28.7 g.), mp 86° to 88° C.

I.R. (Nujol): 3450, 3250, 3130, 1715, 1535 cm$^{-1}$.

N.M.R. (d$_6$-DMSO, δ): 7.25 (2H, s), 6.90 (1H, s), 4.32 (2H, q, J=7 Hz), 4.11 (2H, t, J=6 Hz), 0.6–2.0 (12H, m).

Preparation 9

(1) Ethanol (10 ml.) was added to a suspension of ethyl 2-methoxyimino-2-(2-amino-1,3-thiazol-4-yl)acetate (syn isomer) (2.2 g.) in a 1 N aqueous solution of sodium hydroxide (12 ml.) and the mixture was stirred for 15 hours at ambient temperature. The reaction mixture was adjusted to pH 7.0 with 10% hydrochloric acid and ethanol was distilled off under reduced pressure. The residual aqueous solution was washed with ethyl acetate, adjusted to pH 2.8 with 10% hydrochloric acid and stirred under ice-cooling to precipitate crystals. The crystals were collected by filtration, washed with acetone and recrystallized from ethanol to give colorless needles of 2-methoxyimino-2-(2-amino-1,3-thiazol-4-yl)acetic acid (syn isomer) (1.1 g.).

I.R. spectrum (Nujol): 3150, 1670, 1610, 1585 cm$^{-1}$.

N.M.R. spectrum (d$_6$-DMSO, δ): ppm: 7.20 (2H, broad s); 6.85 (1H, s); 3.83 (3H, s).

(2) 1N-Aqueous solution of sodium hydroxide (1.5 ml.) was added to a solution of ethyl 2-methoxyimino-2-(2-methyl-1,3-thiazol-4-yl)acetate (syn isomer) (0.3 g.) in ethanol (5 ml.) and the resulting mixture was stirred for 2 hours at 40° C. The reaction mixture was adjusted to pH 7.0 with 10% hydrochloric acid, concentrated under reduced pressure, adjusted to pH 1.5 with 10% hydrochloric acid and extracted with ethyl acetate. The extract was washed with water and a saturated sodium chloride aqueous solution and dried over magnesium sulfate. The solvent was distilled off to give crystalline substance of 2-methoxyimino-2-(2-methyl-1,3-thiazol-4-yl)acetic acid (syn isomer) (0.14 g.).

I.R. spectrum (Nujol): 1730 cm$^{-1}$.

N.M.R. spectrum (d$_6$-DMSO, δ): ppm: 7.80 (1H, s); 3.85 (3H, s); 2.62 (3H, s).

(3) The following compounds were obtained according to similar manners to those of Preparation (9-1) to (9-2).

(1) 2-Methoxyimino-2-(2-oxo-2,3-dihydro-1,3-thiazol-4-yl)acetic acid (syn isomer).

I.R. spectrum (Nujol): 3250, 1710, 1650 cm$^{-1}$.

N.M.R. spectrum (d$_6$-DMSO, δ): ppm: 10.61 (1H, broad s); 6.73 (1H, s); 3.95 (3H, s).

(2) 2-Methoxyimino-2-(2-mesylamino-1,3-thiazol-4-yl)acetic acid (syn isomer).

I.R. spectrum (Nujol): 3150, 1720 cm$^{-1}$.

N.M.R. spectrum (d$_6$-DMSO, δ): ppm: 7.17 (1H, s); 3.93 (3H, s); 3.02 (3H, s).

(3) 2-Methoxyimino-2-(2-mesylimino-3-methyl-2,3-dihydro-1,3-thiazol-4-yl)acetic acid (syn isomer).

I.R. Spectrum (Nujol): 1730 cm$^{-1}$.

(4) 2-Methoxyimino-2-(2-formamido-1,3-thiazol-4-yl)acetic acid (syn isomer), mp 152° C. (dec.).

I.R. spectrum (Nujol): 3200, 2800–2100, 1950, 1600 cm$^{-1}$.

N.M.R. spectrum (d$_6$-DMSO, δ): ppm: 8.60 (1H, s); 7.62 (1H, s); 3.98 (1H, s).

(5) 2-Methoxyimino-2-(2-ethoxycarbonylamino-1,3-thiazol-4-yl)acetic acid (syn isomer).

I.R. spectrum (Nujol): 3200, 1730, 1710, 1690, 1570 cm$^{-1}$.

N.M.R. spectrum (d$_6$-DMSO, δ): ppm: 12.16 (1H, broad s); 7.50 (1H, s); 7.20 (1H, broad s); 4.25 (2H, q, J=7 Hz); 3.93 (3H, s); 1.25 (3H, t, J=7 Hz).

(4) Pyridine (5 ml.) was added to a suspension of 2-methoxyimino-2-(2-amino-1,3-thiazol-4-yl)acetic acid (syn isomer) (2.0 g.) in ethyl acetate (20 ml.). A solution of bis(2,2,2-trifluoroacetic)anhydride (2.5 g.) in ethyl acetate (3 ml.) was dropwise added thereto with stirring at 5° to 7° C. and the mixture was stirred for 30 minutes at 3° to 5° C. Water (30 ml.) was added to the reaction mixture and the ethyl acetate layer was separated. The aqueous layer was further extracted with ethyl acetate and two ethyl acetate layers were combined together, washed with water and a saturated sodium chloride aqueous solution and dried over magnesium sulfate. The solvent was distilled off under reduced pressure to give 2-methoxyimino-2-[2-(2,2,2-trifluoroacetamido)-1,3-thiazol-4-yl]acetic acid (syn isomer) (0.72 g.).

I.R. spectrum (Nujol): 1725, 1590 cm$^{-1}$.

N.M.R. spectrum (d$_6$-DMSO, δ): ppm: 7.68 (1H, s); 3.91 (3H, s).

(5) The following compound was obtained according to a similar manner to that of Preparation (9-4).

2-Methoxyimino-2-(2-acetamido-1,3-thiazol-4-yl)acetic acid (syn isomer), mp 184° to 185° C. (dec.).

I.R. spectrum (Nujol): 3200, 3050, 1695, 1600 cm$^{-1}$.

(6) Phenolphthalein indicator (3 drops) was added to a solution of O-allyl-hydroxylamine hydrochloride (0.84 g.) in dry methanol (10 ml.). To the solution was dropwise added with stirring at ambient temperature 1 N methanol solution of sodium methoxide (6 ml.) until the color of the solution was changed to pale pink. O-Allylhydroxylamine hydrochloride was added thereto by small portions until the solution was changed to colorless solution. The mixture was stirred for 30 minutes at ambient temperature. After precipitating sodium chloride was filtered off, 2-(2-t-pentyloxycarbonylamino-1,3-thiazol-4-yl)glyoxylic acid (2.0 g.) was added to the filtrate and the mixture was stirred for 1 hour at ambient temperature. After methanol was distilled off at low temperature, the residue was dissolved in an 1 N aqueous solution of sodium hydroxide. The solution was washed with ether and ethyl acetate was added thereto. The mixture was adjusted to pH 1.5 with phosphoric acid and extracted with ethyl acetate. The extract was washed with a sodium chloride aqueous solution and dried over magnesium sulfate. Ethyl acetate was distilled off and the residue was washed with diisopropyl ether, collected by filtration and dried to give 2-allyloxyimino-2-(2-t-pentyloxycarbonylamino-1,3-thiazol-4-yl)acetic acid (syn isomer) (1.62 g.).

I.R. spectrum (Nujol): 3200, 1712 cm$^{-1}$.

N.M.R. spectrum (d$_6$-DMSO, δ): ppm: 7.40 (1H, s); 6.24–5.76 (1H, m); 5.26 (2H, dd, J=9, 10 Hz); 4.65 (2H, d, J=5 Hz); 1.78 (2H, q, J=8 Hz); 1.44 (6H, s); 0.88 (3H, t, J=8 Hz).

(7) The following compounds were obtained according to a similar manner to that of Preparation (9-6).

(1) 2-Methoxyimino-2-(2-t-pentyloxycarbonylamino-1,3-thiazol-4-yl)acetic acid (syn isomer).

I.R. spectrum (Nujol): 3200, 1712 cm$^{-1}$.

N.M.R. spectrum (d$_6$-DMSO, δ): ppm: 7.40 (1H, s); 3.88 (3H, s); 1.77 (2H, q, J=8 Hz); 1.44 (6H, s); 0.88 (3H, t, J=8 Hz).

(2) 2-Allyloxyimino-2-(2-mesylamino-1,3-thiazol-4-yl)acetic acid (syn isomer).

I.R. spectrum (Nujol): 3150, 1710, 1605 cm$^{-1}$.

(3) 2-Methoxyimino-2-(2-amino-1,3-thiazol-4-yl)acetic acid (syn isomer).

I.R. spectrum (Nujol): 3150, 1670, 1610, 1585 cm$^{-1}$.

N.M.R. spectrum (d$_6$-DMSO, δ): ppm: 7.20 (2H, broad s); 6.85 (1H, s); 3.83 (3H, s).

(8) Ethyl 2-methoxyimino-2-(2-amino-1,3-thiazol-4-yl)acetate hydrobromide (anti isomer) (15.5 g.) was dissolved in a solution of sodium hydroxide (4.4 g.) in water (150 ml.) and the resulting solution was stirred for 1 hour at ambient temperature. An insoluble material was filtered off and the filtrate was adjusted to pH 5.0 to precipitate crystals. The crystals were collected by filtration and dried to give 2-methoxyimino-2-(2-amino-1,3-thiazol-4-yl)acetic acid (anti isomer) (8.0 g.).

I.R. spectrum (Nujol): 3150, 1655, 1595, 1550 cm$^{-1}$.

N.M.R. spectrum (d$_6$-DMSO, δ): ppm: 7.53 (1H, s); 7.23 (2H, broad s); 3.99 (3H, s).

(9) The following compounds were obtained according to similar manner to that of Preparation (9-8).

(1) 2-Methoxyimino-2-(2-methyl-1,3-thiazol-4-yl)acetic acid (anti isomer)

I.R. spectrum (Nujol): 1730, 1590 cm$^{-1}$.

N.M.R. spectrum (d$_6$-DMSO, δ): ppm: 8.10 (1H, s); 4.00 (3H, s); 2.65 (3H, s).

(2) 2-Methoxyimino-2-(2-mesylimino-3-methyl-2,3-dihydro-1,3-thiazol-4-yl)acetic acid (anti isomer).

I.R. spectrum (Nujol): 1730 cm$^{-1}$.

(3) 2-Methoxyimino-2-(2-formamido-1,3-thiazol-4-yl)acetic acid (anti isomer), mp 156° to 158° C. (dec.).

I.R. spectrum (Nujol): 3200, 2700–2100, 1690, 1590, 1560 cm$^{-1}$.

N.M.R. spectrum (d$_6$-DMSO, δ): ppm: 8.05 (1H, s); 4.02 (3H, s).

(10) Ethyl 2-pentyloxyimino-2-(2-amino-1,3-thiazol-4-yl)acetate (syn isomer) (28.6 g.) and 2 N sodium hydroxide aqueous solution (100.2 ml.) were reacted in a mixture of methanol (100 ml.) and tetrahydrofuran (100 ml.) according to similar manners to those of Preparation (9-1) and (9-2) to give 2-pentyloxyimino-2-(2-amino-1,3-thiazol-4-yl)acetic acid (syn isomer) (22.4 g.), mp 176° C. (dec.)

I.R. (Nujol): 3160, 1655, 1620, 1460 cm$^{-1}$.

N.M.R. (d$_6$-DMSO, δ): 7.20 (2H, s), 6.82 (1H, s), 4.07 (2H, t, J=6 Hz), 0.06–2.2 (9H, m).

EXAMPLE 31

Phosphorus oxychloride (0.92 g) was added dropwise over 3 minutes at −5° to −10° C. to a solution of dimethylformamide (0.44 g) in ethyl acetate (2 ml). Ethyl acetate (20 ml) was added thereto and after 10 minutes, 2-isopropoxyimino-2-(2-formamido-1,3-thiazol-4-yl)acetic acid (syn isomer) (1.29 g) was added thereto at −5° to −10° C. The mixture was stirred for 10 minutes to give a clear solution. On the other hand, 7-amino-3-carbamoyloxymethyl-3-cephem-4-carboxylic acid (1.37 g) was dissolved under stirring in a solution of sodium bicarbonate (1.68 g) in water (30 ml), and then acetone (20 ml) was added thereto. To the solution was added dropwise with stirring the ethyl acetate solution obtained above at 0° to 5° C. and at pH 6.5 to 7.5. After stirring for 20 minutes at the same temperature, the aqueous layer was separated and acetone was distilled off. The remaining aqueous layer was adjusted to pH 3.0 with 10% hydrochloric acid under ice-cooling and stirring. Precipitates were collected by filtration, washed with water and dried to give 7-[2-isopropoxyimino-2-(2-formamido-1,3-thiazol-4-yl)acetamido]-3-carbamoyloxymethyl-3-cephem-4-carboxylic acid (syn isomer) (1.5 g).

IR (Nujol): 3450, 3250, 1780, 1710, 1690, 1650 cm$^{-1}$.

NMR (d$_6$-DMSO, δ): 9.63 (1H, d, J=8 Hz), 8.53 (1H, s), 7.43 (1H, s), 6.60 (1H, s), 5.83 (1H, dd, J=5, 8 Hz), 5.20 (1H, d, J=5 Hz), 4.77 (2H, ABq, J=14 Hz), 4.40 (1H, m), 3.57 (2H, broad s), 1.27 (6H, d, J=6 Hz).

EXAMPLE 32

Water (0.05 g) was added to a suspension of 2-allyloxyimino-2-(2-amino-1,3-thiazol-4-yl)acetic acid (syn isomer) (1.0 g) in tetrahydrofuran (10 ml). Phosphorus oxychloride (0.84 g) was added thereto at 0° to 5° C. and the mixture was stirred for 20 minutes at the same temperature. Trimethylsilylacetamide (0.66 g) was added thereto, the mixture was stirred for 20 minutes at the same temperature, phosphorus oxychloride (0.84 g) was added thereto, the resulting mixture was stirred for 20 minutes at 0° to 5° C., dimethylformamide (0.45 g) was added thereto and the resulting mixture was stirred for 1 hour at the same temperature. The resulting solution was added dropwise at −5° to 5° C. and pH 7.0 to 8.0 to a solution, which was prepared by adding acetone (15 ml) and tetrahydrofuran (15 ml) to a solution of 7-amino-3-(1,3,4-thiadiazol-2-yl)thiomethyl-3-cephem-4-carboxylic acid (1.45 g) in a mixture of sodium bicarbonate (0.42 g) and water (10 ml). The resulting mixture was stirred for 2 hours under ice-cooling keeping the pH of the mixture at 7.0 to 8.0 and then adjusted to pH 7.5. An insoluble material was filtered off and the filtrate was washed with ethyl acetate. The aqueous layer was adjusted to pH 6.0 and organic solvent in the aqueous layer was distilled off under reduced pressure. The remaining aqueous layer was adjusted to pH 4.0 and an insoluble material was filtered off. The filtrate was adjusted to pH 3.0 and precipitates were collected by filtration and dried to give 7-[2-allyloxyimino-2-(2-amino-1,3-thiazol-4-yl)acetamido]-3-(1,3,4-thiadiazol-2-yl)thiomethyl-3-cephem-4-carboxylic acid (syn isomer) (1.5 g).

IR (Nujol): 3350, 1780, 1680, 1630 cm$^{-1}$.

NMR (d$_6$-DMSO, δ): 9.63 (1H, d, J=8 Hz), 9.57 (1H, s), 7.23 (2H, m), 6.77 (1H, s), 6.10 (1H, m), 5.83 (1H, dd, J=5, 8 Hz), 5.43 (1H, m), 5.25 (1H, m), 5.17 (1H, d, J=5 Hz), 4.61 (2H, m), 4.47 (2H, ABq, J=14 Hz), 3.72 (2H, m).

EXAMPLE 33

Water (0.1 ml) was added to a suspension of 2-hexyloxyimino-2-(2-amino-1,3-thiazol-4-yl)acetic acid (syn isomer) (2.0 g) in tetrahydrofuran (20 ml). Phosphorus oxychloride (1.4 g) was added thereto at 0° to 5° C. and the mixture was stirred for 20 minutes at the same temperature. Trimethylsilylacetamide (1.3 g) was added thereto, the mixture was stirred for 20 minutes at the same temperature, phosphorus oxychloride (1.4 g) was added thereto, the resulting mixture was stirred for 20 minutes at 0° to 5° C., dimethylformamide (0.75 g) was added thereto and the resulting mixture was stirred for 1 hour at the same temperature. The resulting solution was at a time added at −20° C. to a solution of 7-amino-3-(1H-1,2,3-triazol-5-yl)thiomethyl-3-cephem-4-carboxylic acid (3.3 g) in a mixture of tetrahydrofuran (30 ml) and trimethylsilylacetamide (6.8 g). The resulting mixture was stirred for 1.5 hours at the same temperature. The reaction mixture was post-treated according to similar manners to those of the aforementioned Examples to give 7-[2-hexyloxyimino-2-(2-amino-1,3-thiazol-4-yl)acetamido]-3-(1H-1,2,3-triazol-5-yl)thiomethyl-3-cephem-4-carboxylic acid (syn isomer) (1.5 g).

IR (Nujol): 3100, 1780, 1630 cm$^{-1}$.

NMR (d$_6$-DMSO, δ): 10.17 (1H, d, J=8 Hz), 8.17 (2H, m), 7.97 (1H, s), 7.25 (1H, m), 6.70 (1H, s), 5.73 (1H, dd, J=5, 8 Hz), 5.13 (1H, d, J=5 Hz), 3.97 (2H, m), 3.60 (2H, m), 1.25 (8H, m), 0.83 (3H, m).

EXAMPLE 34

2-(2-Propynyl)oxyimino-2-(2-amino-1,3-thiazol-4-yl)acetic acid (syn isomer) (1.2 g) was suspended in tetrahydrofuran (15 ml). Phosphorus oxychloride (1.0 g) was added thereto at 0° to 5° C. and the mixture was stirred for 20 minutes at the same temperature. Trimethylsilylacetamide (0.5 g) was added thereto, the mixture was stirred for 20 minutes at the same temperature, phosphorus oxychloride (1.0 g) was added thereto, the resulting mixture was stirred for 20 minutes at 0° to 5° C., dimethylformamide (0.5 g) was added thereto and the resulting mixture was stirred for 1 hour at the same temperature. The resulting solution was added dropwise at −5° to 5° C. and pH 6.5 to 8.5 to a solution, which was prepared by adding acetone (10 ml) and tetrahydrofuran (10 ml) to a solution of 7-amino-3-carbamoyloxymethyl-3-cephem-4-carboxylic acid (1.9 g) in a mixture of sodium bicarbonate (0.4 g) and water (15 ml). The resulting mixture was stirred for 2 hours under ice-cooling keeping the pH of the mixture at 7.0 to 8.0 and then adjusted to pH 7.5. An insoluble material was filtered off and the filtrate was washed with ethyl acetate. The aqueous layer was adjusted to pH 6.0 and organic solvent in the aqueous layer was distilled off under reduced pressure. The remaining aqueous layer was adjusted to pH 4.0 and an insoluble material was filtered off. The filtrate was adjusted to pH 3.0 and precipitates were collected by filtration and dried to give 7-[2-(2-propynyl)oxyimino-2-(2-amino-1,3-thiazol-4-yl)acetamido]-3-carbamoyloxymethyl-3-cephem-4-carboxylic acid (syn isomer) (2.2 g).

IR (Nujol): 3300, 1770, 1720, 1640 cm$^{-1}$.

NMR (d$_6$-DMSO, δ): 9.63 (1H, d, J=8 Hz), 7.27 (2H, m), 6.80 (1H, s), 6.58 (2H, s), 5.77 (1H, dd, J=5, 8 Hz), 5.15 (1H, d, J=5 Hz), 4.76 (2H, ABq, J=12 Hz), 4.73 (2H, s), 3.50 (2H, m), 3.45 (1H, m).

EXAMPLE 35

Water (0.33 g) was added to a suspension of 2-propoxyimino-2-(2-amino-1,3-thiazol-4-yl)acetic acid (syn isomer) (4.6 g) in ethyl acetate (46 ml) and the mixture was stirred for 30 minutes at ambient temperature. Phosphorus oxychloride (3.8 g) was added thereto at 0° to 5° C. and the mixture was stirred for 20 minutes at the same temperature. A solution of trimethylsilylacetamide (3.9 g) in ethyl acetate (4 ml) was added dropwise thereto, the mixture was stirred for 20 minutes at 3° to 6° C., phosphorus oxychloride (3.8 g) was added thereto, the resulting mixture was stirred for 20 minutes at 0° to 5° C., dimethylformamide (1.8 g) was added thereto and the resulting mixture was stirred for 1 hour at the same temperature. The resulting solution was added dropwise at −30° C. to a solution, which was prepared by dissolving 7-aminocephalosporanic acid (5.4 g) in a mixture of trimethylsilylacetamide (21 g) and ethyl acetate (100 ml). The resulting mixture was stirred for 1.5 hours at −20° to −10° C. Water (100 ml) was added thereto at −20° C. and the mixture was then adjusted to pH 7.5. An insoluble material was filtered off and the filtrate was washed with ethyl acetate. The aqueous layer was adjusted to pH 6.0 and organic solvent in the aqueous layer was distilled off under reduced pressure. The remaining aqueous layer was adjusted to pH 4.0 and an insoluble material was filtered off. The filtrate was adjusted to pH 3.0 and precipitates were collected by filtration and dried to give 7-[2-propoxyimino-2-(2-amino-1,3-thiazol-4-yl)acetamido]-cephalosporanic acid (syn isomer) (7.5 g).

IR (Nujol): 3400–3200, 1780, 1740, 1660, 1540 cm$^{-1}$.

NMR (d$_6$-DMSO, δ): 9.51 (1H, d, J=8 Hz), 6.68 (1H, s), 5.75 (1H, dd, J=5, 8 Hz), 5.13 (1H, d, J=5 Hz), 4.83 (2H, ABq, J=13 Hz), 4.00 (2H, t, J=7 Hz), 3.53 (2H, ABq, J=18 Hz), 2.03 (3H, s), 1.64 (2H, m), 0.91 (3H, t, J=7 Hz).

EXAMPLE 36

Phosphorus oxychloride (0.92 g) was added dropwise over 3 minutes at −5° to −10° C. to a solution of dimethylformamide (0.44 g) in ethyl acetate (2 ml). Ethyl acetate (20 ml) was added thereto and after 10 minutes, 2-isopropoxyimino-2-(2-formamido-1,3-thiazol-4-yl)acetic acid (syn isomer) (1.29 g) was added thereto at −5° to −10° C. The mixture was stirred for 10 minutes to give a clear solution. On the other hand, 7-amino-3-(1-methyl-1H-tetrazol-5-yl)thiomethyl-3-cephem-4-carboxylic acid (1.64 g) was dissolved under stirring in a solution of sodium bicarbonate (1.68 g) in water (30 ml), and then acetone (20 ml) was added thereto. To the solution was added dropwise with stirring the ethyl acetate solution obtained above at 0° to 5° C. and at pH 6.5 to 7.5. After stirring for 20 minutes at the same temperature, the aqueous layer was separated and acetone was distilled off. The remaining aqueous layer was adjusted to pH 3.0 with 10% hydrochloric acid under ice-cooling and stirring. Precipitates were collected by filtration, washed with water and dried to give 7-[2-isopropoxyimino-2-(2-formamido-1,3-thiazol-4-yl)acetamido]-3-(1-methyl-1H-tetrazol-5-yl)thiomethyl-3-cephem-4-carboxylic acid (syn isomer) (1.7 g).

I R (Nujol): 3500, 3300, 1780, 1730, 1680 cm$^{-1}$.

N M R (d$_6$-DMSO, δ): 9.62 (1H, d, J=8 Hz), 8.53 (1H, s) 7.40 (1H, s), 5.83 (1H, dd, J=5, 8 Hz), 5.17 (1H, d, J=5 Hz), 4.17 (2H, m), 3.97 (3H, s), 3.73 (2H, broad s), 1.27 (6H, d, J=6 Hz).

EXAMPLE 37

Conc.hydrochloric acid (1 ml) was added to a solution of 7-[2-isopropoxyimino-2-(2-formamido-1,3-thiazol-4-yl)acetamido]-3-carbamoyloxymethyl-3-cephem-4-carboxylic acid (syn isomer)(1.3 g) in a mixture of tetrahydrofuran (10 ml) and methanol (10 ml). The mixture was stirred for 3.5 hours at ambient temperature and then concentrated to dryness. Water was added to the residue and to the mixture was added sodium bicarbonate to give a solution. The solution was adjusted to pH 3.0 with conc. hydrochloric acid under ice-cooling. Precipitates were collected by filtration, washed with water and dried to give 7-[2-isopropoxyimino-2-(2-amino-1,3-thiazol-4-yl)acetamido]-3-carbamoyloxymethyl-3-cephem-4-carboxylic acid (syn isomer)(0.25 g).

I R (Nujol): 3300, 3200, 1780, 1720, 1640 cm$^{-1}$.

N M R (d$_6$-DMSO, δ): 9.48 (1H, d, J=8 Hz), 7.24 (2H, broad s), 6.7 (1H, s), 6.54 (1H, s), 5.75 (1H, dd, J=5, 8 Hz), 5.16 (1H, d, J=5 Hz), 4.72 (2H, ABq, J=13 Hz), 4.3 (1H, m), 3.5 (2H, broad s), 1.22 (6H, d, J=6 Hz).

EXAMPLE 38

7-[2-Propoxyimino-2-(2-formamido-1,3-thiazol-4-yl)acetamido]-3-carbamoyloxymethyl-3-cephem-4-carboxylic acid (syn isomer)(0.5 g) was suspended in methanol (15 ml). To the suspension was added conc. hydrochloric acid (0.2 ml) and the mixture was stirred for 2 hours at ambient temperature. The reaction mixture was concentrated and the residue was washed with tetrahydrofuran, collected by filtration and dried to give 7-[2-propoxyimino-2-(2-amino-1,3-thiazol-4-yl)acetamido]-3-carbamoyloxymethyl-3-cephem-4-carboxylic acid hydrochloride (syn isomer)(0.4 g).

I R (Nujol): 3350, 3200, 1770, 1720, 1665, 1630, 1550 cm$^{-1}$.

N M R (d$_6$-DMSO, δ): 9.82 (1H, d, J=8 Hz), 6.98 (1H, s), 5.80 (1H, dd, J=5, 8 Hz), 5.22 (1H, d, J=5 Hz), 4.80 (2H, ABq, J=14 Hz), 4.15 (2H, t, J=7 Hz), 3.58 (2H, broad s), 1.72 (2H, m), 0.92 (3H, t, J=7 Hz).

EXAMPLE 39

Conc. hydrochloric acid (1 ml) was added to a solution of 7-[2-isopropoxyimino-2-(2-formamido-1,3-thiazol-4-yl)acetamido]-3-(1-methyl-1H-tetrazol-5-yl)thiomethyl-3-cephem-4-carboxylic acid (syn isomer)(1.5 g) in a mixture of tetrahydrofuran (12 ml) and methanol (12 ml). The mixture was stirred for 3.5 hours at ambient temperature and then concentrated to dryness. Water was added to the residue and to the mixture was added sodium bicarbonate to give a solution. The solution was adjusted to pH 3.0 with conc. hydrochloric acid under ice-cooling. Precipitates were collected by filtration, washed with water and dried to give 7-[2-isopropoxyimino-2-(2-amino-1,3-thiazol-4-yl)acetamido]-3-(1-methyl-1H-tetrazol-5-yl)thiomethyl-3-cephem-4-carboxylic acid (syn isomer)(0.8 g).

I R (Nujol): 3330, 3250, 1780, 1680 cm$^{-1}$.

N M R (d$_6$-DMSO, δ): 9.50 (1H, d, J=8 Hz), 6.70 (1H, s), 5.83 (1H, dd, J=5, 8 Hz), 5.17 (1H, d, J=5 Hz), 4.33 (2H, broad s), 3.97 (3H, s), 3.71 (2H, broad s), 1.25 (6H, d, J=6 Hz).

EXAMPLE 40

The following compounds were obtained according to similar manners to those of the aforementioned Examples.

(1) 7-[2-Isobutoxyimino-2-(2-amino-1,3-thiazol-4-yl)acetamido]cephalosporanic acid (syn isomer).

I R (Nujol): 3400–3200, 1780, 1740, 1660, 1630, 1540 cm$^{-1}$.

N M R (d$_6$-DMSO, δ): 9.56 (1H, d, J=8 Hz), 6.72 (1H, s), 5.78 (1H, dd, J=5, 8 Hz), 5.14 (1H, d, J=5 Hz), 4.83 (2H, ABq, J=14 Hz), 3.82 (2H, d, J=7 Hz), 3.54 (2H, ABq, J=17 Hz), 2.02 (3H, s), 1.98 (1H, m), 0.88 (6H, d, J=7 Hz).

(2) 7-[2-Cyclohexyloxyimino-2-(2-amino-1,3-thiazol-4-yl)acetamido]cephalosporanic acid (syn isomer).

I R (Nujol): 3400–3200, 1780, 1740, 1670, 1630, 1530 cm$^{-1}$.

N M R (d$_6$-DMSO, δ): 9.46 (1H, d, J=8 Hz), 6.72 (1H, s), 5.76 (1H, dd, J=5, 8 Hz), 5.10 (1H, d, J=5 Hz), 4.84 (2H, ABq, J=13 Hz), 4.00 (1H, m), 3.50 (2H, broad s), 2.00 (3H, s), 1.00–2.00 (10H, m).

(3) 7-[2-(2-Propynyl)oxyimino-2-(2-amino-1,3-thiazol-4-yl)acetamido]cephalosporanic acid (syn isomer).

I R (Nujol): 3310, 1780, 1740, 1670 cm$^{-1}$.

N M R (d$_6$-DMSO, δ): 9.72 (1H, d, J=8 Hz), 7.3 (2H, m), 6.83 (1H, s), 5.83 (1H, dd, J=5, 8 Hz), 5.20 (1H, d, J=5 Hz), 4.87 (2H, ABq, J=13 Hz), 4.77 (2H, d, J=2 Hz), 3.60 (2H, m), 3.50 (1H, m), 2.11 (3H, s).

(4) 7-[2-Propoxyimino-2-(2-amino-1,3-thiazol-4-yl)acetamido]-3-(1-methyl-1H-tetrazol-5-yl)thiomethyl-3-cephem-4-carboxylic acid (syn isomer).

I R (Nujol): 3400–3200, 1780, 1670, 1630, 1535 cm$^{-1}$.

N M R (d$_6$-DMSO, δ): 9.57 (1H, d, J=8 Hz), 6.72 (1H, s), 5.77 (1H, dd, J=5, 8 Hz), 5.13 (1H, d, J=5 Hz), 4.30 (2H, ABq, J=14 Hz), 4.02 (2H, t, J=7 Hz), 3.93 (3H, s), 3.69 (2H, ABq, J=18 Hz), 1.64 (2H, m), 0.90 (3H, t, J=7 Hz).

(5) 7-[2-Pentyloxyimino-2-(2-amino-1,3-thiazol-4-yl)acetamido]-3-(1-methyl-1H-tetrazol-5-yl)thiomethyl-3-cephem-4-carboxylic acid (syn isomer).

I R (Nujol): 3300, 1770, 1660, 1630 cm$^{-1}$.

N M R (d$_6$-DMSO, δ): 9.52 (1H, d, J=8 Hz), 7.20 (2H, m), 6.68 (1H, s), 5.74 (1H, dd, J=4, 8 Hz), 5.10 (1H, d, J=4 Hz), 4.30 (2H, ABq, J=13 Hz), 4.02 (2H, t, J=6 Hz), 3.90 (3H, s), 3.66 (2H, ABq, J=18 Hz), 1.60 (2H, m), 1.30 (4H, m), 0.82 (3H, t, J=6 Hz).

(6) 7-[2-Hexyloxyimino-2-(2-amino-1,3-thiazol-4-yl)acetamido]-3-(1-methyl-1H-tetrazol-5-yl)thiomethyl-3-cephem-4-carboxylic acid (syn isomer).

I R (Nujol): 3350, 3250, 1780, 1670, 1630 cm$^{-1}$.

N M R (d$_6$-DMSO, δ): 10.25 (1H, d, J=5 Hz), 7.25 (2H, m), 6.73 (1H, s), 5.77 (1H, dd, J=5, 8 Hz), 5.13 (1H, d, J=5 Hz), 4.17 (2H, m), 3.91 (3H, s), 3.67 (2H, m), 1.33 (8H, m), 0.83 (3H, m).

(7) 7-[2-Ethoxyimino-2-(2-formamido-1,3-thiazol-4-yl)acetamido]-3-carbamoyloxymethyl-3-cephem-4-carboxylic acid (syn isomer).

I R (Nujol): 3500, 3300, 1780, 1710, 1660 cm$^{-1}$.

N M R (d$_6$-DMSO, δ): 9.67 (1H, d, J=8 Hz), 8.53 (1H, s), 7.43 (1H, s), 6.58 (1H, s), 5.87 (1H, dd, J=5, 8 Hz), 5.23 (1H, d, J=5 Hz), 4.80 (2H, ABq, J=13 Hz), 4.23 (2H, q, J=7 Hz), 3.57 (2H, broad s), 1.3 (3H, t, J=7 Hz).

(8) 7-[2-Ethoxyimino-2-(2-amino-1,3-thiazol-4-yl)acetamido]-3-carbamoyloxymethyl-3-cephem-4-carboxylic acid (syn isomer).

I R (Nujol): 3300, 3200, 1780, 1720, 1660 cm$^{-1}$.

N M R (d$_6$-DMSO, δ): 9.58 (1H, d, J=8 Hz), 7.33 (1H, broad s), 6.77 (1H, s), 6.58 (1H, s), 5.83 (1H, dd, J=4, 8 Hz), 5.20 (1H, d, J=4 Hz), 4.77 (2H, ABq, J=12 Hz), 4.16 (2H, q, J=7 Hz), 3.53 (2H, broad s), 1.23 (3H, t, J=7 Hz).

(9) 7-[2-Propoxyimino-2-(2-formamido-1,3-thiazol-4-yl)acetamido]-3-carbamoyloxymethyl-3-cephem-4-carboxylic acid (syn isomer).

I R (Nujol): 3250, 3200, 1780, 1700, 1660, 1525 cm$^{-1}$.

N M R (d$_6$-DMSO, δ): 9.62 (1H, d, J=8 Hz), 8.50 (1H, s), 7.43 (1H, s), 6.57 (2H, broad s), 5.84 (1H, dd, J=5, 8 Hz), 5.18 (1H, d, J=5 Hz), 4.58 (2H, ABq, J=13 Hz), 4.08 (2H, t, J=7 Hz), 3.54 (2H, ABq, J=18 Hz), 1.68 (2H, m), 0.92 (3H, t, J=7 Hz).

(10) 7-[2-Isobutoxyimino-2-(2-formamido-1,3-thiazol-4-yl)acetamido]-3-carbamoyloxymethyl-3-cephem-4-carboxylic acid (syn isomer).

I R (Nujol): 3450, 3300, 1780, 1710, 1680, 1610 cm$^{-1}$.

N M R (d$_6$-DMSO, δ): 9.6 (1H, d, J=8 Hz), 8.5 (1H, s), 7.18 (1H, s), 6.6 (2H, broad s), 5.8 (1H, dd, J=5, 8 Hz), 5.15 (1H, d, J=5 Hz), 4.76 (2H, ABq, J=13 Hz), 3.84 (2H, d, J=6 Hz), 3.5 (2H, ABq, J=18 Hz), 2.04 (1H, m), 0.88 (6H, d, J=6 Hz).

(11) 7-[2-Isobutoxyimino-2-(2-amino-1,3-thiazol-4-yl)acetamido]-3-carbamoyloxymethyl-3-cephem-4-carboxylic acid (syn isomer).

I R (Nujol): 3300, 1770, 1730, 1660 cm$^{-1}$.

N M R (d$_6$-DMSO, δ): 9.55 (1H, d, J=9 Hz), 7.27 (2H, broad s), 6.73 (1H, s), 6.60 (1H, broad s), 5.83 (1H, dd, J=5, 9 Hz), 5.20 (1H, d, J=5 Hz), 4.80 (2H, ABq, J=12 Hz), 3.87 (2H, d, J=7 Hz), 3.53 (2H, ABq, J=18 Hz), 0.90 (6H, d, J=7 Hz).

(12) 7-[2-Allyloxyimino-2-(2-amino-1,3-thiazol-4-yl)acetamido]-3-carbamoyloxymethyl-3-cephem-4-carboxylic acid (syn isomer).

I R (Nujol): 3300, 1770, 1720, 1660, 1630 cm$^{-1}$.

N M R (d$_6$-DMSO, δ): 9.82 (1H, d, J=8 Hz), 7.20 (2H, m), 6.92 (1H, s), 6.7 (2H, m), 6.0 (1H, m), 5.80 (1H, dd, J=5, 8 Hz), 5.40 (1H, m), 5.22 (1H, m), 5.13 (1H, d, J=5 Hz), 4.70 (2H, ABq, J=14 Hz), 4.65 (2H, m), 3.50 (2H, ABq, J=16 Hz).

(13) 7-[2-Propoxyimino-2-(2-amino-1,3-thiazol-4-yl)acetamido]-3-(1,3,4-thiadiazol-2-yl)thiomethyl-3-cephem-4-carboxylic acid (syn isomer).

I R (Nujol): 3400-3200, 1780, 1670, 1625, 1540 cm$^{-1}$.

N M R (d$_6$-DMSO, δ): 9.50 (1H, s), 9.50 (1H, d, J=8 Hz), 6.68 (1H, s), 5.74 (1H, dd, J=5, 8 Hz), 5.12 (1H, d, J=5 Hz), 4.40 (2H, ABq, J=14 Hz), 3.98 (2H, t, J=7 Hz), 3.66 (2H, ABq, J=17 Hz), 1.62 (2H, m), 0.87 (3H, t, J=7 Hz).

(14) 7-[2-Ethoxyimino-2-(2-formamido-1,3-thiazol-4-yl)acetamido]-3-(1H-1,2,3-triazol-5-yl)thiomethyl-3-cephem-4-carboxylic acid (syn isomer).

I R (Nujol): 3500, 3200, 1780, 1670, 1620 cm$^{-1}$.

N M R (d$_6$-DMSO, δ): 9.64 (1H, d, J=8 Hz), 8.5 (1H, s), 7.9 (1H, s), 7.4 (1H, s), 5.76 (1H, dd, J=4, 8 Hz), 5.14 (1H, d, J=4 Hz), 4.1 (2H, q, J=7 Hz), 3.92 (2H, ABq, J=13 Hz), 3.58 (2H, ABq, J=18 Hz), 1.26 (6H, t, J=7 Hz).

(15) 7-[2-Ethoxyimino-2-(2-amino-1,3-thiazol-4-yl)acetamido]-3-(1H-1,2,3-triazol-5-yl)thiomethyl-3-cephem-4-carboxylic acid (syn isomer).

I R (Nujol): 3350, 3150, 1770, 1670 cm$^{-1}$.

N M R (d$_6$-DMSO, δ): 9.56 (1H, d, J=9 Hz), 7.92 (1H, s), 7.28 (1H, m), 6.75 (1H, s), 5.75 (1H, dd, J=5, 9 Hz), 5.06 (1H, d, J=5 Hz), 4.05 (2H, q, J=7 Hz), 3.9 (2H, m), 3.64 (2H, ABq, J=17 Hz), 1.24 (3H, t, J=7 Hz).

(16) 7-[2-Propoxyimino-2-(2-formamido-1,3-thiazol-4-yl)acetamido]-3-(1H-1,2,3-triazol-5-yl)thiomethyl-3-cephem-4-carboxylic acid (syn isomer).

I R (Nujol): 3300-3100, 1780, 1680, 1650, 1550 cm$^{-1}$.

N M R (d$_6$-DMSO, δ): 9.62 (1H, d, J=8 Hz), 8.50 (1H, s), 7.92 (1H, s), 7.38 (1H, s), 5.78 (1H, dd, J=5, 8 Hz), 5.15 (1H, d, J=5 Hz), 4.20-3.70 (4H, m), 3.65 (2H, ABq, J=17 Hz), 1.66 (1H, m), 0.90 (3H, t, J=7 Hz).

(17) 7-[2-Propoxyimino-2-(2-amino-1,3-thiazol-4-yl)acetamido]-3-(1H-1,2,3-triazol-5-yl)thiomethyl-3-cephem-4-carboxylic acid (syn isomer).

I R (Nujol): 3400-3100, 1770, 1670, 1630, 1530 cm$^{-1}$.

N M R (d$_6$-DMSO, δ): 9.58 (1H, d, J=8 Hz), 7.97 (1H, s), 6.77 (1H, s), 5.78 (1H, dd, J=5, 8 Hz), 5.18 (1H, d, J=5 Hz), 4.23-3.76 (4H, m), 3.67 (2H, broad s), 1.67 (2H, m), 0.93 (3H, t, J=7 Hz).

(18) 7-[2-Isopropoxyimino-2-(2-amino-1,3-thiazol-4-yl)acetamido]-3-(1H-1,2,3-triazol-5-yl)thiomethyl-3-cephem-4-carboxylic acid (syn isomer).

I R (Nujol): 3300, 3150, 1780, 1670, 1640 cm$^{-1}$.

N M R (d$_6$-DMSO, δ): 9.50 (1H, d, J=9 Hz), 7.97 (1H, s), 6.73 (1H, s), 5.77 (1H, dd, J=5, 9 Hz), 5.17 (1H, d, J=5 Hz), 4.33 (1H, m), 4.0 (2H, ABq, J=13 Hz), 3.67 (2H, ABq, J=18 Hz), 1.23 (6H, d, J=6 Hz).

(19) 7-[2-Isobutoxyimino-2-(2-amino-1,3-thiazol-4-yl)acetamido]-3-(1H-1,2,3-triazol-5-yl)thiomethyl-3-cephem-4-carboxylic acid (syn isomer).

I R (Nujol): 3470, 3320, 3200, 3160, 1770, 1660 cm$^{-1}$.

N M R (d$_6$-DMSO, δ): 9.57 (1H, d, J=9 Hz), 7.97 (1H, s), 7.22 (2H, broad s), 6.75 (1H, s), 5.77 (1H, dd, J=5, 9 Hz), 5.18 (1H, d, J=5 Hz), 4.03 (2H, ABq, J=12 Hz), 3.88 (2H, d, J=6 Hz), 3.70 (2H, ABq, J=18 Hz), 2.0 (1H, m), 0.92 (6H, d, J=6 Hz).

(20) 7-[2-(2-Propynyl)oxyimino-2-(2-amino-1,3-thiazol-4-yl)acetamido]-3-(1H-1,2,3-triazol-5-yl)thiomethyl-3-cephem-4-carboxylic acid (syn isomer).

I R (Nujol): 3320, 3150, 1770, 1670, 1630 cm$^{-1}$.

N M R (d$_6$-DMSO, δ): 9.67 (1H, d, J=8 Hz), 7.98 (1H, s), 6.83 (1H, s), 5.75 (1H, dd, J=4, 8 Hz), 5.18 (1H, d, J=4 Hz), 4.77 (2H, m), 4.0 (2H, ABq, J=13 Hz), 3.70 (2H, ABq, J=18 Hz), 3.48 (1H, m).

EXAMPLE 41

Phosphorus oxychloride (974 mg) was added dropwise over 3 minutes at −5° to −10° C. to a solution of dimethylformamide (464 mg) in tetrahydrofuran (3 ml). Tetrahydrofuran (12 ml) was added thereto and after 10 minutes, 2-cyclopentyloxyimino-2-(2-formamidothiazol-4-yl)acetic acid (syn isomer)(1.5 g) was added thereto at −5° to −10° C. The mixture was stirred for 10 minutes to give a clear solution. On the other hand, 7-amino-3-(1,3,4-thiadiazol-2-yl)thiomethyl-3-cephem-4-carboxylic acid (2.27 g) was dissolved under stirring in a solution of triethylamine (1.3 g) in 50% aqueous acetone (23 ml).

To the solution was added dropwise with stirring the tetrahydrofuran solution obtained above at 0° to 5° C. and at pH 6.5 to 7.5. After stirring for 30 minutes at the same temperature, the reaction mixture was poured into a mixture of water and ethyl acetate and adjusted to pH 3.0 with 10% hydrochloric acid. After filterring off an insoluble material, the filtrate was twice extracted with ethyl acetate. The extracts were washed 3 times with a saturated aqueous solution of sodium chloride and dried over magnesium sulfate. The solvent was distilled off and the residue was triturated with diethyl ether, collected by filtration and dried to give 7-[2-cyclopentyloxyimino-2-(2-formamidothiazol-4-yl)acetamido]-3-(1,3,4-thiadiazol-2-yl)thiomethyl-3-cephem-4-carboxylic acid (syn isomer)(2.8 g).

I. R. (Nujol): 3240, 3180, 1780, 1670, 1540 $cm^{-1}$.

N.M.R. (DMSO-$d_6$, $\delta$): 1.2–2.3 (8H, m), 3.72 (2H, s), 4.45 (2H, ABq, J=14 Hz), 4.74 (1H, broad s), 5.17 (1H, d, J=5 Hz), 5.82 (1H, dd, J=5 and 8 Hz), 7.36 (1H, s), 8.56 (1H, s), 9.52 (1H, s), 9.55 (1H, d, J=8 Hz), 12.56 (1H, broad s).

EXAMPLE 42

The following compounds were obtained according to a similar manner to that of Example 41.

(1) 7-[2-Cyclopentyloxyimino-2-{2-(2,2,2-trifluoroacetamido)thiazol-4-yl}acetamido]cephalosporanic acid (syn isomer), powder.

(2) 7-[2-Cyclopentyloxyimino-2-(2-aminothiazol-4-yl)acetamido]cephalosporanic acid (syn isomer).

I.R. (Nujol): 3270, 1760, 1650 $cm^{-1}$.

N.M.R. (DMSO-$d_6$, $\delta$): 1.27–2.17 (8H, m), 2.04 (3H, s), 3.58 (2H, m), 4.74 (1H, m), 4.87 (2H, ABq, J=13.0 Hz), 5.17 (1H, d, J=4.0 Hz), 5.82 (1H, dd, J=4.0 and 8.0 Hz), 6.74 (1H, s), 9.54 (1H, d, J=8.0 Hz).

(3) 7-[2-Cyclopentyloxyimino-2-(2-formamidothiazol-4-yl)acetamido]-3-(1H-tetrazol-5-yl)thiomethyl-3-cephem-4-carboxylic acid (syn isomer).

I.R. (Nujol): 3150, 1770, 1660 $cm^{-1}$.

N.M.R. (DMSO-$d_6$, $\delta$): 1.37–2.33 (8H, m), 3.75 (2H, m), 4.38 (2H, ABq, J=14.0 Hz), 4.78 (1H, m), 5.21 (1H, d, J=5.0 Hz), 5.88 (1H, dd, J=5.0 and 8.0 Hz), 7.42 (1H, s), 8.56 (1H, s), 9.62 (1H, d, J=8.0 Hz).

(4) 7-[2-Cyclopentyloxyimino-2-(2-aminothiazol-4-yl)acetamido]-3-(1H-tetrazol-5-yl)thiomethyl-3-cephem-4-carboxylic acid (syn isomer), mp 185° to 195° C. (dec.).

I.R. (Nujol): 3260, 1760, 1640 $cm^{-1}$.

N.M.R. (DMSO-$d_6$, $\delta$): 1.17–2.30 (8H, m), 3.71 (2H, ABq, J=18.0 Hz), 4.32 (2H, ABq, J=13.0 Hz), 4.68 (1H, m), 5.14 (1H, d, J=4.0 Hz), 5.76 (1H, dd, J=4.0 and 8.0 Hz), 6.71 (1H, s), 9.50 (1H, d, J=8.0 Hz).

(5) 7-[2-Cyclopentyloxyimino-2-{2-(2,2,2-trifluoroacetamido)thiazol-4-yl}acetamido]-3-(1-methyl-1H-tetrazol-5-yl)thiomethyl-3-cephem-4-carboxylic acid (syn isomer).

I.R. (Nujol): 3200, 1780, 1720, 1680, 1625 $cm^{-1}$.

N.M.R. (DMSO-$d_6$, $\delta$): 1.34–2.23 (8H, m), 3.77 (2H, m), 3.98 (3H, s), 4.36 (2H, m), 4.78 (1H, m), 5.21 (1H, d, J=4.0 Hz), 5.87 (1H, dd, J=4.0 and 8.0 Hz), 7.52 (1H, s), 9.71 (1H, d, J=8.0 Hz).

(6) 7-[2-Cyclopentyloxyimino-2-(2-aminothiazol-4-yl)acetamido]-3-(1-methyl-1H-tetrazol-5-yl)thiomethyl-3-cephem-4-carboxylic acid (syn isomer), mp 152° to 154° C. (dec.).

I.R. (Nujol): 3300, 3200, 1770, 1660, 1620 $cm^{-1}$.

N.M.R. (DMSO-$d_6$, $\delta$): 1.28–2.11 (8H, m), 3.74 (2H, m), 3.97 (3H, s), 4.35 (2H, m), 4.72 (1H, m), 5.17 (1H, d, J=5.0 Hz), 5.80 (1H, dd, J=5.0 and 8.0 Hz), 6.74 (1H, s), 9.54 (1H, d, J=8.0 Hz).

(7) 7-[2-Cyclopentyloxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3260, 1760, 1645, 1520 $cm^{-1}$.

N.M.R. (DMSO-$d_6$, $\delta$): 1.2–2.3 (8H, m), 3.69 (2H, s), 4.43 (2H, ABq, J=14 Hz), 4.66 (1H, broad s), 5.12 (1H, d, J=5 Hz), 5.73 (1H, dd, J=5 and 8 Hz), 6.67 (1H, s), 7.17 (2H, broad s), 9.43 (1H, d, J=8 Hz), 9.51 (1H, s).

EXAMPLE 43

Conc. hydrochloric acid (1.8 g) was added to a solution of 7-[2-cyclopentyloxyimino-2-(2-formamidothiazol-4-yl)acetamido]-3-(1,3,4-thiadiazol-2-yl)thiomethyl-3-cephem-4-carboxylic acid (syn isomer) (2.7 g) in methanol (27 ml) and the mixture was stirred for 2 hours at ambient temperature. An insoluble material was filtered off and the filtrate was concentrated to dryness under reduced pressure and the residue was triturated with diethyl ether and dried to give 7-[2-cyclopentyloxyimino-2-(2-aminothiazol-4-yl)acetamido]-3-(1,3,4-thiadiazol-2-yl)thiomethyl-3-cephem-4-carboxylic acid hydrochloride (syn isomer) (2.9 g). The powder (2.9 g) was dissolved in an aqueous solution of sodium hydroxide to adjust pH 7.5. The solution was adjusted to pH 3.0 and precipitates were collected by filtration and washed with water to give 7-[2-cyclopentyloxyimino-2-(2-aminothiazol-4-yl)acetamido]-3-(1,3,4-thiadiazol-2-yl)thiomethyl-3-cephem-4-carboxylic acid (syn isomer) (1.95 g).

I.R. (Nujol): 3260, 1760, 1645, 1520 $cm^{-1}$.

N.M.R. (DMSO-$d_6$, $\delta$): 1.2–2.3 (8H, m), 3.69 (2H, s), 4.43 (2H, ABq, J=14 Hz), 4.66 (1H, broad s), 5.12 (1H, d, J=5 Hz), 5.73 (1H, dd, J=5 and 8 Hz), 6.67 (1H, s), 7.17 (2H, broad s), 9.43 (1H, d, J=8 Hz), 9.51 (1H, s).

EXAMPLE 44

7-[2-Cyclopentyloxyimino-2-{2-(2,2,2-trifluoroacetamido)thiazol-4-yl}acetamido]-3-(1-methyl-1H-tetrazol-5-yl)thiomethyl-3-cephem-4-carboxylic acid (syn isomer) (2.8 g) was added to a solution of sodium acetate trihydrate (5.8 g) in water (25 ml), and tetrahydrofuran (8.0 ml) was added thereto to give clear solution. The solution was stirred for 16 hours at ambient temperature. To the reaction mixture were added water and ethyl acetate and the mixture was adjusted to pH 6.2 with a saturated aqueous solution of sodium bicarbonate. The separated aqueous layer was washed twice with ethyl acetate and adjusted to pH 3.0 with 10% hydrochloric acid. Precipitates were collected by filtration, washed with water and dried under reduced pressure to give 7-[2-cyclopentyloxyimino-2-(2-aminothiazol-4-yl)acetamido]-3-(1-methyl-1H-tetrazol-5yl)- thiomethyl-3-cephem-4-carboxylic acid (syn isomer) (1.63 g), mp 152° to 154° C. (dec.).

I.R. (Nujol): 3300, 3200, 1770, 1660, 1620 cm$^{-1}$.

N.M.R. (DMSO-d$_6$, δ): 1.28-2.11 (8H, m), 3.74 (2H, m), 3.97 (3H, s), 4.35 (2H, m), 4.72 (1H, m), 5.17 (1H, d, J=5.0 Hz), 5.80 (1H, dd, J=5.0 and 8.0 Hz), 6.74 (1H, s), 9.54 (1H, d, J=8.0 Hz).

EXAMPLE 45

The following compounds were obtained according to similar manners to those of Examples 43 and 44.

(1) 7-[2-Cyclopentyloxyimino-2-(2-aminothiazol-4-yl)acetamido]cephalosporanic acid (syn isomer).

I.R. (Nujol): 3270, 1760, 1650 cm$^{-1}$.

N.M.R. (DMSO-d$_6$, δ): 1.27-2.17 (8H, m), 2.04 (3H, s), 3.58 (2H, m), 4.74 (1H, m), 4.87 (2H, ABq, J=13.0 Hz), 5.17 (1H, d, J=4.0 Hz), 5.82 (1H, dd, J=4.0 and 8.0 Hz), 6.74 (1H, s), 9.54 (1H, d, J=8.0 Hz).

(2) 7-[2-Cyclopentyloxyimino-2-(2-aminothiazol-4-yl)acetamido]-3-(1H-tetrazol-5-yl)thiomethyl-3-cephem-4-carboxylic acid (syn isomer), mp 185° to 190° C. (dec.).

I.R. (Nujol): 3260, 1760, 1640 cm$^{-1}$.

N.M.R. (DMSO-d$_6$, δ): 1.17-2.30 (8H, m), 3.71 (2H, ABq, J=18 Hz), 4.32 (2H, ABq, J=13.0 Hz), 4.68 (1H, m), 5.14 (1H, d, J=4.0 Hz), 5.76 (1H, dd, J=4.0 and 8.0 Hz), 6.71 (1H, s), 9.50 (1H, d, J=8.0 Hz).

Preparation 10

The following compounds were obtained in any of a similar manner to those of aforesaid Preparations.

(1) Ethyl 2-cyclopentyloxyimino-3-oxobutyrate (syn isomer), oil.

I.R. $\nu_{max}^{Film}$: 1740, 1670, 1495, 1430 cm$^{-1}$.

N.M.R. δ(CCl$_4$, ppm): 1.32 (3H, t, J=7 Hz), 1.4-2.2 (8H, m), 2.33 (3H, s), 4.27 (2H, q, J=7 Hz), 4.87 (1H, m).

(2) Ethyl 4-chloro-2-cyclopentyloxyimino-3-oxobutyrate (syn isomer), oil.

I.R. $\nu_{max}^{Film}$: 1735, 1750, 1465, 1435 cm$^{-1}$.

N.M.R. δ(CCl$_4$, ppm): 1.33 (3H, t, J=7 Hz), 1.3-2.4 (8H, m), 4.28 (2H, q, J=7 Hz) 4.46 (2H, s), 4.86 (1H, s).

(3) Ethyl 2-(2-aminothiazol-4-yl)-2-cyclopentyloxyiminoacetate (syn isomer), mp. 134°-136° C.

I.R. $\nu_{max}^{Nujol}$: 3490, 3450, 3250, 3120, 1735, 1540, 1460 cm$^{-1}$.

N.M.R. δ(DMSO-d$_6$): 1.25 (3H, t, J=7 Hz), 1.62 (8H, broad s), 4.27 (2H, q, J=7 Hz), 4.70 (1H, m), 6.85 (1H, s), 7.20 (2H, s).

(4) 2-(2-Aminothiazol-4-yl)-2-cyclopentyloxyiminoacetic acid (syn isomer), mp. 186° C. (dec.).

I.R. $\nu_{max}^{Nujol}$: 3330, 3120, 1635, 1450 cm$^{-1}$.

N.M.R. δ(DMSO-d$_6$): 1.1-2.2 (8H, m), 4.68 (1H, m), 6.81 (1H, s), 7.18 (2H, broad s).

(5) 2-[2-(2,2,2-trifluoroacetamido)thiazol-4-yl]-2-cyclopentyloxyiminoacetic acid (syn isomer).

I.R. $\nu_{max}^{Nujol}$: 3200, 3130, 1720, 1590, 1580 cm$^{-1}$.

N.M.R. δ(DMSO-d$_6$): 1.34-2.22 (8H, m), 4.81 (1H, m), 7.71 (1H, s).

(6) To acetic anhydride (32 g.) was added formic acid (14.4 g.) under ice-cooling and stirred at 40° to 45° C. for an hour. 2-(2-Aminothiazol-4-yl)-2-cyclopentyloxyiminoacetic acid (syn isomer, 20 g.) and tetrahydrofuran (100 ml.) were added to the solution under ice-cooling and stirred at 35° C. for 3 hours. After the solution was concentrated in vacuo, the residue was pulverized with diisopropyl ether, and dried over phosphorus pentoxide to give 2-(2-formamidothiazol-4-yl)-2-cyclopentyloxyiminoacetic acid (syn isomer, 9.04 g.), mp. 158° C. (dec.).

I.R. $\nu_{max}^{Nujol}$: 3100, 1730, 1695, 1685, 1550, 1495 cm$^{-1}$.

N.M.R. δ(DMSO-d$_6$): 1.2-2.3 (8H, m), 4.77 (1H, quintet, J=4 Hz), 7.93 (1H, s), 9.37 (1H, s).

What we claim is:

1. Syn isomer of 7-[2-cyclopentyloxyimino-2-(2-amino- or substituted aminothiazol-4-yl)acetamido]-3-heterocyclicthiomethyl-3-cephem-4-carboxylic acid compounds of the formula:

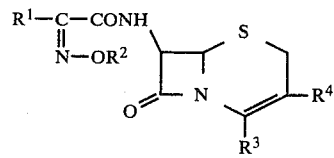

wherein
R$^1$ is

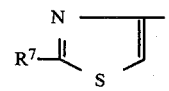

R$^7$ is amino or lower alkanoylamino;
R$^2$ is cyclopentyl;
R$^3$ is carboxy; and
R$^4$ is thiadiazolylthiomethyl and pharmaceutically acceptable salts thereof.

2. A compound of claim 1, wherein
R$^7$ is amino or formamido,
R$^2$ is cyclopentyl, and
R$^4$ is 1,3,4-thiadiazol-2-ylthiomethyl.

3. A compound of claim 2, which is 7-[2-cyclopentyloxyimino-2-(2-aminothiazol-4-yl)acetamido]-3-(1,3,4-thiadiazol-2-yl)thiomethyl-3-cephem-4-carboxylic acid (syn isomer).

4. A pharmaceutically antibacterial composition comprising a compound of claim 1 or pharmaceutically acceptable salt thereof in association with a pharmaceutically acceptable, substantially non-toxic carrier or excipient.

* * * * *